US012612648B2

(12) United States Patent
Suzuki et al.

(10) Patent No.: US 12,612,648 B2
(45) Date of Patent: Apr. 28, 2026

(54) PRODUCTION METHOD FOR GENOME-EDITED CELLS

(71) Applicant: KYUSHU UNIVERSITY, NATIONAL UNIVERSITY CORPORATION, Fukuoka (JP)

(72) Inventors: Atsushi Suzuki, Fukuoka (JP); Masaki Kawamata, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 959 days.

(21) Appl. No.: 17/311,137

(22) PCT Filed: Dec. 12, 2019

(86) PCT No.: PCT/JP2019/048781
§ 371 (c)(1),
(2) Date: Jun. 4, 2021

(87) PCT Pub. No.: WO2020/122195
PCT Pub. Date: Jun. 18, 2020

(65) Prior Publication Data
US 2022/0025405 A1    Jan. 27, 2022

(30) Foreign Application Priority Data
Dec. 12, 2018    (JP) ................................. 2018-232946

(51) Int. Cl.
| | |
|---|---|
| *C12N 15/90* | (2006.01) |
| *C12N 9/22* | (2006.01) |
| *C12N 15/11* | (2006.01) |
| *G01N 21/64* | (2006.01) |
| *G16B 30/00* | (2019.01) |

(52) U.S. Cl.
CPC ............. *C12N 15/902* (2013.01); *C12N 9/22* (2013.01); *C12N 15/11* (2013.01); *G01N 21/6486* (2013.01); *G16B 30/00* (2019.02); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 2015/0059010 A1 | 2/2015 | Cigan et al. | |
| 2015/0284727 A1 | 10/2015 | Kim et al. | |
| 2016/0289675 A1* | 10/2016 | Ryan ...................... | C07H 21/02 |
| 2017/0355985 A1* | 12/2017 | Dellinger .............. | C12N 15/111 |
| 2018/0282722 A1 | 10/2018 | Jakimo et al. | |

FOREIGN PATENT DOCUMENTS

| | | |
|---|---|---|
| CN | 104854241 A | 8/2015 |
| CN | 104968784 A | 10/2015 |
| CN | 106191116 A | 12/2016 |
| JP | 2015-523856 A | 8/2015 |
| JP | 2016-500003 A | 1/2016 |
| WO | WO 2013/176772 A1 | 11/2013 |
| WO | WO 2014/093661 A2 | 6/2014 |
| WO | WO 2018/060238 A1 | 4/2018 |

OTHER PUBLICATIONS

Okafor, I.C., et al. 2019 Nucleic Acids Research 47(22): 11880-11888, published online Nov. 12, 2019. (Year: 2019).*
Farboud, B., et al. 2015 Genetics 199: 959-971. (Year: 2015).*
Anderson et al., "Systematic Analysis of CRISPR-Cas9 Mismatch Tolerance Reveals Low Levels of Off-Target Activity", Journ. Biotechnology, 211: 56-65, 2015.
International Search Report and Written Opinion for PCT International Patent Application No. PCT/JP2019/048781, mailed Mar. 3, 2020.
Kawamata et al., "Development of Genome-Editing techniques that Allele-Selective by CRISPR-Cas9 Activity", Programs and Abstracts of the Annual Meeting of the Molecular Biology Society of Japan, 3P-0595, 2019.
Baker et al., "RAC-tagging: Recombineering and Cas9-assisted targeting for protein tagging and conditional analyses", *Scientific Reports* vol. 6, No. 1 XP055407608, doi: 10.1028/srep25529 (May 2016).
European Search Report for European Application No. 19895355.6 mailed Jul. 19, 2022, 12 pages.
Hwang et al., "Efficient genome editing in zebrafish using a CRISPR-Cas system", *Nature Biotechnology* 31(3):227-229, XP055540933, doi: 10.1038/nbt.2501 (Mar. 2013).
Chinese Office Action for CN 201980091726.1 mailed Jun. 8, 2023, 15 pages.
Xie et al., "sgRNA design for the CRISPR/Cas9 system and evaluation of its off-target effects", *Hereditas* 37(11):1125-1139 (2015).

(Continued)

*Primary Examiner* — Marsha Tsay
(74) *Attorney, Agent, or Firm* — Lathrop GPM LLP; Brian C. Trinque; Lisbeth C. Robinson

(57) ABSTRACT

A production method for a cell in which only one allele is genome-edited includes: a step of introducing, into a cell, (A) at least one selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector that can cause the guide RNA of (a1) or (a2) to be expressed, and (B) at least one selected from the group consisting of a Cas protein and an expression vector that can cause the Cas protein to be expressed.

14 Claims, 22 Drawing Sheets
Specification includes a Sequence Listing.

(56) References Cited

OTHER PUBLICATIONS

Zhou et al., "Development of two chromogenic assays for the target and off-target effects of gene editing nuclease", Basic Science Collection of Full Text Database of Chinese Excellent Master's Thesis, No. 2, A006-691, Feb. 15, 2017.

Japanese Office Action for JP Application No. 2024-147493 mailed Mar. 3, 2026, 8 pages.

Shechner et al., "CRISPR Display: A modular method for locus-specific targeting of long noncoding RNAs and synthetic RNA devices in vivo", *Nature Methods* 12(7):664-670, doi:10.1038/nmeth. 3433 (2015).

Tang et al., "Aptazyme-embedded guide RNAs enable ligand-responsive genome editing and transcriptional activation", *Nature Communications* 8:15939, pp. 1-8, doi: 10.1038/noommst5939/ www.nature.oom/natureoommunioations (2017).

* cited by examiner plasmid:sgRNA-Cas9-Puro(p:RCP)

Tbx3-P2A-AIMS

```
SEQUENCE LISTING

<160> NUMBER OF SEQ ID NOS: 132

<210> SEQ ID NO 1
<211> LENGTH: 9175
<212> TYPE: DNA
<213> ORGANISM: Artificial Sequence
<220> FEATURE:
<223> OTHER INFORMATION: CRISPR all-in-one plasmid

<400> SEQUENCE: 1
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg ggtcttcgag aagacctgtt ttagagctag aaatagcaag ttaaaataag     300
gctagtccgt tatcaacttg aaaaagtggc accgagtcgg tgcttttttg ttttagagct     360
agaaatagca agttaaaata aggctagtcc gtttttagcg cgtgcgccaa ttctgcagac     420
aaatggctct agaggtaccc gttacataac ttacggtaaa tggcccgcct ggctgaccgc     480
ccaacgaccc ccgcccattg acgtcaatag taacgccaat agggactttc cattgacgtc     540
aatgggtgga gtatttacgg taaactgccc acttggcagt acatcaagtg tatcatatgc     600
caagtacgcc ccctattgac gtcaatgacg gtaaatggcc cgcctggcat tgtgcccagt     660
acatgacctt atgggacttt cctacttggc agtacatcta cgtattagtc atcgctatta     720
ccatggtcga ggtgagcccc acgttctgct tcactctccc catctccccc ccctccccac     780
ccccaatttt gtatttattt attttttaat tattttgtgc agcgatgggg gcggggggggg     840 gggggggggcg cgcgccaggc ggggcggggc ggggcgaggg gcggggcggg gcgaggcgga     900
```

```
gaggtgcggc ggcagccaat cagagcggcg cgctccgaaa gtttcctttt atggcgaggc      960
ggcggcggcg gcggccctat aaaaagcgaa gcgcgcggcg ggcgggagtc gctgcgacgc     1020
tgccttcgcc ccgtgccccg ctccgccgcc gcctcgcgcc gcccgccccg gctctgactg     1080
accgcgttac tcccacaggt gagcgggcgg gacggccctt ctcctccggg ctgtaattag     1140
ctgagcaaga ggtaagggtt taagggatgg ttggttggtg gggtattaat gtttaattac     1200
ctggagcacc tgcctgaaat cacttttttt caggttggac cggtgccacc atggactata     1260
aggaccacga cggagactac aaggatcatg atattgatta caaagacgat gacgataaga     1320
tggccccaaa gaagaagcgg aaggtcggta tccacggagt cccagcagcc gacaagaagt     1380
acagcatcgg cctggacatc ggcaccaact ctgtgggctg ggccgtgatc accgacgagt     1440
acaaggtgcc cagcaagaaa ttcaaggtgc tgggcaacac cgaccggcac agcatcaaga     1500
agaacctgat cggagccctg ctgttcgaca gcggcgaaac agccgaggcc acccggctga     1560
agagaaccgc cagaagaaga tacaccgacg gaagaaccg gatctgctat ctgcaagaga     1620
tcttcagcaa cgagatggcc aaggtggacg acagcttctt ccacagactg gaagagtcct     1680
tcctggtgga agaggataag aagcacgagc ggcaccccat cttcggcaac atcgtggacg     1740
aggtggccta ccacgagaag tacccccacca tctaccacct gagaaagaaa ctggtggaca     1800
gcaccgacaa ggccgacctg cggctgatct atctggccct ggcccacatg atcaagttcc     1860
ggggccactt cctgatcgag ggcgacctga accccgacaa cagcgacgtg gacaagctgt     1920
tcatccagct ggtgcagacc tacaaccagc tgttcgagga aaaccccatc aacgccagcg     1980
gcgtggacgc caaggccatc ctgtctgcca gactgagcaa gagcagacgg ctggaaaatc     2040
tgatcgccca gctgcccggc gagaagaaga tggcctgtt cggaaacctg attgccctga     2100
gcctgggcct gacccccaac ttcaagagca acttcgacct ggccgaggat gccaaactgc     2160
agctgagcaa ggacacctac gacgacgacc tggacaacct gctggcccag atcggcgacc     2220
agtacgccga cctgtttctg gccgccaaga acctgtccga cgccatcctg ctgagcgaca     2280
tcctgagagt gaacaccgag atcaccaagg ccccccctgag cgcctctatg atcaagagat     2340
acgacgagca ccaccaggac ctgaccctgc tgaaagctct cgtgcggcag cagctgcctg     2400
agaagtacaa agagattttc ttcgaccaga gcaagaacgg ctacgccggc tacattgacg     2460
gcggagccag ccaggaagag ttctacaagt tcatcaagcc catcctggaa aagatggacg     2520
gcaccgagga actgctcgtg aagctgaaca gagaggacct gctgcggaag cagcggacct     2580
tcgacaacgg cagcatcccc caccagatcc acctgggaga gctgcacgcc attctgcggc     2640
ggcaggaaga tttttaccca ttcctgaagg acaaccggga aaagatcgag aagatcctga     2700
ccttccgcat cccctactac gtgggccctc tggccagggg aaacagcaga ttcgcctgga     2760
tgaccagaaa gagcgaggaa accatcaccc cctggaactt cgaggaagtg gtggacaagg     2820
gcgcttccgc ccagagcttc atcgagcgga tgaccaactt cgataagaac ctgcccaacg     2880
agaaggtgct gcccaagcac agcctgctgt acgagtactt caccgtgtat aacgagctga     2940
ccaaagtgaa atacgtgacc gagggaatga gaaagcccgc cttcctgagc ggcgagcaga     3000
aaaaggccat cgtggacctg ctgttcaaga ccaaccggaa agtgaccgtg aagcagctga     3060
aagaggacta cttcaagaaa atcgagtgct cgactccgt ggaaatctcc ggcgtggaag     3120
atcggttcaa cgcctccctg ggcacatacc acgatctgct gaaaattatc aaggacaagg     3180
acttcctgga caatgaggaa aacgaggaca ttctggaaga tatcgtgctg accctgacac     3240
```

```
tgtttgagga cagagagatg atcgaggaac ggctgaaaac ctatgcccac ctgttcgacg   3300
acaaagtgat gaagcagctg aagcggcgga gatacaccgg ctggggcagg ctgagccgga   3360
agctgatcaa cggcatccgg gacaagcagt ccggcaagac aatcctggat ttcctgaagt   3420
ccgacggctt cgccaacaga aacttcatgc agctgatcca cgacgacagc ctgaccttta   3480
aagaggacat ccagaaagcc caggtgtccg gccagggcga tagcctgcac gagcacattg   3540
ccaatctggc cggcagcccc gccattaaga agggcatcct gcagacagtg aaggtggtgg   3600
acgagctcgt gaaagtgatg ggccggcaca agcccgagaa catcgtgatc gaaatggcca   3660
gagagaacca gaccacccag aagggacaga agaacagccg cgagagaatg aagcggatcg   3720
aagagggcat caaagagctg ggcagccaga tcctgaaaga acaccccgtg gaaaacaccc   3780
agctgcagaa cgagaagctg tacctgtact acctgcagaa tgggcgggat atgtacgtgg   3840
accaggaact ggacatcaac cggctgtccg actacgatgt ggaccatatc gtgcctcaga   3900
gctttctgaa ggacgactcc atcgacaaca aggtgctgac cagaagcgac aagaaccggg   3960
gcaagagcga caacgtgccc tccgaagagg tcgtgaagaa gatgaagaac tactggcggc   4020
agctgctgaa cgccaagctg attacccaga gaaagttcga caatctgacc aaggccgaga   4080
gaggcggcct gagcgaactg gataaggccg gcttcatcaa gagacagctg gtggaaaccc   4140
ggcagatcac aaagcacgtg gcacagatcc tggactcccg gatgaacact aagtacgacg   4200
agaatgacaa gctgatccgg gaagtgaaag tgatcaccct gaagtccaag ctggtgtccg   4260
atttccggaa ggatttccag ttttacaaag tgcgcgagat caacaactac caccacgccc   4320
acgacgccta cctgaacgcc gtcgtgggaa ccgccctgat caaaaagtac cctaagctgg   4380
aaagcgagtt cgtgtacggc gactacaagg tgtacgacgt gcggaagatg atcgccaaga   4440
gcgagcagga aatcggcaag gctaccgcca agtacttctt ctacagcaac atcatgaact   4500
ttttcaagac cgagattacc ctggccaacg gcgagatccg gaagcggcct ctgatcgaga   4560
caaacggcga aaccggggag atcgtgtggg ataagggccg ggattttgcc accgtgcgga   4620
aagtgctgag catgccccaa gtgaatatcg tgaaaaagac cgaggtgcag acaggcggct   4680
tcagcaaaga gtctatcctg cccaagagga acagcgataa gctgatcgcc agaaagaagg   4740
actgggaccc taagaagtac ggcggcttcg acagccccac cgtggcctat tctgtgctgg   4800
tggtggccaa agtggaaaag ggcaagtcca agaaactgaa gagtgtgaaa gagctgctgg   4860
ggatcaccat catggaaaga agcagcttcg agaagaatcc catcgacttt ctggaagcca   4920
agggctacaa agaagtgaaa aaggacctga tcatcaagct gcctaagtac tccctgttcg   4980
agctggaaaa cggccggaag agaatgctgg cctctgccgg cgaactgcag aagggaaacg   5040
aactggccct gccctccaaa tatgtgaact tcctgtacct ggccagccac tatgagaagc   5100
tgaagggctc ccccgaggat aatgagcaga aacagctgtt tgtggaacag cacaagcact   5160
acctggacga gatcatcgag cagatcagcg agttctccaa gagagtgatc ctggccgacg   5220
ctaatctgga caaagtgctg tccgcctaca acaagcaccg ggataagccc atcagagagc   5280
aggccgagaa tatcatccac ctgtttaccc tgaccaatct gggagcccct gccgccttca   5340
agtactttga caccaccatc gaccggaaga ggtacaccag caccaaagag gtgctggacg   5400
ccaccctgat ccaccagagc atcaccggcc tgtacgagac acggatcgac ctgtctcagc   5460
tgggaggcga caaaaggccg gcggccacga aaaaggccgg ccaggcaaaa agaaaaaagg   5520
aattcggcag tggagagggc agaggaagtc tgctaacatg cggtgacgtc gaggagaatc   5580
ctggcccaat gaccgagtac aagcccacgg tgcgcctcgc cacccgcgac gacgtcccca   5640
```

-continued

```
gggccgtacg caccctcgcc gccgcgttcg ccgactaccc cgccacgcgc cacaccgtcg      5700
atccggaccg ccacatcgag cgggtcaccg agctgcaaga actcttcctc acgcgcgtcg      5760
ggctcgacat cggcaaggtg tgggtcgcgg acgacggcgc cgcggtggcg gtctggacca      5820
cgccggagag cgtcgaagcg ggggcggtgt tcgccgagat cggcccgcgc atggccgagt      5880
tgagcggttc ccggctggcc gcgcagcaac agatggaagg cctcctggcg ccgcaccggc      5940
ccaaggagcc cgcgtggttc ctggccaccg tcggagtctc gcccgaccac cagggcaagg      6000
gtctgggcag cgccgtcgtg ctccccggag tggaggcggc cgagcgcgcc ggggtgcccg      6060
ccttcctgga gacctccgcg ccccgcaacc tccccttcta cgagcggctc ggcttcaccg      6120
tcaccgccga cgtcgaggtg cccgaaggac cgcgcacctg gtgcatgacc cgcaagcccg      6180
gtgcctgaga attctaacta gagctcgctg atcagcctcg actgtgcctt ctagttgcca      6240
gccatctgtt gtttgcccct cccccgtgcc ttccttgacc ctggaaggtg ccactcccac      6300
tgtcctttcc taataaaatg aggaaattgc atcgcattgt ctgagtaggt gtcattctat      6360
tctggggggt ggggtggggc aggacagcaa gggggaggat tgggaagaga atagcaggca      6420
tgctggggag cggccgcagg aacccctagt gatggagttg gccactccct ctctgcgcgc      6480
tcgctcgctc actgaggccg ggcgaccaaa ggtcgcccga cgcccgggct ttgcccgggc      6540
ggcctcagtg agcgagcgag cgcgcagctg cctgcagggg cgcctgatgc ggtattttct      6600
ccttacgcat ctgtgcggta tttcacaccg catacgtcaa agcaaccata gtacgcgccc      6660
tgtagcggcg cattaagcgc ggcgggtgtg gtggttacgc gcagcgtgac cgctacactt      6720
gccagcgccc tagcgcccgc tcctttcgct ttcttccctt cctttctcgc cacgttcgcc      6780
ggctttcccc gtcaagctct aaatcggggg ctccctttag ggttccgatt tagtgcttta      6840
cggcacctcg accccaaaaa acttgatttg ggtgatggtt cacgtagtgg gccatcgccc      6900
tgatagacgg ttttttcgcc ctttgacgttg gagtccacgt tctttaatag tggactcttg      6960
ttccaaactg gaacaacact caaccctatc tcgggctatt cttttgattt ataagggatt      7020
ttgccgattt cggcctattg gttaaaaaat gagctgattt aacaaaaatt taacgcgaat      7080
tttaacaaaa tattaacgtt tacaattttta tggtgcactc tcagtacaat ctgctctgat      7140
gccgcatagt taagccagcc ccgacacccg ccaacacccg ctgacgcgcc ctgacgggct      7200
tgtctgctcc cggcatccgc ttacagacaa gctgtgaccg tctccgggag ctgcatgtgt      7260
cagaggtttt caccgtcatc accgaaacgc gcgagacgaa agggcctcgt gatacgccta      7320 ttttttatagg ttaatgtcat gataataatg gtttcttaga cgtcaggtgg cacttttcgg      7380
ggaaatgtgc gcggaacccc tatttgttta ttttttctaaa tacattcaaa tatgtatccg      7440
ctcatgagac aataaccctg ataaatgctt caataatatt gaaaaaggaa gagtatgagt      7500
attcaacatt tccgtgtcgc ccttattccc ttttttgcgg catttttgcct tcctgttttt      7560 gctcacccag aaacgctggt gaaagtaaaa gatgctgaag atcagttggg tgcacgagtg      7620
ggttacatcg aactggatct caacagcggt aagatccttg agagttttcg ccccgaagaa      7680
cgttttccaa tgatgagcac ttttaaagtt ctgctatgtg gcgcggtatt atcccgtatt      7740
gacgccgggc aagagcaact cggtcgccgc atacactatt ctcagaatga cttggttgag      7800
tactcaccag tcacagaaaa gcatcttacg gatggcatga cagtaagaga attatgcagt      7860
gctgccataa ccatgagtga taacactgcg gccaacttac ttctgacaac gatcggagga      7920
ccgaaggagc taaccgcttt tttgcacaac atgggggatc atgtaactcg ccttgatcgt      7980
```

-continued tgggaaccgg agctgaatga agccatacca aacgacgagc gtgacaccac gatgcctgta          8040
gcaatggcaa caacgttgcg caaactatta actggcgaac tacttactct agcttcccgg          8100
caacaattaa tagactggat ggaggcggat aaagttgcag gaccacttct gcgctcggcc          8160
cttccggctg gctggtttat tgctgataaa tctggagccg gtgagcgtgg aagccgcggt          8220
atcattgcag cactggggcc agatggtaag ccctcccgta tcgtagttat ctacacgacg          8280
gggagtcagg caactatgga tgaacgaaat agacagatcg ctgagatagg tgcctcactg          8340
attaagcatt ggtaactgtc agaccaagtt tactcatata tactttagat tgatttaaaa          8400
cttcattttt aatttaaaag gatctaggtg aagatccttt ttgataatct catgaccaaa          8460
atcccttaac gtgagttttc gttccactga gcgtcagacc ccgtagaaaa gatcaaagga          8520
tcttcttgag atcctttttt tctgcgcgta atctgctgct tgcaaacaaa aaaaccaccg          8580
ctaccagcgg tggtttgttt gccggatcaa gagctaccaa ctctttttcc gaaggtaact          8640
ggcttcagca gagcgcagat accaaatact gtccttctag tgtagccgta gttaggccac          8700
cacttcaaga actctgtagc accgcctaca tacctcgctc tgctaatcct gttaccagtg          8760
gctgctgcca gtggcgataa gtcgtgtctt accgggttgg actcaagacg atagttaccg          8820
gataaggcgc agcggtcggg ctgaacgggg ggttcgtgca cacagcccag cttggagcga          8880
acgacctaca ccgaactgag atacctacag cgtgagctat gagaaagcgc cacgcttccc          8940
gaagggagaa aggcggacag gtatccggta agcggcaggg tcggaacagg agagcgcacg          9000
agggagcttc caggggggaaa cgcctggtat ctttatagtc ctgtcgggtt tcgccacctc          9060
tgacttgagc gtcgattttt gtgatgctcg tcaggggggc ggagcctatg gaaaaacgcc          9120
agcaacgcgg cctttttacg gttcctggcc ttttgctggc cttttgctca catgt             9175

<210> SEQ ID NO 2
<211> LENGTH: 2744
<212> TYPE: DNA
<213> ORGANISM: Artificial Sequence
<220> FEATURE:
<223> OTHER INFORMATION: sgRNA expression vector

<400> SEQUENCE: 2
ggccgcagga accctagtg atggagttgg ccactccctc tctgcgcgct cgctcgctca          60
ctgaggccgg gcgaccaaag gtcgcccgac gcccgggctt gcccgggcg gcctcagtga          120 gcgagcgagc gcgcagctgc ctgcagggggc gcctgatgcg gtattttctc cttacgcatc          180
tgtgcggtat ttcacaccgc atacgtcaaa gcaaccatag tacgcgccct gtagcggcgc          240
attaagcgcg gcgggtgtgg tggttacgcg cagcgtgacc gctacacttg ccagcgccct          300
agcgcccgct cctttcgctt tcttcccttc ctttctcgcc acgttcgccg gctttccccg          360
tcaagctcta atcggggggc tccctttagg gttccgattt agtgctttac ggcacctcga          420
ccccaaaaaa cttgatttgg gtgatggttc acgtagtggg ccatcgccct gatagacggt          480
ttttcgccct ttgacgttgg agtccacgtt ctttaatagt ggactcttgt tccaaactgg          540
aacaacactc aaccctatct cgggctattc ttttgattta aagggattt tgccgatttc          600 ggcctattgg ttaaaaaatg agctgattta acaaaaattt aacgcgaatt ttaacaaaat          660
attaacgttt acaattttat ggtgcactct cagtacaatc tgctctgatg ccgcatagtt          720
aagccagccc cgacacccgc caacacccgc tgacgcgccc tgacgggctt gtctgctccc          780
ggcatccgct tacagacaag ctgtgaccgt ctccgggagc tgcatgtgtc agaggttttc          840
accgtcatca ccgaaacgcg cgagacgaaa gggcctcgtg atacgcctat ttttataggt          900

-continued

```
taatgtcatg ataataatgg tttcttagac gtcaggtggc acttttcggg gaaatgtgcg      960
cggaacccct atttgtttat ttttctaaat acattcaaat atgtatccgc tcatgagaca     1020
ataaccctga taaatgcttc aataatattg aaaaaggaag agtatgagta ttcaacattt     1080
ccgtgtcgcc cttattccct ttttttgcggc attttgcctt cctgtttttg ctcacccaga     1140
aacgctggtg aaagtaaaag atgctgaaga tcagttgggt gcacgagtgg gttacatcga     1200
actggatctc aacagcggta agatccttga gagttttcgc cccgaagaac gttttccaat     1260
gatgagcact tttaaagttc tgctatgtgg cgcggtatta tcccgtattg acgccgggca     1320
agagcaactc ggtcgccgca tacactattc tcagaatgac ttggttgagt actcaccagt     1380
cacagaaaag catcttacgg atggcatgac agtaagagaa ttatgcagtg ctgccataac     1440
catgagtgat aacactgcgg ccaacttact tctgacaacg atcggaggac cgaaggagct     1500
aaccgctttt ttgcacaaca tgggggatca tgtaactcgc cttgatcgtt gggaaccgga     1560
gctgaatgaa gccataccaa acgacgagcg tgacaccacg atgcctgtag caatggcaac     1620
aacgttgcgc aaactattaa ctggcgaact acttactcta gcttcccggc aacaattaat     1680
agactggatg gaggcggata aagttgcagg accacttctg cgctcggccc ttccggctgg     1740
ctggtttatt gctgataaat ctggagccgg tgagcgtgga agccgcggta tcattgcagc     1800
actggggcca gatggtaagc cctcccgtat cgtagttatc tacacgacgg ggagtcaggc     1860
aactatggat gaacgaaata gacagatcgc tgagataggt gcctcactga ttaagcattg     1920
gtaactgtca gaccaagttt actcatatat actttagatt gatttaaaac ttcattttta     1980
atttaaaagg atctaggtga agatcctttt tgataatctc atgaccaaaa tcccttaacg     2040
tgagttttcg ttccactgag cgtcagaccc cgtagaaaag atcaaaggat cttcttgaga     2100 tcctttttttt ctgcgcgtaa tctgctgctt gcaaacaaaa aaaccaccgc taccagcggt     2160
ggtttgtttg ccggatcaag agctaccaac tcttttttccg aaggtaactg gcttcagcag     2220
agcgcagata ccaaatactg tccttctagt gtagccgtag ttaggccacc acttcaagaa     2280
ctctgtagca ccgcctacat acctcgctct gctaatcctg ttaccagtgg ctgctgccag     2340
tggcgataag tcgtgtctta ccgggttgga ctcaagacga tagttaccgg ataaggcgca     2400
gcggtcgggc tgaacggggg gttcgtgcac acagcccagc ttggagcgaa cgacctacac     2460
cgaactgaga tacctacagc gtgagctatg agaaagcgcc acgcttcccg aagggagaaa     2520
ggcggacagg tatccggtaa gcggcagggt cggaacagga gagcgcacga gggagcttcc     2580
agggggaaac gcctggtatc tttatagtcc tgtcgggttt cgccacctct gacttgagcg     2640
tcgatttttg tgatgctcgt caggggggcg gagcctatgg aaaaacgcca gcaacgcggc     2700
ctttttacgg ttcctggcct tttgctggcc ttttgctcac atgt                     2744
```

<210> SEQ ID NO 3
<211> LENGTH: 2804
<212> TYPE: DNA
<213> ORGANISM: Artificial Sequence
<220> FEATURE:
<223> OTHER INFORMATION: Tbx3-P2A-tdTomato KI vector without backbone
      T-easy vector sequence

<400> SEQUENCE: 3

```
gttccccact ctctaactcc ctatgtttct tctctctctt ccccagggct tggctatgtc       60
gcctttcggg agcctgtttc cttaccccta cacatacatg gctgcagcag ctgcagcctc      120
caccgcggcc gcctccagct ccgtgcaccg ccacccgttc ctcaatttga acagcatgcg      180
```

-continued

```
ccccaggctg cgttacagcc cctattccat ccccgtccca gtgccggata gcagcagttt      240
gctggccaca gctttaccat caatggcttc cgccgcgggg cccctagacg gcaaagcggc      300
cgccctggca gccagcccag cctcggtggc tgtggactcg gggtcggaac tgaacagccg      360
ctcgtccacg ctgtcctctg gctcagtgtc cttgtcaccc aaactctgct ccgagaagga      420
ggcggctacc agcgaactgc agagtatcca gcggctggtc agtggcttgg aagccaagcc      480
agacaggtct tgcagcgggt ccccttatgg taccggaagc ggagctacta acttcagcct      540
gctgaagcag gctggagacg tggaggagaa ccctggacct atggtgagca agggcgagga      600
ggtcatcaaa gagttcatgc gcttcaaggt gcgcatggag ggctccatga acggccacga      660
gttcgagatc gagggcgagg gcgagggccg cccctacgag ggcacccaga ccgccaagct      720
gaaggtgacc aagggcggcc ccctgccctt cgcctggac atcctgtccc cccagttcat      780
gtacggctcc aaggcgtacg tgaagcaccc cgccgacatc cccgattaca agaagctgtc      840
cttccccgag ggcttcaagt gggagcgcgt gatgaacttc gaggacggcg gtctggtgac      900
cgtgacccag gactcctccc tgcaggacgg cacgctgatc tacaaggtga agatgcgcgg      960
caccaacttc ccccccgacg gccccgtaat gcagaagaag accatgggct gggaggcctc     1020
caccgagcgc ctgtaccccc gcgacggcgt gctgaagggc gagatccacc aggccctgaa     1080
gctgaaggac ggcggccgct acctggtgga gttcaagacc atctacatgg ccaagaagcc     1140
cgtgcaactg cccggctact actacgtgga caccaagctg gacatcacct cccacaacga     1200
ggactacacc atcgtggaac agtacgagcg ctccgagggc cgccaccacc tgttcctggg     1260
gcatggcacc ggcagcaccg gcagcggcag ctccggcacc gcctcctccg aggacaacaa     1320
catggccgtc atcaaagagt tcatgcgctt caaggtgcgc atggaggct ccatgaacgg     1380 ccacgagttc gagatcgagg gcgagggcga gggccgcccc tacgagggca cccagaccgc     1440
caagctgaag gtgaccaagg gcggcccct gcccttcgcc tgggacatcc tgtccccca     1500 gttcatgtac ggctccaagg cgtacgtgaa gcaccccgcc gacatccccg attacaagaa     1560
gctgtccttc cccgagggct tcaagtggga gcgcgtgatg aacttcgagg acggcggtct     1620
ggtgaccgtg acccaggact cctccctgca ggacggcacg ctgatctaca ggtgaagat     1680 gcgcggcacc aacttcccc ccgacggccc cgtaatgcag aagaagacca tgggctggga     1740
ggcctccacc gagcgcctgt accccgcga cggcgtgctg aagggcgaga tccaccaggc     1800
cctgaagctg aaggacggcg gccactacct ggtggagttc aagaccatct acatggccaa     1860
gaagcccgtg caactgcccg ctactacta cgtggacacc aagctggaca tcacctccca     1920
caacgaggac tacaccatcg tggaacagta cgagcgctcc gagggccgcc accacctgtt     1980
cctgtacggc atggacgagc tgtacaagta aaagcttggc cgccatggcc caacgtcgac     2040
ctgccagtgc actttgttag atgtaaaata aaccacgggc cttccacatg gggtgacccc     2100
cgccctgtcc ctttcagttt tgtctgggag ggagcactaa agcctttcca gagactatgc     2160
tagataccac aggccctgcc accatgggct gtgtaaccag gctgctgttg ctttgaaacg     2220
cgggactgag ggggcgggag gagtggtggc aaacaggctt ttgtgtctag agcgactttt     2280
gtgcaggctg gtatggaagt cggggctgaa gaacaaggta gccaggccag ccaggagcgc     2340
gggtctttga gagacttcac cggaatcttt ccccttcgt gtgtttagtg gaaacatccc     2400
ccctcctaaa caaactaaca aaaccaatat ggaggtgggg ggagatgaag tcctgtggaa     2460
ctgtctatga agactgaaac tcaccaattg ctgagtactt tcgttggggc agagagaaga     2520
```
ggggccttac cttgccccat ctatattaaa ggaatcctgt ctttttttgt ttgtttgttt    2580
ttaaatattg tgatgtttta agagccgatg ctggcttctt ttttgcatgt tacagttttc    2640
tgggtttatt ttgcccccc cccctttat ggaaaaacaa cggaagtccc attatcctca    2700
accttgctca aggcggcaac caggaggaag tggggtaaaa ggggcagcta tgggcatgaa    2760
accaaccgag ttgatttta tctgagcgct tgtagaggat gcat    2804

<210> SEQ ID NO 4
<211> LENGTH: 2070
<212> TYPE: DNA
<213> ORGANISM: Artificial Sequence
<220> FEATURE:
<223> OTHER INFORMATION: Tbx3-P2A-Venus KI vector without backbone
     T-easy vector sequence

<400> SEQUENCE: 4
gttccccact ctctaactcc ctatgtttct tctctctctt ccccagggct tggctatgtc     60
gcctttcggg agcctgtttc cttaccccta cacatacatg gctgcagcag ctgcagcctc    120
caccgcggcc gcctccagct ccgtgcaccg ccacccgttc ctcaatttga acagcatgcg    180
ccccaggctg cgttacagcc cctattccat ccccgtccca gtgccggata gcagcagttt    240
gctggccaca gctttaccat caatggcttc cgccgcgggg cccctagacg gcaaagcggc    300
cgccctggca gccagcccag cctcggtggc tgtggactcg gggtcggaac tgaacagccg    360
ctcgtccacg ctgtcctctg gctcagtgtc cttgtcaccc aaactctgct ccgagaagga    420
ggcggctacc agcgaactgc agagtatcca gcggctggtc agtggcttgg aagccaagcc    480
agacaggtct tgcagcgggt ccccttatgg taccggaagc ggagctacta acttcagcct    540
gctgaagcag gctggagacg tggaggagaa ccctggacct atggtgagca agggcgagga    600
gctgttcacc ggggtggtgc ccatcctggt cgagctggac ggcgacgtaa acggccacaa    660
gttcagcgtg tccggcgagg gcgagggcga tgccacctac ggcaagctga ccctgaagct    720
gatctgcacc accggcaagc tgcccgtgcc ctggcccacc ctcgtgacca ccctgggcta    780
cggcctgcag tgcttcgccc gctaccccga ccacatgaag cagcacgact tcttcaagtc    840
cgccatgccc gaaggctacg tccaggagcg caccatcttc ttcaaggacg acggcaacta    900
caagacccgc gccgaggtga agttcgaggg cgacaccctg gtgaaccgca tcgagctgaa    960
gggcatcgac ttcaaggagg acggcaacat cctggggcac aagctggagt acaactacaa    1020
cagccacaac gtctatatca ccgccgacaa gcagaagaac ggcatcaagg ccaacttcaa    1080
gatccgccac aacatcgagg acggcggcgt gcagctcgcc gaccactacc agcagaacac    1140
ccccatcggc gacggccccg tgctgctgcc cgacaaccac tacctgagct accagtccaa    1200
gctgagcaaa gaccccaacg agaagcgcga tcacatggtc ctgctggagt tcgtgaccgc    1260
cgccgggatc actctcggca tggacgagct gtacaagtaa gtcgacctgc cagtgcactt    1320
tgttagatgt aaaataaacc acgggccttc cacatgggt gaccccgccc ctgtcccttt    1380
cagttttgtc tgggagggag cactaaagcc tttccagaga ctatgctaga taccacaggc    1440
cctgccacca tgggctgtgt aaccaggctg ctgttgcttt gaaacgcggg actgaggggg    1500
cgggaggagt ggtggcaaac aggcttttgt gtctagagcg acttttgtgc aggctggtat    1560
ggaagtcggg gctgaagaac aaggtagcca ggccagccag gagcgcgggt ctttgagaga    1620
cttcaccgga atctttcccc cttcgtgtgt ttagtggaaa catcccccct cctaaacaaa    1680
ctaacaaaac caatatggag gtggggggag atgaagtcct gtggaactgt ctatgaagac    1740

-continued

```
tgaaactcac caattgctga gtactttcgt tggggcagag agaagagggg ccttaccttg   1800
ccccatctat attaaaggaa tcctgtcttt ttttgtttgt ttgttttttaa atattgtgat   1860 gttttaagag ccgatgctgg cttctttttt gcatgttaca gttttctggg tttattttgc   1920 ccccccccc ttttatggaa aaacaacgga agtcccatta tcctcaacct tgctcaaggc   1980
ggcaaccagg aggaagtggg gtaaaagggg cagctatggg catgaaacca accgagttga   2040
tttttatctg agcgcttgta gaggatgcat                                    2070
```

```
<210> SEQ ID NO 5
<211> LENGTH: 2498
<212> TYPE: DNA
<213> ORGANISM: Artificial Sequence
<220> FEATURE:
<223> OTHER INFORMATION: Cdh1-P2A-tdTomato KI vector without backbone
      T-easy vector sequence

<400> SEQUENCE: 5
ccgcggctga ttcccccaac ttcagaatta acatttaaca atagcagttt gtcatctgtc     60
cttcgaggat tttctgggct gaactgtaac ctacgtgttt tagtatgacg actctcgttg    120
ctcttaccct ctgtccagcc tggccttggg actttgcctt ctgtgctggt gtgtgtgtgt    180
gtgtgtgtgt gtgtgtgtgt accttgaagg ggttaactac tccttggtta gttttttcatg   240 tttggggtgt tgcttgcctc tgatgcatac tgataagtac ggtgctcttc cttttagaac    300
ctgaaggcag ccgacagcga ccccacggca cccccttacg actctctgtt ggtgttcgat    360
tacgagggca gtggttctga agccgctagc ctgagctcac tgaactcctc tgagtcggat    420
caggaccagg actacgatta tctgaacgag tggggcaacc gattcaagaa gctggcggac    480
atgtacggcg gtggtgagga cgacggtacc ggaagcggag ctactaactt cagcctgctg    540
aagcaggctg gagacgtgga ggagaaccct ggacctatgg tgagcaaggg cgaggaggtc    600
atcaaagagt tcatgcgctt caaggtgcgc atggagggct ccatgaacgg ccacgagttc    660
gagatcgagg gcgagggcga gggccgcccc tacgagggca cccagaccgc caagctgaag    720
gtgaccaagg gcggcccct gcccttcgcc tgggacatcc tgtcccccca gttcatgtac    780
ggctccaagg cgtacgtgaa gcaccccgcc gacatccccg attacaagaa gctgtccttc    840
cccgagggct tcaagtggga gcgcgtgatg aacttcgagg acggcggtct ggtgaccgtg    900
acccaggact cctccctgca ggacggcacg ctgatctaca aggtgaagat gcgcggcacc    960
aacttccccc ccgacggccc cgtaatgcag aagaagacca tgggctggga ggcctccacc   1020
gagcgcctgt accccgcga cggcgtgctg aagggcgaga tccaccaggc cctgaagctg   1080
aaggacggcg gccgctacct ggtggagttc aagaccatct acatggccaa gaagcccgtg   1140
caactgcccg gctactacta cgtggacacc aagctggaca tcacctccca caacgaggac   1200
tacaccatcg tggaacagta cgagcgctcc gagggccgcc accacctgtt cctggggcat   1260
ggcaccggca gcaccggcag cggcagctcc ggcaccgcct cctccgagga caacaacatg   1320
gccgtcatca agagttcat gcgcttcaag gtgcgcatgg agggctccat gaacggccac   1380
gagttcgaga tcgagggcga gggcgagggc cgcccctacg agggcaccca gaccgccaag   1440
ctgaaggtga ccaagggcgg cccctgccc ttcgcctggg acatcctgtc cccccagttc   1500
atgtacggct ccaaggcgta cgtgaagcac cccgccgaca tccccgatta caagaagctg   1560
tccttccccg agggcttcaa gtgggagcgc gtgatgaact cgaggacgg cggtctggtg   1620 accgtgaccc aggactcctc cctgcaggac ggcacgctga tctacaaggt gaagatgcgc   1680
```

-continued

```
ggcaccaact tccccccga cggccccgta atgcagaaga agaccatggg ctgggaggcc    1740
tccaccgagc gcctgtaccc ccgcgacggc gtgctgaagg gcgagatcca ccaggccctg    1800
aagctgaagg acggcggcca ctacctggtg gagttcaaga ccatctacat ggccaagaag    1860
cccgtgcaac tgcccggcta ctactacgtg gacaccaagc tggacatcac ctcccacaac    1920
gaggactaca ccatcgtgga acagtacgag cgctccgagg gccgccacca cctgttcctg    1980
tacggcatgg acgagctgta caagtaaagc ttggccgcca tggcccaacg tcgaccgtgt    2040
ggcaccatgg gagatgcaga ataattatat cagtggtctt tcagctcctt ccctgagtgt    2100
gtagaagaga gactgatctg agaagtgtgc agattgcata gtggtctcac tctccctact    2160
ggactgtctg tgttaggatg gttttcactg attgttgaaa tcttttttta ttttttattt    2220
ttacagtgct gagatataaa ctgtgccttt ttttgtttgt ttgtttctgt ttttgttctt    2280
ttgagctatg atctgcccca gacacaacag ccccaagccc ctcacacctc actaattttt    2340
tacattgtgt acttgccctc aattaccatg tttgctgtat tctaatagtc actcatgttc    2400
ctgaattctg ttgccctgcc caggtgatat tctaggatgc agaaatgcct gggccctttt    2460
atggtgagag acaggtatct tggtgtgggt gcgtcgac                          2498
```

<210> SEQ ID NO 6
<211> LENGTH: 1594
<212> TYPE: DNA
<213> ORGANISM: Artificial Sequence
<220> FEATURE:
<223> OTHER INFORMATION: Cdh1-P2A-Venus KI vector without backbone
       T-easy vector sequence

<400> SEQUENCE: 6

```
ccgcggctga ttcccccaac ttcagaatta acatttaaca atagcagttt gtcatctgtc      60
cttcgaggat tttctgggct gaactgtaac ctacgtgttt tagtatgacg actctcgttg     120
ctcttaccct ctgtccagcc tggccttggg actttgcctt ctgtgctggt gtgtgtgtgt     180
gtgtgtgtgt gtgtgtgtgt accttgaagg ggttaactac tccttggtta gttttttcatg     240 tttgggtgt tgcttgcctc tgatgcatac tgataagtac ggtgctcttc cttttagaac      300
ctgaaggcag ccgacagcga ccccacggca cccccttacg actctctgtt ggtgttcgat     360
tacgagggca gtggttctga agccgctagc ctgagctcac tgaactcctc tgagtcggat     420
caggaccagg actacgatta tctgaacgag tggggcaacc gattcaagaa gctggcggac     480
atgtacggcg gtggtgagga cgacggtacc ggaagcggag ctactaactt cagcctgctg     540
aagcaggctg agacgtgga ggagaaccct ggacctatgg tgagcaaggg cgaggagctg     600
ttcaccgggg tggtgcccat cctggtcgag ctggacggcg acgtaaacgg ccacaagttc     660
agcgtgtccg gcgagggcga gggcgatgcc acctacggca agctgaccct gaagctgatc     720
tgcaccaccg gcaagctgcc cgtgccctgg cccaccctcg tgaccaccct gggctacggc     780
ctgcagtgct tcgcccgcta ccccgaccac atgaagcagc acgacttctt caagtccgcc     840
atgcccgaag gctacgtcca ggagcgcacc atcttcttca aggacgacgg caactacaag     900
acccgcgccg aggtgaagtt cgagggcgac accctggtga accgcatcga gctgaagggc     960
atcgacttca aggaggacgg caacatcctg gggcacaagc tggagtacaa ctacaacagc    1020
cacaacgtct atatcaccgc cgacaagcag aagaacggca tcaaggccaa cttcaagatc    1080
cgccacaaca tcgaggacgg cggcgtgcag ctcgccgacc actaccagca gaacacccc     1140 atcggcgacg gccccgtgct gctgcccgac aaccactacc tgagctacca gtccaagctg    1200
```

-continued

```
agcaaagacc ccaacgagaa gcgcgatcac atggtcctgc tggagttcgt gaccgccgcc    1260
gggatcactc tcggcatgga cgagctgtac aagtaagtcg acgggactag caagtctcca    1320
ccgtgtggca ccatgggaga tgcagaataa ttatatcagt ggtctttcag ctccttccct    1380
gagtgtgtag aagagagact gatctgagaa gtgtgcagat tgcatagtgg tctcactctc    1440
cctactggac tgtctgtgtt aggatggttt tcactgattg ttgaaatctt ttttttattttt   1500 ttatttttac agtgctgaga tataaactgt gccttttttt gtttgtttgt ttctgttttt    1560
gttcttttga gctatgatct gccccagagt cgac                                1594
```

```
<210> SEQ ID NO 7
<211> LENGTH: 2498
<212> TYPE: DNA
<213> ORGANISM: Artificial Sequence
<220> FEATURE:
<223> OTHER INFORMATION: Cdh1-aP2A-tdTomato KI vector without backbone
      T-easy vector sequence

<400> SEQUENCE: 7
```

```
ccgcggctga ttcccccaac ttcagaatta acatttaaca atagcagttt gtcatctgtc      60
cttcgaggat tttctgggct gaactgtaac ctacgtgttt tagtatgacg actctcgttg     120
ctcttaccct ctgtccagcc tggccttggg actttgcctt ctgtgctggt gtgtgtgtgt     180
gtgtgtgtgt gtgtgtgtgt accttgaagg ggttaactac tccttggtta gttttttcatg    240 tttgggggtgt tgcttgcctc tgatgcatac tgataagtac ggtgctcttc cttttagaac     300
ctgaaggcag ccgacagcga ccccacggca cccccttacg actctctgtt ggtgttcgat     360
tacgagggca gtggttctga agccgctagc ctgagctcac tgaactcctc tgagtcggat     420
caggaccagg actacgatta tctgaacgag tggggcaacc gattcaagaa gctggcggac     480
atgtacggcg gtggtgagga cgacggtacc gggagtgggg ccaccaattt tagtctacta     540
aaacaagccg gggatgtaga agaaaatccc gggcccatgg tgagcaaggg cgaggaggtc     600
atcaaagagt tcatgcgctt caaggtgcgc atggagggct ccatgaacgg ccacgagttc     660
gagatcgagg gcgagggcga gggccgcccc tacgagggca cccagaccgc caagctgaag     720
gtgaccaagg gcggccccct gcccttcgcc tgggacatcc tgtcccccca gttcatgtac     780
ggctccaagg cgtacgtgaa gcaccccgcc gacatccccg attacaagaa gctgtccttc     840
cccgagggct tcaagtggga gcgcgtgatg aacttcgagg acggcggtct ggtgaccgtg     900
acccaggact cctccctgca ggacggcacg ctgatctaca aggtgaagat gcgcggcacc     960 aacttcccc ccgacggccc cgtaatgcag aagaagacca tgggctggga ggcctccacc    1020
gagcgcctgt accccgcga cggcgtgctg aagggcgaga tccaccaggc cctgaagctg     1080
aaggacggcg gccgctacct ggtggagttc aagaccatct acatggccaa gaagcccgtg    1140
caactgcccg gctactacta cgtggacacc aagctggaca tcacctccca caacgaggac    1200
tacaccatcg tggaacagta cgagcgctcc gagggccgcc accaccgtt cctggggcat    1260 ggcaccggca gcaccggcag cggcagctcc ggcaccgcct cctccgagga caacaacatg    1320
gccgtcatca aagagttcat gcgcttcaag gtgcgcatgg agggctccat gaacggccac    1380
gagttcgaga tcgagggcga gggcgagggc cgcccctacg agggcaccca gaccgccaag    1440
ctgaaggtga ccaagggcgg ccccctgccc ttcgcctggg acatcctgtc cccccagttc    1500
atgtacggct ccaaggcgta cgtgaagcac ccgccgaca tccccgatta caagaagctg    1560 tccttcccccg agggcttcaa gtgggagcgc gtgatgaact cgaggacgg cggtctggtg    1620
```

-continued

```
accgtgaccc aggactcctc cctgcaggac ggcacgctga tctacaaggt gaagatgcgc   1680
ggcaccaact tcccccccga cggccccgta atgcagaaga agaccatggg ctgggaggcc   1740
tccaccgagc gcctgtaccc ccgcgacggc gtgctgaagg gcgagatcca ccaggccctg   1800
aagctgaagg acggcggcca ctacctggtg gagttcaaga ccatctacat ggccaagaag   1860
cccgtgcaac tgcccggcta ctactacgtg gacaccaagc tggacatcac ctcccacaac   1920
gaggactaca ccatcgtgga acagtacgag cgctccgagg gccgccacca cctgttcctg   1980
tacggcatgg acgagctgta caagtaaagc ttggccgcca tggcccaacg tcgaccgtgt   2040
ggcaccatgg gagatgcaga ataattatat cagtggtctt tcagctcctt ccctgagtgt   2100
gtagaagaga gactgatctg agaagtgtgc agattgcata gtggtctcac tctccctact   2160
ggactgtctg tgttaggatg gttttcactg attgttgaaa tcttttttta ttttttattt   2220
ttacagtgct gagatataaa ctgtgccttt ttttgtttgt ttgtttctgt ttttgttctt   2280
ttgagctatg atctgcccca gacacaacag ccccaagccc ctcacacctc actaatttt   2340 tacattgtgt acttgccctc aattaccatg tttgctgtat tctaatagtc actcatgttc   2400
ctgaattctg ttgccctgcc caggtgatat ctaggatgc agaaatgcct gggcccttt   2460 atggtgagag acaggtatct tggtgtgggt gcgtcgac                          2498
```

```
<210> SEQ ID NO 8
<211> LENGTH: 1594
<212> TYPE: DNA
<213> ORGANISM: Artificial Sequence
<220> FEATURE:
<223> OTHER INFORMATION: Cdh1-aP2A-Venus KI vector without backbone
      T-easy vector sequence

<400> SEQUENCE: 8
```

```
ccgcggctga ttcccccaac ttcagaatta acatttaaca atagcagttt gtcatctgtc     60
cttcgaggat tttctgggct gaactgtaac ctacgtgttt tagtatgacg actctcgttg    120
ctcttaccct ctgtccagcc tggccttggg actttgcctt ctgtgctggt gtgtgtgtgt    180
gtgtgtgtgt gtgtgtgtgt accttgaagg ggttaactac tccttggtta gttttttcatg    240 tttggggtgt tgcttgcctc tgatgcatac tgataagtac ggtgctcttc cttttagaac    300
ctgaaggcag ccgacagcga ccccacggca cccccttacg actctctgtt ggtgttcgat    360
tacgagggca gtggttctga agccgctagc ctgagctcac tgaactcctc tgagtcggat    420
caggaccagg actacgatta tctgaacgag tggggcaacc gattcaagaa gctggcggac    480
atgtacggcg tggtgaggac cgacggtacc gggagtgggg ccaccaattt tagtctacta    540
aaacaagccg gggatgtaga agaaaatccc gggcccatgg tgagcaaggg cgaggagctg    600
ttcaccgggg tggtgcccat cctggtcgag ctggacggcg acgtaaacgg ccacaagttc    660
agcgtgtccg gcgagggcga gggcgatgcc acctacggca agctgaccct gaagctgatc    720
tgcaccaccg gcaagctgcc cgtgccctgg cccaccctcg tgaccaccct gggctacggc    780
ctgcagtgct tcgcccgcta ccccgaccac atgaagcagc acgacttctt caagtccgcc    840
atgcccgaag ctacgtcca ggagcgcacc atcttcttca ggacgacgg caactacaag    900 acccgcgccg aggtgaagtt cgagggcgac accctggtga accgcatcga gctgaagggc    960
atcgacttca aggaggacgg caacatcctg gggcacaagc tggagtacaa ctacaacagc   1020
cacaacgtct atatcaccgc cgacaagcag aagaacggca tcaaggccaa cttcaagatc   1080
cgccacaaca tcgaggacgg cggcgtgcag ctcgccgacc actaccagca gaacacccc   1140
```

-continued

```
atcggcgacg gccccgtgct gctgcccgac aaccactacc tgagctacca gtccaagctg      1200
agcaaagacc ccaacgagaa gcgcgatcac atggtcctgc tggagttcgt gaccgccgcc      1260
gggatcactc tcggcatgga cgagctgtac aagtaagtcg acgggactag caagtctcca      1320
ccgtgtggca ccatgggaga tgcagaataa ttatatcagt ggtcttcag ctccttccct       1380 gagtgtgtag aagagagact gatctgagaa gtgtgcagat tgcatagtgg tctcactctc      1440
cctactggac tgtctgtgtt aggatggttt tcactgattg ttgaaatctt tttttatttt      1500
ttatttttac agtgctgaga tataaactgt gcctttttt gtttgtttgt ttctgtttt        1560 gttcttttga gctatgatct gccccagagt cgac                                  1594
```

```
<210> SEQ ID NO 9
<211> LENGTH: 4269
<212> TYPE: DNA
<213> ORGANISM: Artificial Sequence
<220> FEATURE:
<223> OTHER INFORMATION: hSpCas9 sequence contained in PX459

<400> SEQUENCE: 9
```

```
atggactata aggaccacga cggagactac aaggatcatg atattgatta caaagacgat       60
gacgataaga tggcccccaaa gaagaagcgg aaggtcggta ccacggagt cccagcagcc       120 gacaagaagt acagcatcgg cctggacatc ggcaccaact ctgtgggctg ggccgtgatc       180
accgacgagt acaaggtgcc cagcaagaaa ttcaaggtgc tgggcaacac cgaccggcac       240
agcatcaaga gaaacctgat cggagccctg ctgttcgaca cggcgaaac agccgaggcc        300 acccggctga gagaaccgc cagaagaaga tacaccagac ggaagaaccg gatctgctat        360
ctgcaagaga tcttcagcaa cgagatggcc aaggtggacg acagcttctt ccacagactg       420
gaagagtcct cctggtgga agaggataag aagcacgagc ggcacccat cttcggcaac        480 atcgtggacg aggtggccta ccacgagaag taccccacca tctaccacct gagaaagaaa       540
ctggtggaca gcaccgacaa ggccgacctg cggctgatct atctggccct ggcccacatg       600
atcaagttcc ggggccactt cctgatcgag ggcgacctga accccgacaa cagcgacgtg       660
gacaagctgt tcatccagct ggtgcagacc tacaaccagc tgttcgagga aaaccccatc       720
aacgccagcg gcgtggacgc caaggccatc ctgtctgcca gactgagcaa gagcagacgg       780
ctggaaaatc tgatcgccca gctgcccggc gagaagaaga tggcctgtt cggaaacctg        840 attgccctga gcctgggcct gacccccaac ttcaagagca acttcgacct ggccgaggat       900
gccaaactgc agctgagcaa ggacacctac gacgacgacc tggacaacct gctggcccag       960
atcggcgacc agtacgccga cctgtttctg gccgccaaga acctgtccga cgccatcctg      1020
ctgagcgaca tcctgagagt gaacaccgag atcaccaagg cccccctgag cgcctctatg      1080
atcaagagat acgacgagca ccaccaggac ctgaccctgc tgaaagctct cgtgcggcag      1140
cagctgcctg agaagtacaa agagattttc ttcgaccaga gcaagaacgg ctacgccggc      1200
tacattgacg gcggagccag ccaggaagag ttctacaagt catcaagcc catcctggaa       1260 aagatggacg gcaccgagga actgctcgtg aagctgaaca gagaggacct gctgcggaag      1320
cagcggacct cgacaacgg cagcatcccc caccagatcc acctgggaga gctgcacgcc      1380
attctgcggc ggcaggaaga tttttaccca ttcctgaagg acaaccggga aaagatcgag       1440
aagatcctga ccttccgcat ccctactac gtgggccctc tggccagggg aaacagcaga       1500
ttcgcctgga tgaccagaaa gagcgaggaa accatcaccc cctggaactt cgaggaagtg      1560
gtggacaagg gcgcttccgc ccagagcttc atcgagcgga tgaccaactt cgataagaac       1620
```

```
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg acaagcagt ccggcaagac aatcctggat   2160
ttcctgaagt ccgacggctt cgccaacaga aacttcatgc agctgatcca cgacgacagc   2220 ctgacctta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400 gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga aaagttcga caatctgacc   2820 aaggccgaga gaggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca agtacttctt ctacagcaac   3240
atcatgaact ttttcaagac cgagattacc ctggccaacg gcgagatccg gaagcggcct   3300
ctgatcgaga caaacggcga aaccggggag atcgtgtggg ataagggccg ggattttgcc   3360
accgtgcgga aagtgctgag catgccccaa gtgaatatcg tgaaaaagac cgaggtgcag   3420
acaggcggct tcagcaaaga gtctatcctg cccaagagga acagcgataa gctgatcgcc   3480
agaaagaagg actgggaccc taagaagtac ggcggcttcg acagccccac cgtggcctat   3540
tctgtgctgt ggtggccaa agtggaaaag ggcaagtcca agaaactgaa gagtgtgaaa   3600
gagctgctgg ggatcaccat catggaaaga agcagcttcg agaagaatcc catcgacttt   3660
ctggaagcca agggctacaa agaagtgaaa aaggacctga tcatcaagct gcctaagtac   3720
tccctgttcg agctggaaaa cggccggaag agaatgctgg cctctgccgg cgaactgcag   3780
aagggaaacg aactggccct gcccctccaaa tatgtgaact tcctgtacct ggccagccac   3840
tatgagaagc tgaagggctc ccccgaggat aatgagcaga acagctgtt tgtggaacag   3900 cacaagcact acctggacga gatcatcgag cagatcagcg agttctccaa gagagtgatc   3960
```

```
ctggccgacg ctaatctgga caaagtgctg tccgcctaca acaagcaccg ggataagccc    4020
atcagagagc aggccgagaa tatcatccac ctgtttaccc tgaccaatct gggagccccct    4080 gccgccttca agtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaag                                                              4269

<210> SEQ ID NO 10
<211> LENGTH: 507
<212> TYPE: DNA
<213> ORGANISM: Mus Musculus

<400> SEQUENCE: 10
gttccccact ctctaactcc ctatgtttct tctctctctt ccccagggct tggctatgtc      60
gcctttcggg agcctgtttc cttaccccta cacatacatg gctgcagcag ctgcagcctc     120
caccgcggcc gcctccagct ccgtgcaccg ccacccgttc ctcaatttga acagcatgcg     180
ccccaggctg cgttacagcc cctattccat ccccgtccca gtgccggata gcagcagttt     240
gctggccaca gctttaccat caatggcttc cgccgcgggg cccctagacg gcaaagcggc     300
cgccctggca gccagcccag cctcggtggc tgtggactcg gggtcggaac tgaacagccg     360
ctcgtccacg ctgtcctctg gctcagtgtc cttgtcaccc aaactctgct ccgagaagga     420
ggcggctacc agcgaactgc agagtatcca gcggctggtc agtggcttgg aagccaagcc     480
agacaggtct tgcagcgggt ccccctta                                         507

<210> SEQ ID NO 11
<211> LENGTH: 758
<212> TYPE: DNA
<213> ORGANISM: Mus Musculus

<400> SEQUENCE: 11
ctgccagtgc actttgttag atgtaaaata aaccacgggc cttccacatg gggtgacccc      60
cgccctgtcc ctttcagttt tgtctgggag ggagcactaa agcctttcca gagactatgc     120
tagataccac aggccctgcc accatgggct gtgtaaccag gctgctgttg ctttgaaacg     180
cgggactgag ggggcgggag gagtggtggc aaacaggctt ttgtgtctag agcgactttt     240
gtgcaggctg gtatggaagt cggggctgaa gaacaaggta gccaggccag ccaggagcgc     300
gggtctttga gagacttcac cggaatcttt ccccccttcgt gtgtttagtg gaaacatccc     360
ccctcctaaa caaactaaca aaaccaatat ggaggtgggg ggagatgaag tcctgtggaa     420
ctgtctatga agactgaaac tcaccaattg ctgagtactt tcgttggggc agagagaaga     480
ggggccttac cttgccccat ctatattaaa ggaatcctgt ctttttttgt ttgtttgttt     540
ttaaatattg tgatgtttta agagccgatg ctggcttctt ttttgcatgt tacagttttc     600
tgggtttatt ttgccccccc cccctttat ggaaaaacaa cggaagtccc attatcctca     660
accttgctca aggcggcaac caggaggaag tggggtaaaa ggggcagcta tgggcatgaa     720
accaaccgag ttgattttta tctgagcgct tgtagagg                             758

<210> SEQ ID NO 12
<211> LENGTH: 498
<212> TYPE: DNA
<213> ORGANISM: Mus Musculus

<400> SEQUENCE: 12
```

-continued

```
ctgattcccc caacttcaga attaacattt aacaatagca gtttgtcatc tgtccttcga      60
ggattttctg ggctgaactg taacctacgt gttttagtat gacgactctc gttgctctta     120
ccctctgtcc agcctggcct tgggactttg ccttctgtgc tggtgtgtgt gtgtgtgtgt     180
gtgtgtgtgt gtgtaccttg aaggggttaa ctactccttg gttagttttt catgtttggg     240
gtgttgcttg cctctgatgc atactgataa gtacggtgct cttcctttta gaacctgaag     300
gcagccgaca gcgaccccac ggcacccccct tacgactctc tgttggtgtt cgattacgag    360
ggcagtggtt ctgaagccgc tagcctgagc tcactgaact cctctgagtc ggatcaggac     420
caggactacg attatctgaa cgagtggggc aaccgattca agaagctggc ggacatgtac     480
ggcggtggtg aggacgac                                                    498
```

```
<210> SEQ ID NO 13
<211> LENGTH: 457
<212> TYPE: DNA
<213> ORGANISM: Mus Musculus

<400> SEQUENCE: 13
cgtgtggcac catgggagat gcagaataat tatatcagtg gtctttcagc tccttccctg      60
agtgtgtaga agagagactg atctgagaag tgtgcagatt gcatagtggt ctcactctcc     120
ctactggact gtctgtgtta ggatggtttt cactgattgt tgaaatcttt ttttattttt     180 tattttttaca gtgctgagat ataaactgtg ccttttttttg tttgtttgtt tctgtttttg    240
ttcttttgag ctatgatctg ccccagacac aacagcccca agccctcac acctcactaa      300 ttttttacat tgtgtacttg ccctcaatta ccatgtttgc tgtattctaa tagtcactca     360
tgttcctgaa ttctgttgcc ctgcccaggt gatattctag gatgcagaaa tgcctgggcc     420
cttttatggt gagagacagg tatcttggtg tgggtgc                              457
```

```
<210> SEQ ID NO 14
<211> LENGTH: 66
<212> TYPE: DNA
<213> ORGANISM: porcine teschovirus-1

<400> SEQUENCE: 14
ggaagcggag ctactaactt cagcctgctg aagcaggctg agacgtggga ggagaaccct      60
ggacct                                                                 66
```

```
<210> SEQ ID NO 15
<211> LENGTH: 66
<212> TYPE: DNA
<213> ORGANISM: Artificial Sequence
<220> FEATURE:
<223> OTHER INFORMATION: aP2A sequence

<400> SEQUENCE: 15
gggagtgggg ccaccaattt tagtctacta aacaagccg gggatgtaga agaaaatccc       60
gggccc                                                                 66
```

```
<210> SEQ ID NO 16
<211> LENGTH: 1431
<212> TYPE: DNA
<213> ORGANISM: Discosoma sp

<400> SEQUENCE: 16
atggtgagca agggcgagga ggtcatcaaa gagttcatgc gcttcaaggt gcgcatggag      60
```

```
ggctccatga acggccacga gttcgagatc gagggcgagg gcgagggccg cccctacgag      120
ggcacccaga ccgccaagct gaaggtgacc aagggcggcc ccctgccctt cgcctgggac      180
atcctgtccc cccagttcat gtacggctcc aaggcgtacg tgaagcaccc cgccgacatc      240
cccgattaca agaagctgtc cttccccgag ggcttcaagt gggagcgcgt gatgaacttc      300
gaggacggcg tgtctggtgac cgtgacccag gactcctccc tgcaggacgg cacgctgatc      360
tacaaggtga agatgcgcgg caccaacttc cccccgacg gccccgtaat gcagaagaag      420
accatgggct gggaggcctc caccgagcgc ctgtacccc gcgacggcgt gctgaagggc      480
gagatccacc aggccctgaa gctgaaggac ggcggccgct acctggtgga gttcaagacc      540
atctacatgg ccaagaagcc cgtgcaactg cccggctact actacgtgga caccaagctg      600
gacatcacct cccacaacga ggactacacc atcgtggaac agtacgagcg ctccgagggc      660
cgccaccacc tgttcctggg gcatggcacc ggcagcaccg gcagcggcag ctccggcacc      720
gcctcctccg aggacaacaa catggccgtc atcaaagagt tcatgcgctt caaggtgcgc      780
atggagggct ccatgaacgg ccacgagttc gagatcgagg gcgagggcga gggccgcccc      840
tacgagggca cccagaccgc caagctgaag gtgaccaagg gcggcccct gcccttcgcc      900 tgggacatcc tgtcccccca gttcatgtac ggctccaagg cgtacgtgaa gcaccccgcc      960
gacatccccg attacaagaa gctgtccttc cccgagggct tcaagtggga gcgcgtgatg     1020
aacttcgagg acggcggtct ggtgaccgtg acccaggact cctccctgca ggacggcacg     1080
ctgatctaca aggtgaagat gcgcggcacc aacttccccc ccgacggccc cgtaatgcag     1140
aagaagacca tgggctggga ggcctccacc gagcgcctgt accccgcga cggcgtgctg     1200 aagggcgaga tccaccaggc cctgaagctg aaggacggcg ccactacct ggtggagttc     1260 aagaccatct acatggccaa gaagcccgtg caactgcccg ctactacta cgtggacacc     1320 aagctggaca tcacctccca caacgaggac tacaccatcg tggaacagta cgagcgctcc     1380
gagggccgcc accactgtt cctgtacggc atggacgagc tgtacaagta a              1431
```

<210> SEQ ID NO 17
<211> LENGTH: 720
<212> TYPE: DNA
<213> ORGANISM: Aequorea Victoria

<400> SEQUENCE: 17

```
atggtgagca agggcgagga gctgttcacc ggggtggtgc ccatcctggt cgagctggac       60
ggcgacgtaa acggccacaa gttcagcgtg tccggcgagg cgagggcga tgccacctac      120 ggcaagctga ccctgaagct gatctgcacc accggcaagc tgcccgtgcc ctggcccacc      180
ctcgtgacca ccctgggcta cggcctgcag tgcttcgccc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca ccgccgacaa gcagaagaac      480
ggcatcaagg ccaacttcaa gatccgccac aacatcgagg acggcggcgt gcagctcgcc      540
gaccactacc agcagaacac ccccatcggc gacggccccg tgctgctgcc cgacaaccac      600
tacctgagct accagtccgc cctgagcaaa gaccccaacg agaagcgcga tcacatggtc      660
ctgctggagt tcgtgaccgc cgccgggatc actctcggca tggacgagct gtacaagtaa      720
```

-continued

```
<210> SEQ ID NO 18
<211> LENGTH: 20
<212> TYPE: DNA
<213> ORGANISM: Artificial Sequence
<220> FEATURE:
<223> OTHER INFORMATION: Primer (F) for Tbx3 5' homology arm

<400> SEQUENCE: 18
gttccccact ctctaactcc                                                   20

<210> SEQ ID NO 19
<211> LENGTH: 27
<212> TYPE: DNA
<213> ORGANISM: Artificial Sequence
<220> FEATURE:
<223> OTHER INFORMATION: Primer (R) for Tbx3 5' homology arm

<400> SEQUENCE: 19
ggtaccataa ggggacccgc tgcaaga                                           27

<210> SEQ ID NO 20
<211> LENGTH: 26
<212> TYPE: DNA
<213> ORGANISM: Artificial Sequence
<220> FEATURE:
<223> OTHER INFORMATION: Primer (F) for Tbx3 3' homology arm

<400> SEQUENCE: 20
gtcgacctgc cagtgcactt tgttag                                            26

<210> SEQ ID NO 21
<211> LENGTH: 26
<212> TYPE: DNA
<213> ORGANISM: Artificial Sequence
<220> FEATURE:
<223> OTHER INFORMATION: Primer (R) for Tbx3 3' homology arm

<400> SEQUENCE: 21
atgcatcctc tacaagcgct cagata                                            26

<210> SEQ ID NO 22
<211> LENGTH: 26
<212> TYPE: DNA
<213> ORGANISM: Artificial Sequence
<220> FEATURE:
<223> OTHER INFORMATION: Primer (F) for Cdh1 5' homology arm

<400> SEQUENCE: 22
ccgcggctga ttcccccaac ttcaga                                            26

<210> SEQ ID NO 23
<211> LENGTH: 26
<212> TYPE: DNA
<213> ORGANISM: Artificial Sequence
<220> FEATURE:
<223> OTHER INFORMATION: Primer (R) for Cdh1 5' homology arm

<400> SEQUENCE: 23
ggtaccgtcg tcctcaccac cgccgt                                            26

<210> SEQ ID NO 24
<211> LENGTH: 27
<212> TYPE: DNA
<213> ORGANISM: Artificial Sequence
<220> FEATURE:
<223> OTHER INFORMATION: Primer (F) for Cdh1 3' homology arm
```

-continued

```
<400> SEQUENCE: 24
gtcgaccgtg tggcaccatg ggagatg                                        27

<210> SEQ ID NO 25
<211> LENGTH: 21
<212> TYPE: DNA
<213> ORGANISM: Artificial Sequence
<220> FEATURE:
<223> OTHER INFORMATION: Primer (R) for Cdh1 3' homology arm

<400> SEQUENCE: 25
gcacccacac caagatacct g                                              21

<210> SEQ ID NO 26
<211> LENGTH: 98
<212> TYPE: DNA
<213> ORGANISM: Artificial Sequence
<220> FEATURE:
<223> OTHER INFORMATION: Primer (F) for tdTomato

<400> SEQUENCE: 26
ggtaccggaa gcggagctac taacttcagc ctgctgaagc aggctggaga cgtggaggag    60
aaccctggac ctatggtgag caagggcgag gaggtcat                            98

<210> SEQ ID NO 27
<211> LENGTH: 29
<212> TYPE: DNA
<213> ORGANISM: Artificial Sequence
<220> FEATURE:
<223> OTHER INFORMATION: Primer (R) for tdTomato

<400> SEQUENCE: 27
gtcgacgttg ggccatggcg gccaagctt                                      29

<210> SEQ ID NO 28
<211> LENGTH: 98
<212> TYPE: DNA
<213> ORGANISM: Artificial Sequence
<220> FEATURE:
<223> OTHER INFORMATION: Primer (F) for Venus

<400> SEQUENCE: 28
ggtaccggaa gcggagctac taacttcagc ctgctgaagc aggctggaga cgtggaggag    60
aaccctggac ctatggtgag caagggcgag gaggtcat                            98

<210> SEQ ID NO 29
<211> LENGTH: 27
<212> TYPE: DNA
<213> ORGANISM: Artificial Sequence
<220> FEATURE:
<223> OTHER INFORMATION: Primer (R) for Venus

<400> SEQUENCE: 29
gtcgacttac ttgtacagct cgtccat                                        27

<210> SEQ ID NO 30
<211> LENGTH: 98
<212> TYPE: DNA
<213> ORGANISM: Artificial Sequence
<220> FEATURE:
<223> OTHER INFORMATION: Primer (F) for Neo+pA

<400> SEQUENCE: 30
ggtaccggaa gcggagctac taacttcagc ctgctgaagc aggctggaga cgtggaggag    60
```

```
aaccctggac ctatgggatc ggccattgaa caagatgg                                      98

<210> SEQ ID NO 31
<211> LENGTH: 98
<212> TYPE: DNA
<213> ORGANISM: Artificial Sequence
<220> FEATURE:
<223> OTHER INFORMATION: Primer (F) for Neo+pA

<400> SEQUENCE: 31
ggtaccggga gtggggccac caattttagt ctactaaaac aagccgggga tgtagaagaa    60
aatcccgggc ccatgggatc ggccattgaa caagatgg                                      98

<210> SEQ ID NO 32
<211> LENGTH: 28
<212> TYPE: DNA
<213> ORGANISM: Artificial Sequence
<220> FEATURE:
<223> OTHER INFORMATION: Primer (R) for Neo+pA

<400> SEQUENCE: 32
gtcgaccagc tggttctttc cgcctcag                                                 28

<210> SEQ ID NO 33
<211> LENGTH: 20
<212> TYPE: DNA
<213> ORGANISM: Artificial Sequence
<220> FEATURE:
<223> OTHER INFORMATION: Primer (F) for genotying of Tbx3-tdTomato KI

<400> SEQUENCE: 33
tagtaggcgg tggaggagaa                                                          20

<210> SEQ ID NO 34
<211> LENGTH: 20
<212> TYPE: DNA
<213> ORGANISM: Artificial Sequence
<220> FEATURE:
<223> OTHER INFORMATION: Primer (R) for genotyping of Tbx3-tdTomato KI

<400> SEQUENCE: 34
accttgaagc gcatgaactc                                                          20

<210> SEQ ID NO 35
<211> LENGTH: 20
<212> TYPE: DNA
<213> ORGANISM: Artificial Sequence
<220> FEATURE:
<223> OTHER INFORMATION: Primer (F) for genotyping of Tbx3-tdTomato KI

<400> SEQUENCE: 35
caccatcgtg gaacagtacg                                                          20

<210> SEQ ID NO 36
<211> LENGTH: 20
<212> TYPE: DNA
<213> ORGANISM: Artificial Sequence
<220> FEATURE:
<223> OTHER INFORMATION: Primer (R) for genotyping of Tbx3-tdTomato KI

<400> SEQUENCE: 36
ctaatggtcc aacaggcaca                                                          20

<210> SEQ ID NO 37
```

-continued

```
<211> LENGTH: 20
<212> TYPE: DNA
<213> ORGANISM: Artificial Sequence
<220> FEATURE:
<223> OTHER INFORMATION: Primer (F) for genotyping of Tbx3-Venus KI

<400> SEQUENCE: 37
tagtaggcgg tggaggagaa                                              20

<210> SEQ ID NO 38
<211> LENGTH: 20
<212> TYPE: DNA
<213> ORGANISM: Artificial Sequence
<220> FEATURE:
<223> OTHER INFORMATION: Primer (R) for genotyping of Tbx3-Venus KI

<400> SEQUENCE: 38
agatcagctt cagggtcagc                                              20

<210> SEQ ID NO 39
<211> LENGTH: 20
<212> TYPE: DNA
<213> ORGANISM: Artificial Sequence
<220> FEATURE:
<223> OTHER INFORMATION: Primer (F) for genotyping of Tbx3-Venus KI

<400> SEQUENCE: 39
acatggtcct gctggagttc                                              20

<210> SEQ ID NO 40
<211> LENGTH: 20
<212> TYPE: DNA
<213> ORGANISM: Artificial Sequence
<220> FEATURE:
<223> OTHER INFORMATION: Primer (R) for genotyping of Tbx3-Venus KI

<400> SEQUENCE: 40
ctaatggtcc aacaggcaca                                              20

<210> SEQ ID NO 41
<211> LENGTH: 20
<212> TYPE: DNA
<213> ORGANISM: Artificial Sequence
<220> FEATURE:
<223> OTHER INFORMATION: Primer (F) for detection of wild type after
      Tbx3-tdTomato(Venus) KI

<400> SEQUENCE: 41
actcggggtc ggaactgaac                                              20

<210> SEQ ID NO 42
<211> LENGTH: 19
<212> TYPE: DNA
<213> ORGANISM: Artificial Sequence
<220> FEATURE:
<223> OTHER INFORMATION: Primer (R)  for detection of wild type after
      Tbx3-tdTomato(Venus) KI

<400> SEQUENCE: 42
cctggctacc ttgttcttc                                               19

<210> SEQ ID NO 43
<211> LENGTH: 20
<212> TYPE: DNA
<213> ORGANISM: Artificial Sequence
<220> FEATURE:
<223> OTHER INFORMATION: Primer (F) for genotyping of Cdh1-tdTomato KI
```

```
<400> SEQUENCE: 43
aggccacacc tcctaatcct                                            20

<210> SEQ ID NO 44
<211> LENGTH: 20
<212> TYPE: DNA
<213> ORGANISM: Artificial Sequence
<220> FEATURE:
<223> OTHER INFORMATION: Primer (R) for genotyping of Cdh1-tdTomato KI

<400> SEQUENCE: 44
accttgaagc gcatgaactc                                            20

<210> SEQ ID NO 45
<211> LENGTH: 20
<212> TYPE: DNA
<213> ORGANISM: Artificial Sequence
<220> FEATURE:
<223> OTHER INFORMATION: Primer (F) for genotyping of Cdh1-tdTomato KI

<400> SEQUENCE: 45
caccatcgtg gaacagtacg                                            20

<210> SEQ ID NO 46
<211> LENGTH: 20
<212> TYPE: DNA
<213> ORGANISM: Artificial Sequence
<220> FEATURE:
<223> OTHER INFORMATION: Primer (R) for genotyping of Cdh1-tdTomato KI

<400> SEQUENCE: 46
gcatgcatag tggtcccttt                                            20

<210> SEQ ID NO 47
<211> LENGTH: 20
<212> TYPE: DNA
<213> ORGANISM: Artificial Sequence
<220> FEATURE:
<223> OTHER INFORMATION: Primer (F) for genotyping of Cdh1-Venus KI

<400> SEQUENCE: 47
aggccacacc tcctaatcct                                            20

<210> SEQ ID NO 48
<211> LENGTH: 20
<212> TYPE: DNA
<213> ORGANISM: Artificial Sequence
<220> FEATURE:
<223> OTHER INFORMATION: Primer (R) for genotyping of Cdh1-Venus KI

<400> SEQUENCE: 48
agatcagctt cagggtcagc                                            20

<210> SEQ ID NO 49
<211> LENGTH: 20
<212> TYPE: DNA
<213> ORGANISM: Artificial Sequence
<220> FEATURE:
<223> OTHER INFORMATION: Primer (F) for genotyping of Cdh1-Venus KI

<400> SEQUENCE: 49
acatggtcct gctggagttc                                            20

<210> SEQ ID NO 50
```

-continued

```
<211> LENGTH: 20
<212> TYPE: DNA
<213> ORGANISM: Artificial Sequence
<220> FEATURE:
<223> OTHER INFORMATION: Primer (R) for genotyping of Cdh1-Venus KI

<400> SEQUENCE: 50
gcatgcatag tggtcccttt                                                          20

<210> SEQ ID NO 51
<211> LENGTH: 20
<212> TYPE: DNA
<213> ORGANISM: Artificial Sequence
<220> FEATURE:
<223> OTHER INFORMATION: Primer (F) for detection of wild type after
     Tbx3-tdTomato(Venus) KI

<400> SEQUENCE: 51
ggtgttgctt gcctctgatg                                                          20

<210> SEQ ID NO 52
<211> LENGTH: 21
<212> TYPE: DNA
<213> ORGANISM: Artificial Sequence
<220> FEATURE:
<223> OTHER INFORMATION: Primer (R) for detection of wild type after
     Tbx3-tdTomato(Venus) KI

<400> SEQUENCE: 52
ccagtaggga gagtgagacc a                                                        21

<210> SEQ ID NO 53
<211> LENGTH: 20
<212> TYPE: DNA
<213> ORGANISM: Artificial Sequence
<220> FEATURE:
<223> OTHER INFORMATION: Primer (F) for detection of wild type after
     Tbx3-tdTomato(Venus) KI

<400> SEQUENCE: 53
cgactctctg ttggtgttcg                                                          20

<210> SEQ ID NO 54
<211> LENGTH: 20
<212> TYPE: DNA
<213> ORGANISM: Artificial Sequence
<220> FEATURE:
<223> OTHER INFORMATION: Primer (R) for detection of wild type after
     Tbx3-tdTomato(Venus) KI

<400> SEQUENCE: 54
tctggggcag atcatagctc                                                          20

<210> SEQ ID NO 55
<211> LENGTH: 20
<212> TYPE: DNA
<213> ORGANISM: Artificial Sequence
<220> FEATURE:
<223> OTHER INFORMATION: Primer (F) for detection of indel in Rosa26
     region

<400> SEQUENCE: 55
cgtgttcgtg caagttgagt                                                          20

<210> SEQ ID NO 56
<211> LENGTH: 20
<212> TYPE: DNA
```

-continued

```
<213> ORGANISM: Artificial Sequence
<220> FEATURE:
<223> OTHER INFORMATION: Primer (R) for detection of indel in Rosa26
      region

<400> SEQUENCE: 56
ctccactgca gctcccttac                                              20

<210> SEQ ID NO 57
<211> LENGTH: 20
<212> TYPE: DNA
<213> ORGANISM: Artificial Sequence
<220> FEATURE:
<223> OTHER INFORMATION: Primer (F) for detection of indel in Albmin
      region

<400> SEQUENCE: 57
ggagagccac ttgcctcata                                              20

<210> SEQ ID NO 58
<211> LENGTH: 20
<212> TYPE: DNA
<213> ORGANISM: Artificial Sequence
<220> FEATURE:
<223> OTHER INFORMATION: Primer (R) for detection of indel in Albmin
      region

<400> SEQUENCE: 58
ttgtggtctt tccctcatcc                                              20

<210> SEQ ID NO 59
<211> LENGTH: 33
<212> TYPE: DNA
<213> ORGANISM: Artificial Sequence
<220> FEATURE:
<223> OTHER INFORMATION: Linker (F) for construction of sgRNA(10C)
      expression PX459 vector

<400> SEQUENCE: 59
caccgccccc ccaccgggtc ttcgagaaga cct                               33

<210> SEQ ID NO 60
<211> LENGTH: 33
<212> TYPE: DNA
<213> ORGANISM: Artificial Sequence
<220> FEATURE:
<223> OTHER INFORMATION: Linker (R) for construction of sgRNA(10C)
      expression PX459 vector

<400> SEQUENCE: 60
aaacaggtct tctcgaagac ccggtggggg ggc                               33

<210> SEQ ID NO 61
<211> LENGTH: 48
<212> TYPE: DNA
<213> ORGANISM: Artificial Sequence
<220> FEATURE:
<223> OTHER INFORMATION: Linker (F) for construction of sgRNA(25C)
      expression PX459 vector

<400> SEQUENCE: 61
caccgccccc ccccccccccc cccccccacc gggtcttcga aagacct               48

<210> SEQ ID NO 62
<211> LENGTH: 48
<212> TYPE: DNA
<213> ORGANISM: Artificial Sequence
```

-continued

```
<220> FEATURE:
<223> OTHER INFORMATION: Linker (R) for construction of sgRNA(25C)
      expression PX459 vector

<400> SEQUENCE: 62
aaacaggtct tctcgaagac ccggtggggg ggggggggg ggggggggc                  48

<210> SEQ ID NO 63
<211> LENGTH: 25
<212> TYPE: DNA
<213> ORGANISM: Artificial Sequence
<220> FEATURE:
<223> OTHER INFORMATION: Linker (F) for construction of sgRNA expression
      vector for Tbx3-tdTomato(Venus) KI

<400> SEQUENCE: 63
caccgactgg cagatttgac caaac                                          25

<210> SEQ ID NO 64
<211> LENGTH: 25
<212> TYPE: DNA
<213> ORGANISM: Artificial Sequence
<220> FEATURE:
<223> OTHER INFORMATION: Linker (R) for construction of sgRNA expression
      vector for Tbx3-tdTomato(Venus) KI

<400> SEQUENCE: 64
aaacgtttgg tcaaatctgc cagtc                                          25

<210> SEQ ID NO 65
<211> LENGTH: 25
<212> TYPE: DNA
<213> ORGANISM: Artificial Sequence
<220> FEATURE:
<223> OTHER INFORMATION: Linker (F) for construction of sgRNA expression
      vector for Cdh1-tdTomato(Venus) KI

<400> SEQUENCE: 65
caccgtctcc cccgtgtggc accat                                          25

<210> SEQ ID NO 66
<211> LENGTH: 25
<212> TYPE: DNA
<213> ORGANISM: Artificial Sequence
<220> FEATURE:
<223> OTHER INFORMATION: Linker (R) for construction of sgRNA expression
      vector for Cdh1-tdTomato(Venus) KI

<400> SEQUENCE: 66
aaacatggtg ccacacgggg gagac                                          25

<210> SEQ ID NO 67
<211> LENGTH: 25
<212> TYPE: DNA
<213> ORGANISM: Artificial Sequence
<220> FEATURE:
<223> OTHER INFORMATION: Linker (F) for construction of P2A sgRNA
      expression vector

<400> SEQUENCE: 67
caccgtaact tcagcctgct gaagc                                          25

<210> SEQ ID NO 68
<211> LENGTH: 25
<212> TYPE: DNA
<213> ORGANISM: Artificial Sequence
<220> FEATURE:
```

<223> OTHER INFORMATION: Linker (R) for construction of P2A sgRNA
      expression vector

<400> SEQUENCE: 68
aaacgcttca gcaggctgaa gttac                                                     25

<210> SEQ ID NO 69
<211> LENGTH: 25
<212> TYPE: DNA
<213> ORGANISM: Artificial Sequence
<220> FEATURE:
<223> OTHER INFORMATION: Linker (F) for construction of P2A sgRNA
      expression vector (mismach position 1)

<400> SEQUENCE: 69
caccgtaact tcagcctgct gaagg                                                     25

<210> SEQ ID NO 70
<211> LENGTH: 25
<212> TYPE: DNA
<213> ORGANISM: Artificial Sequence
<220> FEATURE:
<223> OTHER INFORMATION: Linker (R) for construction of P2A sgRNA
      expression vector (mismach position 1)

<400> SEQUENCE: 70
aaacccttca gcaggctgaa gttac                                                     25

<210> SEQ ID NO 71
<211> LENGTH: 25
<212> TYPE: DNA
<213> ORGANISM: Artificial Sequence
<220> FEATURE:
<223> OTHER INFORMATION: Linker (F) for construction of aP2A sgRNA
      expression vector

<400> SEQUENCE: 71
caccgtagtc tactaaaaca agccg                                                     25

<210> SEQ ID NO 72
<211> LENGTH: 25
<212> TYPE: DNA
<213> ORGANISM: Artificial Sequence
<220> FEATURE:
<223> OTHER INFORMATION: Linker (R) for construction of aP2A sgRNA
      expression vector

<400> SEQUENCE: 72
aaaccggctt gttttagtag actac                                                     25

<210> SEQ ID NO 73
<211> LENGTH: 25
<212> TYPE: DNA
<213> ORGANISM: Artificial Sequence
<220> FEATURE:
<223> OTHER INFORMATION: Linker (F) for construction of aP2A sgRNA
      expression vector (mismach position 1)

<400> SEQUENCE: 73
caccgtagtc tactaaaaca agccc                                                     25

<210> SEQ ID NO 74
<211> LENGTH: 25
<212> TYPE: DNA
<213> ORGANISM: Artificial Sequence
<220> FEATURE:
<223> OTHER INFORMATION: Linker (R) for construction of aP2A sgRNA -continued expression vector (mismach position 1)

<400> SEQUENCE: 74
aaacgggctt gttttagtag actac                                          25

<210> SEQ ID NO 75
<211> LENGTH: 39
<212> TYPE: DNA
<213> ORGANISM: Artificial Sequence
<220> FEATURE:
<223> OTHER INFORMATION: Linker (F) for construction of P2A sgRNA
      expression vector (15G addition at 5' end )

<400> SEQUENCE: 75 caccggggggg gggggggggt aacttcagcc tgctgaagc                           39

<210> SEQ ID NO 76
<211> LENGTH: 39
<212> TYPE: DNA
<213> ORGANISM: Artificial Sequence
<220> FEATURE:
<223> OTHER INFORMATION: Linker (R) for construction of P2A sgRNA
      expression vector (15G addition at 5' end )

<400> SEQUENCE: 76
aaacgcttca gcaggctgaa gttacccccc cccccccccc                           39

<210> SEQ ID NO 77
<211> LENGTH: 30
<212> TYPE: DNA
<213> ORGANISM: Artificial Sequence
<220> FEATURE:
<223> OTHER INFORMATION: Linker (F) for construction of P2A sgRNA
      expression vector (5C addition at 3' end )

<400> SEQUENCE: 77
caccgtaact tcagcctgct gaagcccccc                                      30

<210> SEQ ID NO 78
<211> LENGTH: 30
<212> TYPE: DNA
<213> ORGANISM: Artificial Sequence
<220> FEATURE:
<223> OTHER INFORMATION: Linker (R) for construction of P2A sgRNA
      expression vector (5C addition at 3' end )

<400> SEQUENCE: 78 aaacggggg cttcagcagg ctgaagttac                                       30

<210> SEQ ID NO 79
<211> LENGTH: 35
<212> TYPE: DNA
<213> ORGANISM: Artificial Sequence
<220> FEATURE:
<223> OTHER INFORMATION: Linker (F) for construction of P2A sgRNA
      expression vector (10C addition at 3' end )

<400> SEQUENCE: 79
caccgtaact tcagcctgct gaagcccccc ccccc                                35

<210> SEQ ID NO 80
<211> LENGTH: 35
<212> TYPE: DNA
<213> ORGANISM: Artificial Sequence
<220> FEATURE:
<223> OTHER INFORMATION: Linker (R) for construction of P2A sgRNA
      expression vector (10C addition at 3' end )

-continued

<400> SEQUENCE: 80
aaacgggggg gggggcttca gcaggctgaa gttac                              35

<210> SEQ ID NO 81
<211> LENGTH: 30
<212> TYPE: DNA
<213> ORGANISM: Artificial Sequence
<220> FEATURE:
<223> OTHER INFORMATION: Linker (F) for construction of aP2A sgRNA
      expression vector (5C addition at 5' end )

<400> SEQUENCE: 81
caccgccccc tagtctacta aacaagccg                                    30

<210> SEQ ID NO 82
<211> LENGTH: 30
<212> TYPE: DNA
<213> ORGANISM: Artificial Sequence
<220> FEATURE:
<223> OTHER INFORMATION: Linker (R) for construction of aP2A sgRNA
      expression vector (5C addition at 5' end )

<400> SEQUENCE: 82
aaaccggctt gttttagtag actaggggc                                    30

<210> SEQ ID NO 83
<211> LENGTH: 24
<212> TYPE: DNA
<213> ORGANISM: Artificial Sequence
<220> FEATURE:
<223> OTHER INFORMATION: Linker (F) for constuction of human EMX1 sgRNA
      expression vector

<400> SEQUENCE: 83
caccgagtcc gagcagaaga agaa                                         24

<210> SEQ ID NO 84
<211> LENGTH: 24
<212> TYPE: DNA
<213> ORGANISM: Artificial Sequence
<220> FEATURE:
<223> OTHER INFORMATION: Linker (R) for constuction of human EMX1 sgRNA
      expression vector

<400> SEQUENCE: 84
aaacttcttc ttctgctcgg actc                                         24

<210> SEQ ID NO 85
<211> LENGTH: 21
<212> TYPE: DNA
<213> ORGANISM: Homo sapiens

<400> SEQUENCE: 85
aaaaccaccc ttctctctgg c                                            21

<210> SEQ ID NO 86
<211> LENGTH: 21
<212> TYPE: DNA
<213> ORGANISM: Homo sapiens

<400> SEQUENCE: 86
ggagattgga gacacggaga g                                            21

<210> SEQ ID NO 87

```
<211> LENGTH: 20
<212> TYPE: DNA
<213> ORGANISM: Artificial Sequence
<220> FEATURE:
<223> OTHER INFORMATION: Linker (F) for construction of Rosa26 sgRNA
      expression vector

<400> SEQUENCE: 87
agacctccat cgcgcactcc                                                    20

<210> SEQ ID NO 88
<211> LENGTH: 20
<212> TYPE: DNA
<213> ORGANISM: Artificial Sequence
<220> FEATURE:
<223> OTHER INFORMATION: Linker (R) for construction of Rosa26 sgRNA
      expression vector

<400> SEQUENCE: 88
ggagtgcgcg atggaggtct                                                    20

<210> SEQ ID NO 89
<211> LENGTH: 20
<212> TYPE: DNA
<213> ORGANISM: Artificial Sequence
<220> FEATURE:
<223> OTHER INFORMATION: Linker (F) for construction of Alb sgRNA
      expression vector

<400> SEQUENCE: 89
actccatcac ttaaggcccc                                                    20

<210> SEQ ID NO 90
<211> LENGTH: 20
<212> TYPE: DNA
<213> ORGANISM: Artificial Sequence
<220> FEATURE:
<223> OTHER INFORMATION: Linker (R) for construction of Alb sgRNA
      expression vector

<400> SEQUENCE: 90
ggggccttaa gtgatggagt                                                    20

<210> SEQ ID NO 91
<211> LENGTH: 20
<212> TYPE: DNA
<213> ORGANISM: Homo sapiens

<400> SEQUENCE: 91
gagtctaagc agaagaagaa                                                    20

<210> SEQ ID NO 92
<211> LENGTH: 21
<212> TYPE: DNA
<213> ORGANISM: Homo sapiens

<400> SEQUENCE: 92
tgaaatctca cctgggcgag a                                                  21

<210> SEQ ID NO 93
<211> LENGTH: 20
<212> TYPE: DNA
<213> ORGANISM: Homo sapiens

<400> SEQUENCE: 93
tgcagtctgc ctttttgggg                                                    20
```

-continued

```
<210> SEQ ID NO 94
<211> LENGTH: 23
<212> TYPE: DNA
<213> ORGANISM: Homo sapiens

<400> SEQUENCE: 94
tgaccgtcta aactggtttg acc                                           23

<210> SEQ ID NO 95
<211> LENGTH: 20
<212> TYPE: DNA
<213> ORGANISM: porcine teschovirus-1

<400> SEQUENCE: 95
taacttcagc ctgctgaagc                                               20

<210> SEQ ID NO 96
<211> LENGTH: 20
<212> TYPE: DNA
<213> ORGANISM: Artificial Sequence
<220> FEATURE:
<223> OTHER INFORMATION: aP2A target sequence

<400> SEQUENCE: 96
tagtctacta aaacaagccg                                               20

<210> SEQ ID NO 97
<211> LENGTH: 29
<212> TYPE: DNA
<213> ORGANISM: Artificial Sequence
<220> FEATURE:
<223> OTHER INFORMATION: Region including P2A target sequence in AIMS

<400> SEQUENCE: 97
ctactaactt cagcctgctg aagcaggct                                     29

<210> SEQ ID NO 98
<211> LENGTH: 20
<212> TYPE: RNA
<213> ORGANISM: Artificial Sequence
<220> FEATURE:
<223> OTHER INFORMATION: sgRNA for P2A (one mismatch)

<400> SEQUENCE: 98
uaacuucugc cugcugaagc                                               20

<210> SEQ ID NO 99
<211> LENGTH: 20
<212> TYPE: RNA
<213> ORGANISM: Artificial Sequence
<220> FEATURE:
<223> OTHER INFORMATION: sgRNA for P2A

<400> SEQUENCE: 99
uaacuucugc cugcugaagc                                               20

<210> SEQ ID NO 100
<211> LENGTH: 24
<212> TYPE: DNA
<213> ORGANISM: Artificial Sequence
<220> FEATURE:
<223> OTHER INFORMATION: Linker (F) for construction of human
      ACVR1(R206H) sgRNA expression vector

<400> SEQUENCE: 100
```

-continued

```
caccggctca ccagattaca ctgt                                         24

<210> SEQ ID NO 101
<211> LENGTH: 24
<212> TYPE: DNA
<213> ORGANISM: Artificial Sequence
<220> FEATURE:
<223> OTHER INFORMATION: Linker (R) for construction of human
      ACVR1(R206H) sgRNA expression vector

<400> SEQUENCE: 101
aaacacagtg taatctggtg agcc                                         24

<210> SEQ ID NO 102
<211> LENGTH: 155
<212> TYPE: DNA
<213> ORGANISM: Artificial Sequence
<220> FEATURE:
<223> OTHER INFORMATION: ssODN for correction of human ACVR1(R206H)

<400> SEQUENCE: 102
ggccgcattt attggatcat tcgtgtacat caggaagtgg ctctggtctt ccttttctgg     60
tacaaagaac agtggcgcgc cagattacac tgttggagtg tgtcggtaat tctttttttt    120
cctttctttg tgggtaatat gcaatgttac ctgca                              155

<210> SEQ ID NO 103
<211> LENGTH: 20
<212> TYPE: DNA
<213> ORGANISM: Homo sapiens

<400> SEQUENCE: 103
agttgctgga aatcctgtgg                                               20

<210> SEQ ID NO 104
<211> LENGTH: 20
<212> TYPE: DNA
<213> ORGANISM: Homo sapiens

<400> SEQUENCE: 104
ttcacgctag gcattgtctg                                               20

<210> SEQ ID NO 105
<211> LENGTH: 24
<212> TYPE: DNA
<213> ORGANISM: Artificial Sequence
<220> FEATURE:
<223> OTHER INFORMATION: Linker (F) for construction of mouse Acvr1(wt)
      sgRNA expression vector

<400> SEQUENCE: 105
caccggctcg ccagataacc ctgt                                         24

<210> SEQ ID NO 106
<211> LENGTH: 24
<212> TYPE: DNA
<213> ORGANISM: Artificial Sequence
<220> FEATURE:
<223> OTHER INFORMATION: Linker (R) for construction of mouse Acvr1(wt)
      sgRNA expression vector

<400> SEQUENCE: 106
aaacacaggg ttatctggcg agcc                                         24
```

-continued

```
<210> SEQ ID NO 107
<211> LENGTH: 153
<212> TYPE: DNA
<213> ORGANISM: Artificial Sequence
<220> FEATURE:
<223> OTHER INFORMATION: ssODN for induction of mouse Acvr1(R206H)

<400> SEQUENCE: 107
ggccgcctac tagatcactc gtgtacatca ggaagtggct ccggtcttcc tttcctggta      60
cagagaacgg tggctcacca gataaccctg ttggagtgtg tcggtaattc tatgtttccc     120
ttccttttgg gcagcaggca atgttggcct gca                                  153

<210> SEQ ID NO 108
<211> LENGTH: 20
<212> TYPE: DNA
<213> ORGANISM: Mus Musculus

<400> SEQUENCE: 108
agttgctgga aatcctgtgg                                                  20

<210> SEQ ID NO 109
<211> LENGTH: 20
<212> TYPE: DNA
<213> ORGANISM: Mus Musculus

<400> SEQUENCE: 109
ttcacgctag gcattgtctg                                                  20

<210> SEQ ID NO 110
<211> LENGTH: 24
<212> TYPE: DNA
<213> ORGANISM: Artificial Sequence
<220> FEATURE:
<223> OTHER INFORMATION: Linker (F) for construction of human ACVR1(wt)
     sgRNA expression vector

<400> SEQUENCE: 110
caccggctcg ccagattaca ctgt                                             24

<210> SEQ ID NO 111
<211> LENGTH: 24
<212> TYPE: DNA
<213> ORGANISM: Artificial Sequence
<220> FEATURE:
<223> OTHER INFORMATION: Linker (R) for construction of human ACVR1(wt)
     sgRNA expression vector

<400> SEQUENCE: 111
aaacacagtg taatctggcg agcc                                             24

<210> SEQ ID NO 112
<211> LENGTH: 20
<212> TYPE: DNA
<213> ORGANISM: Homo sapiens

<400> SEQUENCE: 112
ggctcaccag attacactgt                                                  20

<210> SEQ ID NO 113
<211> LENGTH: 20
<212> TYPE: DNA
<213> ORGANISM: Homo sapiens

<400> SEQUENCE: 113
```

-continued

```
ggctcgccag attacactgt                                                    20

<210> SEQ ID NO 114
<211> LENGTH: 20
<212> TYPE: DNA
<213> ORGANISM: Artificial Sequence
<220> FEATURE:
<223> OTHER INFORMATION: target sequence of ssODN for correction of
      human ACVR1(R206H)

<400> SEQUENCE: 114
ggcgcgccag attacactgt                                                    20

<210> SEQ ID NO 115
<211> LENGTH: 20
<212> TYPE: DNA
<213> ORGANISM: Mus Musculus

<400> SEQUENCE: 115
ggctcgccag ataaccctgt                                                    20

<210> SEQ ID NO 116
<211> LENGTH: 20
<212> TYPE: DNA
<213> ORGANISM: Mus Musculus

<400> SEQUENCE: 116
ggctcaccag ataaccctgt                                                    20

<210> SEQ ID NO 117
<211> LENGTH: 28
<212> TYPE: DNA
<213> ORGANISM: Artificial Sequence
<220> FEATURE:
<223> OTHER INFORMATION: Linker (F) for construction of sgRNA(5C)
      expression PX459 vector

<400> SEQUENCE: 117
caccgccacc gggtcttcga gaagacct                                           28

<210> SEQ ID NO 118
<211> LENGTH: 28
<212> TYPE: DNA
<213> ORGANISM: Artificial Sequence
<220> FEATURE:
<223> OTHER INFORMATION: Linker (R) for construction of sgRNA(5C)
      expression PX459 vector

<400> SEQUENCE: 118
aaacaggtct tctcgaagac ccggtggc                                           28

<210> SEQ ID NO 119
<211> LENGTH: 38
<212> TYPE: DNA
<213> ORGANISM: Artificial Sequence
<220> FEATURE:
<223> OTHER INFORMATION: Linker (F) for construction of sgRNA(15C)
      expression PX459 vector

<400> SEQUENCE: 119
caccgccccc ccccccacc gggtcttcga gaagacct                                 38

<210> SEQ ID NO 120
<211> LENGTH: 38
<212> TYPE: DNA
<213> ORGANISM: Artificial Sequence
```

<220> FEATURE:
<223> OTHER INFORMATION: Linker (R) for construction of sgRNA(15C)
      expression PX459 vector

<400> SEQUENCE: 120
aaacaggtct tctcgaagac ccggtggggg ggggggggc                          38

<210> SEQ ID NO 121
<211> LENGTH: 43
<212> TYPE: DNA
<213> ORGANISM: Artificial Sequence
<220> FEATURE:
<223> OTHER INFORMATION: Linker (F) for construction of sgRNA(20C)
      expression PX459 vector

<400> SEQUENCE: 121
caccgccccc ccccccccc ccaccgggtc ttcgagaaga cct                      43

<210> SEQ ID NO 122
<211> LENGTH: 43
<212> TYPE: DNA
<213> ORGANISM: Artificial Sequence
<220> FEATURE:
<223> OTHER INFORMATION: Linker (R) for construction of sgRNA(00C)
      expression PX459 vector

<400> SEQUENCE: 122
aaacaggtct tctcgaagac ccggtggggg gggggggggg ggc                     43

<210> SEQ ID NO 123
<211> LENGTH: 53
<212> TYPE: DNA
<213> ORGANISM: Artificial Sequence
<220> FEATURE:
<223> OTHER INFORMATION: Linker (F) for construction of sgRNA(30C)
      expression PX459 vector

<400> SEQUENCE: 123
caccgccccc ccccccccc ccccccccc ccaccgggtc ttcgagaaga cct            53

<210> SEQ ID NO 124
<211> LENGTH: 53
<212> TYPE: DNA
<213> ORGANISM: Artificial Sequence
<220> FEATURE:
<223> OTHER INFORMATION: Linker (R) for construction of sgRNA(30C)
      expression PX459 vector

<400> SEQUENCE: 124
aaacaggtct tctcgaagac ccggtggggg gggggggggg gggggggggg ggc          53

<210> SEQ ID NO 125
<211> LENGTH: 25
<212> TYPE: DNA
<213> ORGANISM: Artificial Sequence
<220> FEATURE:
<223> OTHER INFORMATION: Linker (F) for construction of Cdh1 region in
      Compound heterozygous of Cdh1-P2A-AIMS cell

<400> SEQUENCE: 125
caccgagtct ctcttctaca cactc                                         25

<210> SEQ ID NO 126
<211> LENGTH: 25
<212> TYPE: DNA
<213> ORGANISM: Artificial Sequence
<220> FEATURE:

<223> OTHER INFORMATION: Linker (R) for construction of Cdh1 region in
      Compound heterozygous of Cdh1-P2A-AIMS cell

<400> SEQUENCE: 126
aaacgagtgt gtagaagaga gactc                                                        25

<210> SEQ ID NO 127
<211> LENGTH: 20
<212> TYPE: DNA
<213> ORGANISM: Artificial Sequence
<220> FEATURE:
<223> OTHER INFORMATION: Primer (F) for genotyping of Tomato allele in
      Compound heterozygous

<400> SEQUENCE: 127
cctgttcctg tacggcatgg                                                              20

<210> SEQ ID NO 128
<211> LENGTH: 20
<212> TYPE: DNA
<213> ORGANISM: Artificial Sequence
<220> FEATURE:
<223> OTHER INFORMATION: Primer (R) for in vitro digestion assay

<400> SEQUENCE: 128
cgtccatgcc gagagtgatc                                                              20

<210> SEQ ID NO 129
<211> LENGTH: 48
<212> TYPE: DNA
<213> ORGANISM: Artificial Sequence
<220> FEATURE:
<223> OTHER INFORMATION: Primer (F) for in vitro digestion assay (T7
      promoter +0C-P2A-sgRNA)

<400> SEQUENCE: 129
gcggcctcta atacgactca ctatagggta acttcagcct gctgaagc                               48

<210> SEQ ID NO 130
<211> LENGTH: 58
<212> TYPE: DNA
<213> ORGANISM: Artificial Sequence
<220> FEATURE:
<223> OTHER INFORMATION: Primer (F) for in vitro digestion assay (T7
      promoter + 10C-P2A-sgRNA)

<400> SEQUENCE: 130
gcggcctcta atacgactca ctatagggcc ccccccccta acttcagcct gctgaagc                    58

<210> SEQ ID NO 131
<211> LENGTH: 73
<212> TYPE: DNA
<213> ORGANISM: Artificial Sequence
<220> FEATURE:
<223> OTHER INFORMATION: Primer (F) for in vitro digestion assay (T7
      promoter + 25C-P2A-sgRNA)

<400> SEQUENCE: 131
gcggcctcta atacgactca ctatagggcc cccccccccc cccccccccc ccctaacttc     60
agcctgctga agc                                                       73

<210> SEQ ID NO 132
<211> LENGTH: 24
<212> TYPE: DNA
<213> ORGANISM: Artificial Sequence
<220> FEATURE:

-continued

<223> OTHER INFORMATION: Primer (R) for in vitro digestion assay (sgRNA)

<400> SEQUENCE: 132
aaaaaagcac cgactcggtg ccac                                              24

PRODUCTION METHOD FOR GENOME-EDITED CELLS

TECHNICAL FIELD

The present invention relates to the field of genome editing. The present invention particularly relates to a production method for a cell in which only one allele is genome-edited; a guide RNA, an expression vector, and a kit which can be used in the production method; and a prediction method for a genome editing pattern. The present invention further relates to an analysis method for a genome editing pattern, and a cell that can be used in the analysis method.

Priority is claimed on Japanese Patent Application No. 2018-232946, filed Dec. 12, 2018, the content of which is incorporated herein by reference.

BACKGROUND ART

It is known that Clustered Regularly Interspaced Short Palindromic Repeats (CRISPR), along with CRISPR-associated (Cas) genes, constitutes an adaptive immune system, which provides acquired resistance against invading foreign nucleic acids, in bacteria and archaea. CRISPR consists of short conserved repeat sequences of 24 to 48 bp interspersed with unique variable DNA sequences called spacers, which have similar sizes and are derived from phage or plasmid DNA in many cases. Furthermore, a gene group encoding a Cas protein family is present in the vicinity of repeats and spacer sequences.

In the CRISPR/Cas system, exogenous DNA is cleaved into fragments of about 30 bp by the Cas protein family and inserted into CRISPR. Cas1 and Cas2 proteins, which are part of the Cas protein family, recognize a base sequence called proto-spacer adjacent motif (PAM) of the exogenous DNA, cut off the upstream of the base sequence, and insert the upstream into a CRISPR sequence of a host, resulting in immunological memory of bacteria. RNA (called pre-crRNA), which is generated by transcription of the CRISPR sequence containing immunological memory, is paired with partially complementary RNA (trans-activating crRNA: tracrRNA) and is incorporated into a Cas9 protein which is a member of the Cas protein family. The pre-crRNA and the tracrRNA incorporated into the Cas9 are cleaved into small RNA fragments (CRISPR-RNAs: crRNAs) containing foreign sequences (guide sequences) by RNAase III, and thereby a Cas9-crRNA-tracrRNA complex is formed. The Cas9-crRNA-tracrRNA complex is bonded to invading exogenous DNA complementary to the crRNA, the Cas9 protein, which is a nuclease that cleaves DNA, cleaves the invading exogenous DNA, and thereby functions of the DNA invading from the outside are inhibited and eliminated.

The Cas9 protein recognizes a PAM sequence in invading exogenous DNA and cleaves double-stranded DNA at a site upstream of the PAM sequence to generate blunt ends. A length and a base sequence of a PAM sequence vary depending on bacterial species, and 3 bases of "NGG" are recognized for Streptococcus pyogenes (S. pyogenes). Streptococcus thermophilus (S. thermophilus) has two Cas9's, and they respectively recognize 5 and 6 bases of "NGGNG" and "NNAGAA" as PAM sequences (where N represents an arbitrary base). How many bp upstream of a PAM sequence a site should be cleaved also depends on bacterial species, but in most Cas9 orthologs including S. pyogenes, a site 3 bases upstream of a PAM sequence is cleaved.

In recent years, techniques for applying the CRISPR/Cas system in bacteria to genome editing have been actively developed. CrRNA and tracrRNA are fused and expressed as a tracrRNA-crRNA chimera (sgRNA) for utilization. Accordingly, an RNA-guided nuclease (RGN) is called in, and genomic DNA is cleaved at a site of interest.

In CRISPR/Cas systems, there are type I, type II, and type III, but the type II CRISPR/Cas system is exclusively used for genome editing, and a Cas9 protein is used as an RGN in the type II. A Cas9 protein derived from S. pyogenes recognizes 3 bases of NGG as a PAM sequence, and therefore as long as there is a sequence in which two guanines are arranged, a site upstream of the PAM sequence can be cleaved.

A method using the CRISPR/Cas system only requires synthesis of short sgRNA having a sequence homologous to a target DNA sequence, and genome editing can be performed using a single protein of a Cas9 protein. Therefore, it is not required to synthesize a large amount of proteins which differ for each DNA sequence as in conventionally used zinc finger nucleases (ZFNs) and transcription activator-like effector nucleases (TALENs), and genome editing can be performed easily and quickly.

For example, Patent Document 1 discloses a genome editing technique utilizing a CRISPR/Cas system derived from S. pyogenes.

CITATION LIST

Patent Document

[Patent Document 1]
PCT International Publication No. WO2014/093661

SUMMARY OF INVENTION

Technical Problem

It is known that DNA in which a double-strand break occurred by genome editing is repaired by Homologous Directed Repair (HDR) or Non-Homologous End-Joining Repair (NHEJ). In the case of NHEJ, because insertion and/or deletion (indel) is frequently induced during repair, there is a concern of occurrence of unexpected gene mutations.

For example, in a case where a disease gene and a normal gene are heterozygously present, and when knockout of the disease gene is attempted by genome editing, there is a concern of induction of mutations also in the normal gene at a high frequency. Furthermore, even when knock-in of the normal gene is attempted by HDR, a probability of occurrence of knock-in in both alleles is extremely low. Therefore, there is a concern of introducing indel, by NHEJ, into an allele in which knock-in is not induced.

Therefore, in a case where double-strand breaks occur in both alleles by genome editing, there is a risk of inducing unexpected mutations in one allele.

The present invention has been made in view of the above circumstances, and an object of the present invention is to provide a production method for a cell in which only one allele is genome-edited; and a guide RNA, an expression vector, and a kit which can be used in the method. Another object of the present invention is to provide a prediction method for a genome editing pattern, an analysis method for a genome editing pattern, and a cell that can be used in the analysis method.

Solution to Problem

The present invention includes the following aspects.

[1] A production method for a cell in which only one allele is genome-edited, the method including: a step of introducing, into a cell, (A) at least one selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector for the guide RNA of (a1) or (a2), and (B) at least one selected from the group consisting of a Cas protein and an expression vector for the Cas protein.

[2] The production method for a cell in which only one allele is genome-edited according to [1], in which (A) is a guide RNA, in which one or more nucleotide residues are added to a 5'-end of a spacer sequence and the spacer sequence is a spacer sequence having single-base or multiple-base mismatches with respect to a target sequence, or an expression vector encoding the guide RNA.

[3] The production method for a cell in which only one allele is genome-edited according to [1] or [2], in which the nucleotide residues added to the 5'-end of the spacer sequence are all the same nucleotide residues.

[4] The production method for a cell in which only one allele is genome-edited according to [3], in which the nucleotide residues added to the 5'-end of the spacer sequence are cytosine residues or guanine residues.

[5] The production method for a cell in which only one allele is genome-edited according to any one of [1] to [4], the method further including: a step of introducing (C) a donor vector into the cell.

[6] The production method for a cell in which only one allele is genome-edited according to any one of [1] to [5], in which the Cas protein is a Cas9 protein.

[7] A guide RNA in which one or more nucleotide residues are added to a 5'-end of a spacer sequence.

[8] The guide RNA according to [7], in which the spacer sequence has single-base or multiple-base mismatches with respect to a target sequence.

[9] An expression vector for the guide RNA according to [7] or [8].

[10] The expression vector according to [9], in which the expression vector further causes a Cas protein to be expressed.

[11] The expression vector according to [10], in which the Cas protein is a Cas9 protein.

[12] A production kit for a cell in which only one allele is genome-edited, the production kit including: (A) at least one selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector for the guide RNA of (a1) or (a2).

[13] The production kit according to further including: (B) at least one selected from the group consisting of a Cas protein and an expression vector for the Cas protein.

[14] A prediction method for a genome editing pattern, the method including: a step (i) of introducing a guide RNA or an expression vector for the guide RNA, and a Cas protein or an expression vector for the Cas protein into a cell to perform genome editing; a step (ii) of extracting DNA from the genome-edited cell; a step (iii) of amplifying a DNA fragment containing a target region from the DNA; a step (iv) of performing sequence analysis on the amplified DNA fragment to obtain an indel induction ratio (P) of the target region; and a step (v) of obtaining a monoallelic indel induction ratio (mono) and a biallelic indel induction ratio (bi) from Formulas (m) or (m1) and (b) or (b1).

$$mono=2\times P\times(1-P) \tag{m}$$

$$bi=P^2 \tag{b}$$

$$mono=-1.303P^2+1.2761P+0.0274 \tag{m1}$$

$$bi=0.6515P^2+0.3619P-0.0137 \tag{b1}$$

[15] A cell including: a chimeric gene in which a localized protein coding sequence, a cleavage site, and a first fluorescent protein coding sequence are linked in-frame in this order, at one allele; and a chimeric gene in which the localized protein coding sequence, the cleavage site, and a second fluorescent protein coding sequence are linked in-frame in this order, at the other allele.

[16] An analysis method for a genome editing pattern, the method including: a step (I) of introducing a guide RNA targeting the cleavage site or an expression vector for the guide RNA, and a Cas protein or an expression vector for the Cas protein into the cell according to to perform genome editing; a step (II) of analyzing a fluorescence pattern of the cell after the step (I); and a step (III) of determining a genome editing pattern based on the fluorescence pattern analyzed in the step (II).

Advantageous Effects of Invention

According to the present invention, a production method for a cell in which only one allele is genome-edited; and a guide RNA, an expression vector, and a kit which can be used in the method are provided. Furthermore, a prediction method for a genome editing pattern, an analysis method for a genome editing pattern, and a cell that can be used in the analysis method are provided.

BRIEF DESCRIPTION OF DRAWINGS

FIG. 1A is a diagram showing a genetic constitution of an AIMS cell produced in Examples.

FIG. 1B is a diagram showing a method of evaluating an indel by the AIMS.

FIG. 1C shows a P2A peptide coding sequence used to produce AIMS cells in Examples, and an aP2A sequence in which a silent mutation was introduced into the above sequence.

FIG. 3A shows an example of a spacer sequence used in Examples.

FIG. 3B shows results of performing indel pattern analysis using a Tbx3-P2A-AIMS as AIMS cells.

FIG. 4A shows an example of sgRNA used in Examples.

FIG. 4B shows results of performing indel pattern analysis using a Cdh1-P2A-AIMS as AIMS cells.

FIG. 4C shows results of performing indel pattern analysis using a Cdh1-P2A-AIMS as AIMS cells.

FIG. 4D shows results of investigating whether introduction percentages of a biallelic indel and a monoallelic indel are changed by changing an amount of an sgRNA expression plasmid transfected.

FIG. 4E shows results of investigating whether introduction percentages of a biallelic indel and a monoallelic indel are changed by changing an amount of an sgRNA expression plasmid transfected. A Cas9 and puromycin-resistant gene expression plasmid and an sgRNA expression plasmid were separated into separate plasmids, and only an amount of the sgRNA expression plasmid was changed.

FIG. 4F shows results of performing genome editing with Rosa26 and an albumin genes (Alb) as targets. sgRNA in which cytosine (C) was added to the 5'-end of a spacer sequence was used.

FIGS. 5A to 5C show results of evaluating, using AIMS cells, introduction percentages of homologous recombination not including indels. FIG. 5A is a diagram showing an outline of a method used in Example 5.

FIG. 5B shows results of performing homologous recombination using sgRAN containing a spacer sequence having a 1-base mismatch.

FIG. 5C shows results of performing homologous recombination using sgRAN in which cytosine was added to the 5'-end of a spacer sequence.

FIG. 6A shows results of using sgRNA having a 1-base mismatch with respect to a target sequence.

FIG. 6B shows results of using sgRNA containing a spacer sequence which has a 1-base mismatch with respect to a target sequence and in which 10 cytosines were added to the 5'-end.

FIG. 6C shows results of using sgRNA containing a spacer sequence which has a 1-base mismatch with respect to a target sequence and in which 25 cytosines were added to the 5'-end.

FIG. 8A shows an operation protocol of Pre-Demo-Prediction.

FIG. 8B shows prediction values of Pre-Demo-Prediction (left figure) and actual measurement values (right figure).

FIG. 9A shows results of calculating an indel induction ratio (P) by Formula (1) described in Example 7 based on data of FIGS. 6A to 6C.

FIG. 9B shows results of verifying an effect of inhibiting an off-target action by adding cytosine to the 5'-end of a spacer sequence. They are results of verifying indels in an on-target region, and an MFAP1 gene region that is an off-target region (GAGTCtaAGCAGAAGAAGAA: SEQ ID NO: 91; where portions different from a target sequence in an EMX1 gene are shown in small letters) by introducing, into HEK 293T, an expression vector for sgRNA in which 0, 10, or 25 cytosines were added to the 5'-end of a spacer sequence with respect to the target sequence (GAGTCCGAGCAGAAGAAGAA: 5th to 24th of SEQ ID NO: 83) in the EMX1 gene.

FIG. 9B shows results of verifying an effect of inhibiting an off-target action by adding cytosine to the 5'-end of a spacer sequence. Under the same conditions as in FIG. 9B, the number of cytosines added to the 5'-end of the spacer sequence was set to 0, 5, 10, 15, 20, 25, or 30.

FIG. 10A shows an outline of a repair method for an FOP genetic disease mutation.

FIG. 10B shows results of evaluating HDR induction efficiency when HDR for repairing a mutant allele (R206H) was induced using human iPS cells having an FOP genetic disease mutation (wt/R206H).

FIG. 10C shows results of evaluating efficiency of indel introduction by genome editing with a mutant allele (R206H) as a target in human iPS cells having an FOP genetic disease mutation (wt/R206H).

FIG. 11A shows an outline of an induction method for an FOP genetic disease mutation.

FIG. 11B shows results of evaluating HDR induction efficiency when HDR for inducing a mutant allele (R206H) was induced using mouse ES cells (wt/wt).

FIG. 11C shows results of evaluating efficiency of indel introduction by genome editing with an Acvr1 gene (wt) as a target in mouse ES cells (wt/wt).

FIG. 11D is a photograph showing an abnormal bone (arrow) formed in a chimeric mouse produced by microinjection of mouse ES cells, which had an FOP genetic disease mutation (wt/R206H) and produced by HDR induction, into a fertilized mouse egg.

FIG. 15 shows results of in vitro cleavage assay with sgRNA in which 0, 10, or 25 cytosines were added.

DESCRIPTION OF EMBODIMENTS

Definitions

Figure 1A:
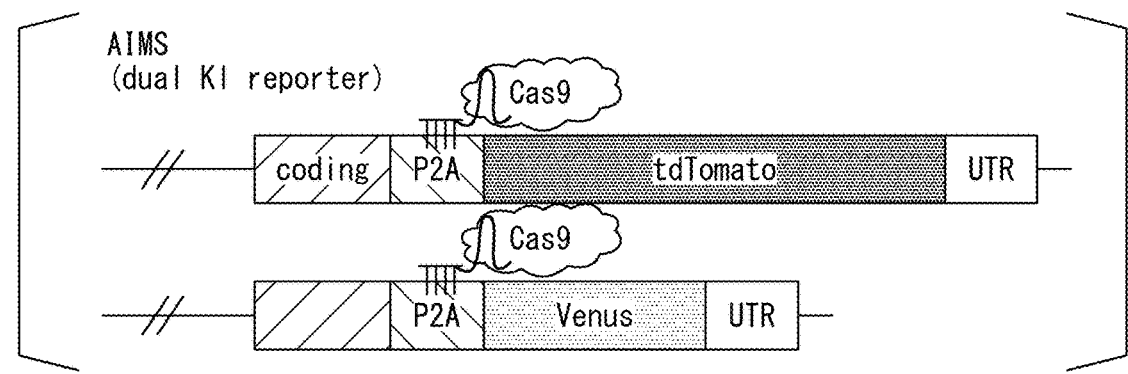
FIGS. 1A to 1C are diagrams showing an outline of an AIMS constructed in Examples.

In the present specification, the terms "polynucleotide" and "nucleic acid" are used interchangeably and refer to a nucleotide polymer in which nucleotides are bonded by phosphodiester bonds. The "polynucleotide" and "nucleic acid" may be DNA, may be RNA, or may be composed of a combination of DNA and RNA. Furthermore, the "polynucleotide" and "nucleic acid" may be a polymer of natural nucleotides, may be a polymer of natural nucleotides and non-natural nucleotides (such as nucleotides (for example, phosphorothioate backbones) in which at least one of analogs, base moieties, sugar moieties, and phosphate moieties of natural nucleotides have been modified), or may be a polymer of non-natural nucleotides.

In the present specification, a base sequence of the "polynucleotide" or "nucleic acid" is described by a generally accepted single letter code unless otherwise specified. A base sequence is described from the 5'-side to the 3'-side unless otherwise specified.

In the present specification, nucleotide residues constituting the "polynucleotide" or "nucleic acid" may be simply described as adenine, thymine, cytosine, guanine, or uracil, or single letter codes thereof.

In the present specification, the term "gene" refers to a polynucleotide containing at least one open reading frame that encodes a specific protein. The gene can contain both exons and introns.

In the present specification, the terms "polypeptide," "peptide," and "protein" are used interchangeably and refer to a polymer of amino acids bonded by amide bonds. The "polypeptide," "peptide," or "protein" may be a polymer of natural amino acids, may be a polymer of natural amino acids and non-natural amino acids (such as chemical analogs and modified derivatives of natural amino acids), or may be a polymer of non-natural amino acids. An amino acid sequence is described from the N-terminus side to the C-terminus side unless otherwise specified.

In the present specification, the term "alleles" refer to a pair of genes present at the same loci on a pair of chromosomes or a pair of base sequences present at the same loci. In the pair of genes, the genes do not necessarily have to be allelic genes, and in the pair of base sequences, the base sequences do not necessarily have to be different from each other. The term "both alleles" refers to both genes in the pair of genes or both base sequences in the pair of base sequences, and the term "one allele" refers to any one gene in the pair of genes or any one base sequence in the pair of base sequences.

In the present specification, the term "genome editing" refers to induction of a mutation at a desired location (target region) on a genome. Genome editing may include use of a nuclease engineered to cleave DNA of a target region. Typically, use of a site-specific nuclease induces double-strand breaks (DSBs) in DNA of a target region, and thereafter, the genome is repaired by an endogenous process of a cell, such as Homologous Directed Repair (HDR) and Non-Homologous End-Joining Repair (NHEJ). NHEJ is a repair method in which ends cleaved by double-strand breaks are linked without using template DNA for repair, and insertion and/or deletion (indel) is induced during the repair at a high frequency. HDR is a repair mechanism using template DNA for repair, and it is also possible to introduce a desired mutation into a target region. Preferred examples of genome editing techniques include a CRISPR/Cas system.

In the present specification, the term "template DNA for repair" refers to DNA used for repairing double-strand breaks in DNA that can be homologously recombined with DNA around a target region.

In the present specification, the term "donor vector" refers to exogenous DNA used as template DNA for repair. The donor vector contains a base sequence adjacent to a target region as a homology arm. In the present specification, a homology arm consisting of a base sequence adjacent to the 5'-side of a target region may be referred to as a "5'-arm," and a homology arm consisting of a base sequence adjacent to the 3'-side of a target sequence may be referred to as a "3'-arm." The donor vector can contain a desired base sequence between the 5'-arm and the 3'-arm. A length of each of the homology arms is preferably 3 kb or longer, and is generally about 5 to 10 kb. Lengths of the 5'-arm and the 3'-arm may be the same as or different from each other, but they are preferably the same.

In the present specification, the term "safe harbor region" refers to a region on a genome which has been verified to enable insertion of foreign DNA without exerting any detrimental effects on cells. As the safe harbor region, for example, AAVS1 in humans, Rosa26 in mice, and the like are known.

In the present specification, the term "Cas protein" refers to CRISPR-associated protein. In a preferred embodiment, the Cas protein forms a complex with a guide RNA to exhibit endonuclease activity or nickase activity. The Cas protein is not particularly limited, and examples thereof include a Cas9 protein, a Cpf1 protein, a C2c1 protein, a C2c2 protein, a C2c3 protein, and the like. As long as the Cas protein exhibits endonuclease activity or nickase activity in cooperation with a guide RNA, the Cas protein includes wild-type Cas proteins and their homologs (paralogs and orthologs), and their mutants.

The Cas protein is a protein involved in a class 2 CRISPR/ Cas system in a preferred embodiment, and is more preferably a protein involved in a type II CRISPR/Cas system. Preferred examples of the Cas protein include a Cas9 protein.

In the present specification, the term "Cas9 protein" refers to a Cas protein involved in the type II CRISPR/Cas system. The Cas9 protein forms a complex with a guide RNA to exhibit the activity of cleaving DNA of a target region in cooperation with the guide RNA. As long as the Cas9 protein has the above-mentioned activity, the Cas9 protein includes wild-type Cas9 proteins and their homologs (paralogs and orthologs), and their mutants. The wild-type Cas9 protein has a RuvC domain and an HNH domain as nuclease domains, but the Cas9 protein in the present specification may be a protein in which any one of a RuvC domain and an HNH domain is inactivated.

The organism species from which the Cas9 protein is derived is not particularly limited, and preferred examples thereof include bacteria belonging to the genus *Streptococcus*, the genus *Staphylococcus*, the genus *Neisseria*, or the genus *Treponema*. More specifically, Cas9 proteins derived from *S. pyogenes, S. thermophilus, S. aureus, N. Meningitidis, T. denticola*, and the like are preferred examples. In a preferred embodiment, the Cas9 protein is a Cas9 protein derived from *S. pyogenes*.

Information on amino acid sequences of various Cas proteins and coding sequences thereof can be obtained on various databases such as GenBank and UniProt. For example, for an amino acid sequence of a Cas9 protein of *S. pyogenes*, those registered in UniProt as accession number Q99ZW2, and the like can be used. An example of a coding sequence of the Cas9 protein of *S. pyogenes* is set forth in SEQ ID NO: 9. A base sequence set forth in SEQ ID NO: 9 is a base sequence in which 3×Flag and a nuclear localization signal are added to the 5'-end of the Cas9 protein of *S. pyogenes*, and a nuclear localization signal is added to the 3'-end.

In the present specification, the terms "guide RNA" and "gRNA" are used interchangeably and refer to RNA that can form a complex with a Cas protein to induce the Cas protein to a target region. In a preferred embodiment, the guide RNA contains CRISPR RNA (crRNA) and trans-activating CRISPR RNA (tracrRNA). The crRNA is involved in bonding to a target region on a genome, and the tracrRNA is involved in bonding to a Cas protein. In a preferred embodiment, crRNA contains a spacer sequence and a repeated sequence, where the spacer sequence is bonded to a complementary strand of a target sequence in a target region. In a preferred embodiment, tracrRNA contains an anti-repeated sequence and a 3'-tail sequence. The anti-repeated sequence has a sequence complementary to the repeated sequence of crRNA and forms a base pair with the repeated sequence, and the 3'-tail sequence generally forms three stem loops.

The guide RNA may be a single-stranded guide RNA (sgRNA) in which the 5'-end of tracrRNA is linked to the 3'-end of crRNA, or may be a guide RNA which has crRNA and tracrRNA as individual RNA molecules and in which a repeated sequence and an anti-repeated sequence form a base pair. In a preferred embodiment, the guide RNA is an sgRNA.

A repeated sequence of crRNA and a sequence of tracrRNA can be appropriately selected according to the type of Cas protein, and those derived from the same bacterial species as a Cas protein can be used.

For example, in a case of using a Cas9 protein derived from *S. pyogenes*, a length of sgRNA can be about 50 to 220 nucleotides (nt), is preferably about 60 to 180 nt, and is more preferably about 80 to 120 nt. A length of crRNA can be about 25 to 70 bases, including spacer sequences, and is preferably about 25 to 50 nt. A length of the tracrRNA can be about 10 to 130 nt, and is preferably about 30 to 80 nt.

A repeated sequence of crRNA may be the same as that in bacterial species from which a Cas protein is derived, or may be a repeated sequence from which a part of the 3'-end has been removed. tracrRNA may have the same sequence as that of mature tracrRNA in bacterial species from which a Cas protein is derived, or may be an end-cleaved type in which the 5'-end and/or the 3'-end of mature tracrRNA has been cleaved. For example, tracrRNA can be an end-cleaved type in which about 1 to 40 nucleotide residues have been removed from the 3'-end of mature tracrRNA. Furthermore, tracrRNA can be an end-cleaved type in which about 1 to 80 nucleotide residues have been removed from the 5'-end of mature tracrRNA. Furthermore, tracrRNA can be, for example, an end-cleaved type in which about 1 to 20 nucleotide residues have been removed from the 5'-end, and about 1 to 40 nucleotide residues have been removed from the 3'-end.

Various crRNA repeated sequences and tracrRNA sequences have been proposed for sgRNA design, and those skilled in the art can design sgRNA based on known techniques (for example, Jinek et al. (2012) Science, 337, 816-21; *Mali* et al. (2013) Science, 339:6121, 823-6; Cong et al. (2013) Science, 339:6121, 819-23; Hwang et al. (2013) Nat. Biotechnol. 31:3, 227-9; Jinek et al. (2013) eLife, 2, e00471).

In the present specification, the term "target sequence" refers to a DNA sequence in a genome which is a subject of cleavage by a Cas protein. In a case of using a Cas9 protein as the Cas protein, the target sequence is required to be a sequence adjacent to the 5'-side of a protospacer adjacent motif (PAM). For the target sequence, a sequence of 17 to 30 bases (preferably 18 to 25 bases, more preferably 19 to 22 bases, and even more preferably 20 bases) adjacent immediately before the 5'-side of PAM is generally selected. For target sequence design, it is possible to use known design tools such as CRISPR DESIGN (crispr.mit.edu/).

In the present specification, the term "target region" refers to a genomic region that contains a target sequence and a complementary strand thereof.

In the present specification, the terms "protospacer adjacent motif" and "PAM" are used interchangeably and refer to a sequence recognized by a Cas protein in the case of DNA cleavage by the Cas protein. A sequence and a location of PAM vary according to the type of Cas protein. For example, in a case of a Cas9 protein, PAM is required to be adjacent immediately after the 3'-side of a target sequence. Sequences of PAM corresponding to a Cas9 protein vary according to bacterial species from which the Cas9 protein is derived. For example, PAM corresponding to a Cas9 protein of *S. pyogenes* is "NGG," PAM corresponding to a Cas9 protein of *S. thermophilus* is "NNAGAA," PAM corresponding to a Cas9 protein of *S. aureus* is "NNGRRT" or "NNGRR (N)," PAM corresponding to a Cas9 protein of *N. meningitidis* is "NNNNGATT," and PAM corresponding to a Cas9 protein of *T. denticola* is "NAAAAC" (where "R" is A or G; and "N" is A, T, G, or C).

In the present specification, the terms "spacer sequence" and "guide sequence" are used interchangeably and refer to a sequence contained in a guide RNA which is a sequence that can be bonded to a complementary strand of a target sequence. The spacer sequence is generally the same sequence as a target sequence (however, T in the target sequence is U in the spacer sequence). In an embodiment of the present invention, the spacer sequence can have single-base or multiple-base mismatches with respect to a target sequence. In a case where multiple-base mismatches are contained, the mismatches may be contained at adjacent locations or may be contained at separated locations. In a preferred embodiment, the spacer sequence may have 1-base to 5-base mismatches with respect to a target sequence. In a particularly preferred embodiment, the spacer sequence may have a 1-base mismatch with respect to a target sequence.

In a guide RNA, a spacer sequence is disposed on the 5'-side of crRNA.

In the present specification, the term "mismatch" refers to a case in which a spacer sequence has a base different from that of a target sequence, or refers to this different base. For example, when the sentence a "spacer sequence has a 1-base mismatch," it means that the spacer sequence differs at 1 base as compared with a target sequence.

In the present specification, the term "indel" means insertion and/or deletion.

In the present specification, the term "biallelic indel" refers to a state in which an indel occurred in target regions of both alleles by genome editing.

In the present specification, the term "monoallelic indel" refers to a state in which an indel occurred only in a target region of one allele by genome editing.

In the present specification, the term "frame-shift indel" refers to an indel in which a frame-shift occurs.

In the present specification, the term "in-frame indel" refers to an indel in which a frame-shift does not occur.

In the present specification, the term "AIMS" means Allele-specific Indel Monitor System and refers to a technique capable of detecting an indel in an allele-specific manner.

In the present specification, the term "AIMS cell" means a cell constructed to perform AIMS and refers to a cell capable of detecting an indel in an allele-specific manner.

In the present specification, the term "chimeric gene" refers to a polynucleotide in which coding sequences of two or more different proteins are linked in-frame. The term "chimeric protein" refers to a protein expressed from a chimeric gene.

In the present specification, the term "localized protein" refers to a protein that is present to be localized to a certain portion of a cell (for example, a nucleus or a cell membrane). The term "nucleus-localized protein" means a protein that is present to be localized in a nucleus, and the term "cell membrane-localized protein" means a protein that is present to be localized in a cell membrane.

In the present specification, the term "cleavage site" refers to an amino acid sequence or a nucleotide sequence which can be recognized by a cleavage enzyme and/or can be divided, and thereby directed to division. Typically, at a cleavage site, a polypeptide chain is cleaved by hydrolysis of one or more peptide bonds that bond amino acids. Furthermore, at a cleavage site, a polynucleotide chain is cleaved by hydrolysis of one or more phosphodiester bonds between nucleotides. Cleavage of peptide bonds or phosphodiester bonds may be derived from chemical or enzymatic cleavage. In the case of a polynucleotide chain, enzymatic cleavage refers to cleavage of a polynucleotide which is achieved by, for example, a restriction endonuclease (such as type I, type II, type III, type IV, or artificial restriction enzymes). In the case of a polypeptide chain, enzymatic cleavage refers to cleavage of a polypeptide which is achieved by a proteolytic enzyme, and examples thereof include, but are not limited to, endopeptidases, exopeptidases, proteases (for example, serine proteases, cysteine proteases, metalloproteases, threonine proteases, aspartate proteases, and glutamic proteases), and the like. Typically, enzymatic cleavage occurs due to self-cleavage or is achieved by an independent proteolytic enzyme. Enzymatic cleavage of a protein or polypeptide can occur either at the same time as translation or after translation. Accordingly, the term "endopeptidase cleavage site" used in the present specification refers to a cleavage site within an amino acid sequence, where this sequence is cleaved or can be cleaved by endopeptidases (for example, trypsin, pepsin, elastase, thrombin, collagenase, furin, thermolysin, endopeptidase V8, and cathepsin). A cleavage site may be cleaved by an autoprotease, that is, a protease that cleaves a peptide bond within the same protein molecule and also the protease. Examples of such autoproteases include NS2 protease of Flavivirus or VP4 protease of Birnaviridae. Alternatively, the term "cleavage site" refers to an amino acid sequence or a nucleotide sequence which interferes with formation of peptide bonds between amino acids or phosphodiester bonds between nucleotides. For example, formation of peptide bonds is interfered by self-processing that occurs at the same time as translation of polypeptides resulting in two inconsecutive translated products derived from a single translation event in a single open reading frame. Typically, such self-processing is achieved by a "ribosomal skipping" that is caused by a pseudo stop-codon sequence that induces a translation complex to move from one codon to the next without forming a peptide bond. Examples of sequences that induce ribosomal skipping include, but are not limited to, viral 2A peptides or 2A-like peptides (where both are collectively referred to as "2A peptides" in the present specification) which are used by several families of viruses including picornaviruses, insect viruses, aphthovirus (Aphtoviridae), rotavirus, and *trypanosoma*. The most widely known are 2A peptides of rhinovirus and foot-and-mouth disease virus of the family Picornaviridae, which are typically used to produce multiple polypeptides from a single ORF.

Accordingly, the term "self-cleavage site" used in the present specification refers to a cleavage site within in an amino acid sequence or a nucleotide sequence, in which these sequences are cleaved or can be cleaved without being associated with any additional molecules, or in which formation of peptide bonds or phosphodiester bonds within the sequences is interfered (through, for example, self-processing at the same time as translation as described above) in a final step. It is understood that a cleavage site typically contains a few amino acids or is encoded by a few codons (for example, in such cases, the "cleavage site" is not translated into protein but causes interruption of translation). Therefore, the cleavage site also serves the purpose of a peptide linker, that is, steric separation of two peptides. Accordingly, in some embodiments, the "cleavage site" is also a peptide linker and also provides the above-described cleavage function. In these embodiments, the cleavage site may include additional N- and/or C-terminal amino acids.

In the present specification, the term "2A peptide" refers to a viral 2A peptide or 2A-like peptide. The 2A peptide is a peptide that is cleaved by a peptidase or ribosomal skipping mechanism. Examples of 2A peptides include a 2A peptide (F2A) derived from Foot-and-mouth disease virus (FMDV), a 2A peptide (E2A) derived from Equine rhinitis A virus (ERAV), a 2A peptide (P2A) derived from Porcine teschovirus (PTV-1), a 2A peptide (T2A) derived from Thosea asigna virus (TaV), and the like.

In the present specification, the term "genome editing pattern" refers to a induction state of genome editing in each allele of a target region of a cell that is a genome editing subject. That is, it means a state in which genome editing is induced in both alleles or genome editing is induced only in one allele.

In the present specification, the phrase "functionally linked" used relating to a polynucleotide means that a first base sequence is disposed sufficiently close to a second base sequence, and the first base sequence can affect the second base sequence or a region under control of the second base sequence. For example, when a polynucleotide is functionally linked to a promoter, this means that this polynucleotide is linked to be expressed under control of the promoter.

In the present specification, the term "expressible state" refers to a state in which a polynucleotide can be transcribed within a cell into which the polynucleotide has been introduced.

In the present specification, the term "expression vector" refers to a vector containing a subject polynucleotide, and having a system that causes the subject polynucleotide to become an expressible state within the cell into which the vector has been introduced. For example, an "expression vector for a Cas protein" means a vector capable of expressing the Cas protein within a cell into which the vector has been introduced. Furthermore, for example, an "expression vector for a guide RNA" means a vector capable of expressing the guide RNA within a cell into which the vector has been introduced.

In the present specification, the term "silent mutation" refers to a gene mutation in which an amino acid sequence of a protein encoded does not change.

In the present specification, a sequence identity (or homology) between base sequences or amino acid sequences is obtained as a proportion of matching bases or amino acids with respect to the entire base sequences or amino acid sequences by juxtaposing two base sequences or amino acid sequences while putting a gap in parts coinciding with an insertion and a deletion so that corresponding bases or amino acids match most, and removing gaps in the obtained alignment. The sequence identity between base sequences or amino acid sequences can be obtained using various homology search software known in the technical field. For example, a sequence identity value of base sequences can be obtained by calculation based on alignment obtained by known homology search software BLASTN, and a sequence identity value of amino acid sequences can be obtained by calculation based on alignment obtained by known homology search software BLASTP.

[Production Method for Cell in which Only One Allele is Genome-Edited]

In one embodiment, the present invention provides a production method for a cell in which only one allele is genome-edited, the method including: a step of introducing, into the cell, (A) at least one selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector for the guide RNA of (a1) or (a2), and (B) at least one selected from the group consisting of a Cas protein and an expression vector for the Cas protein.

<(A) Guide RNA>

In the production method of the present embodiment, at least one is used, which is selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector for the guide RNA of (a1) or (a2).

<<Guide RNA of (a1)>>

The guide RNA of (a1) is a guide RNA in which one or more nucleotide residues are added to a 5'-end of a spacer sequence. By performing genome editing using this guide RNA, a proportion of genome editing in only one allele is increased, and thereby it is possible to produce cells in which only one allele is genome-edited.

The spacer sequence is not particularly limited and may be any spacer sequence as long as it targets an arbitrary target sequence. A length of the spacer sequence may be any length as long as it is a length corresponding to a target sequence, and a sequence of 17 to 30 bases, preferably 18 to 25 bases, more preferably 19 to 21 bases, and even more preferably 20 bases is generally selected.

In general, a spacer sequence is the same sequence as a target sequence (however, "T" in the target sequence becomes "U" in the spacer sequence), but a spacer sequence may have a mismatch as long as it has a bonding ability with respect to a complementary strand of a target sequence. A mismatch on the 5'-side of a spacer sequence is generally acceptable. In the production method of the present embodiment, a spacer sequence having a 1-base mismatch with respect to a target sequence is preferable, as in the guide RNA of (a2) to be described later.

The number of nucleotide residues added to the 5'-end of a spacer sequence (hereinafter, may be referred to as "additional nucleotide residue") is 1 or more and is not particularly limited. Examples thereof include a range of 1 to 50. The number of nucleotide residues added can be appropriately set depending on the type of spacer sequence. For example, the number of nucleotide residues added can be 5 or more, 10 or more, 15 or more, 20 or more, 25 or more, and the like. When the number of additional nucleotide residues is equal to or greater than the lower limit value, it is possible to further increase a proportion of genome editing in only one allele. An upper limit of the number of additional nucleotide residues is not particularly limited, but for example, it can be 50 or less, is preferably 40 or less, and is more preferably 35 or less, because then a proportion of genome editing in only one allele does not change. A preferred range of the number of additional nucleotide residues is, for example, 5 to 50, and is preferably 5 to 40, 5 to 35, 10 to 40, 10 to 35, 15 to 35, 20 to 30, and the like.

The type of additional nucleotide residue is not particularly limited, but for example, all nucleotide residues can be the same nucleotide residues. For example, an additional nucleotide residue can be selected from the group consisting of polyadenine (polyA), polyuracil (polyU), polycytosine (polyC), and polyguanine (polyG). Among them, the type of additional nucleotide residue is preferably polyC (all cytosine residues) or polyG (all guanine residues) and is more preferably polyC because then a proportion of genome editing in only one allele is improved.

In a case of using an expression vector encoding the guide RNA of (a1) such as the expression vector of (a3) to be described later, an additional polynucleotide residue generally does not have a complementary sequence of a terminator sequence at which transcription from a promoter used is stopped. For example, in a case of using a U6 promoter, because transcription stops when there are 5 consecutive thymines, an additional nucleotide residue generally does not have a sequence of 5 or more consecutive uracils.

<<Guide RNA of (a2)>>

The guide RNA of (a2) is a guide RNA containing a spacer sequence having single-base or multiple-base mismatches with respect to a target sequence. By performing genome editing using this guide RNA, a proportion of genome editing in only one allele is increased, and thereby it is possible to produce cells in which only one allele is genome-edited.

The spacer sequence of the guide RNA of (a2) has single-base or multiple-base mismatches with respect to an arbitrary target sequence. The multiple-base mismatches are, for example, 2-base to 5-base mismatches, preferably 2-base to 4-base mismatches, more preferably 2-base or 3-base mismatches, and even more preferably 2-base mismatches. A length of the spacer sequence is the same as that of the guide RNA of (a1) above, but it is particularly preferably 20 bases.

A location at which the spacer sequence has single-base or multiple-base mismatches with respect to a target sequence is not particularly limited. For example, in a case where the spacer sequence is 20 bases, a mismatch may be present at any of the 1 st to 20th bases counted from the 3'-end side to the 5'-end side. For example, the spacer sequence can have a mismatch at the 1st to 17th bases. When the spacer sequence has a 1-base mismatch at the above-mentioned range, it is possible to further increase a proportion of genome editing in only one allele. As an example, the spacer sequence can have a mismatch at 1 base or multiples bases selected from the group consisting of the 2nd to 6th bases, the 8th and 9th bases, and the 15th to 17th bases, which are all counted from the 3'-end side to the 5'-end side.

A base relating to a mismatched base is not particularly limited as long as it is a base different from a base in a target sequence. A mismatched base in the spacer sequence can be a pyrimidine base (cytosine or uracil) when a base in a target sequence is, for example, a purine base (adenine or guanine). Similarly, a mismatched base in the spacer sequence can be a purine base (adenine or guanine) when a base in a target sequence is, for example, a pyrimidine base (cytosine or thymine). For example, a mismatched base in the spacer sequence can be uracil when a base in a target sequence is adenine, can be adenine when a base in a target sequence is thymine, can be cytosine when a base in a target sequence is guanine, or can be guanine when a base in a target sequence is cytosine.

<<Guide RNA (a12) Having Characteristics of (a1) and (a2)>>

A guide RNA used in the production method of the present embodiment may have the characteristics of the guide RNAs of (a1) and (a2) described above. That is, the guide RNA may be a guide RNA in which one or more nucleotide residues are added to a 5'-end of a spacer sequence that is a spacer sequence having single-base or multiple-base mismatches with respect to a target sequence.

By combining the characteristics of (a1) and (a2) described above, it is possible to improve a proportion of genome editing in only one allele. The number and type of additional nucleotide residues are the same as the exemplary examples in "<<Guide RNA of (a1)>>" described above. Furthermore, a location and the type of mismatched base are the same as the exemplary examples in "<<Guide RNA of (a2)>>" described above.

<<Expression Vector (a3) for Guide RNA>>

In the production method of the present embodiment, an expression vector for the guide RNA of (a1), (a2), or (a12) described above may be used instead of the guide RNA of (a1), (a2), or (a12) described above. In a preferred embodiment, the production method of the present embodiment uses the expression vector for the guide RNA of (a1), (a2), or (a12) described above.

The expression vector for the guide RNA of (a1), (a2), or (a12) described above preferably contains a sequence encoding the guide RNA of (a1), (a2), or (a12) described above, and a promoter controlling expression of this guide RNA coding sequence. In the expression vector, the guide RNA coding sequence is functionally linked to the promoter.

The promoter is not particularly limited, and it is possible to use, for example, a pol II promoter, but a pol III promoter is preferable from the viewpoint of causing more accurate transcription of a relatively short RNA. The pol III promoter is not particularly limited, and examples thereof include mouse and human U6-snRNA promoters, a human H1-RNase P RNA promoter, a human valine-tRNA promoter, and the like. In a case of using a U6 promoter, the 5'-end of a guide RNA is preferably "G" for initiation of transcription. Therefore, in a case where a guide RNA is the guide RNA of (a1) or (a12) described above, it is preferable to further add "G" to the 5'-end of 5 to 50 nucleotide residues added to the 5'-end of a spacer sequence. Furthermore, in a case where a guide RNA is the guide RNA of (a2) described above, it is preferable to select a spacer sequence in which the 5'-end is "G" or to add "G" to the 5'-end of a spacer sequence.

In addition to the guide RNA coding sequence and the promoter therefor, as desired, the expression vector may contain an enhancer, a polyA addition signal, a marker gene, a replication origin, a gene encoding a protein that is bonded to a replication origin to control replication, and the like. The "marker gene" refers to a gene that enables sorting and selection of cells by introducing the marker gene into cells. Specific examples of marker genes include drug-resistant genes, fluorescent protein genes, luminescent enzyme genes, color-developing enzyme genes, and the like. One kind of these examples may be used alone, or two or more kinds thereof may be used in combination. Specific examples of the drug-resistant genes include puromycin-resistant genes, geneticin-resistant genes, neomycin-resistant genes, tetracycline-resistant genes, kanamycin-resistant genes, zeocin-resistant genes, hygromycin-resistant genes, chloramphenicol-resistant genes, and the like. Specific examples of the fluorescent protein genes include green fluorescent protein (GFP) genes, yellow fluorescent protein (YFP) genes, red fluorescent protein (RFP) genes, and the like. Specific examples of the luminescent enzyme genes include luciferase genes and the like. Specific examples of the color-developing enzyme genes include β-galactosidase genes, β-glucuronidase genes, alkaline phosphatase genes, and the like.

The type of expression vector is not particularly limited, and a known expression vector can be used.

Examples of expression vectors include plasmid vectors, virus vectors, and the like.

A plasmid vector is not particularly limited as long as it is a plasmid vector that enables expression within a cell that is a genome editing subject. For example, in the case of animal cells, a generally used plasmid vector can be used as a plasmid vector for expression in animal cells. Examples of plasmid vectors for expression in animal cells include, but are not limited to, pX459, pA1-11, pXT1, pRc/CMV, pRc/RSV, pcDNAI/Neo, and the like.

Examples of virus vectors include retrovirus (including lentivirus) vectors, adenovirus vectors, adeno-associated virus vectors, Sendai virus vectors, herpesvirus vectors, vaccinia virus vectors, poxvirus vectors, poliovirus vectors, Sindbis virus vectors, rhabdovirus vectors, paramyxovirus vectors, orthomyxovirus vectors, and the like.

Among them, a plasmid vector is preferable as the expression vector.

< (B) Cas Protein>

<<Cas Protein>>

The Cas protein is not particularly limited as long as it is used in the CRISPR/Cas system. For example, it is possible to use various types of Cas protein that can form a complex with a guide RNA, guided to a target region by the guide RNA, and cleave double strands of DNA of the target region.

In the production method of the present embodiment, the Cas protein is preferably a Cas9 protein, and is more preferably a Cas9 protein of *S. pyogenes*.

The Cas protein may be a mutant of a wild-type Cas protein as long as it forms a complex with a guide RNA and exhibits endonuclease activity or nickase activity (hereinafter referred to as "Cas protein activity"). Examples of mutants of a Cas protein include the following proteins (b1) or (b2).

(b1) A protein which consists of an amino acid sequence having, for example, 85% or more, preferably 90% or more, more preferably 95% or more, and even more preferably 98% or more sequence identity with an amino acid sequence of a wild-type Cas protein, and which has the Cas protein activity.

(b2) A protein which consist of an amino acid sequence in which one or multiple (for example, 2 to 100, preferably 2 to 50, more preferably 2 to 20, even more preferably 2 to 10, and still more preferably 2 to 5, and particularly preferably 2) amino acids have been substituted, deleted, added, or inserted from an amino acid sequence of a wild-type Cas protein, and which has the Cas protein activity.

<<Expression Vector for Cas Protein>>

In the production method of the present embodiment, an expression vector for a Cas protein may be used instead of the Cas protein. In a preferred embodiment, the production method of the present embodiment uses the expression vector for a Cas protein.

The expression vector for a Cas protein preferably contains a Cas protein coding sequence, and a promoter controlling expression of the Cas protein coding sequence. In the expression vector, the Cas protein coding sequence is functionally linked to the promoter.

The promoter is not particularly limited, and for example, various pol II promoters can be used. The pol II promoter is not particularly limited, and examples thereof include CMV promoters, EF1 promoters, SV40 promoters, MSCV promoters, hTERT promoters, β-actin promoters, CAG promoters, CBh promoters, and the like.

In addition to the Cas protein coding sequence and the promoter therefor, as desired, the expression vector may contain an enhancer, a polyA addition signal, a marker gene, a replication origin, a gene encoding a protein that is bonded to a replication origin to control replication, and the like. Examples of marker genes include the same examples described above.

The type of expression vector is not particularly limited, and a known expression vector can be used.

Examples of expression vectors include plasmid vectors, virus vectors, and the like. Examples of these vectors include the same examples described above.

Among them, a plasmid vector is preferable as the expression vector.

The Cas protein coding sequence contained in the expression vector may be codon-optimized according to the organism species from which a cell into which the expression vector is introduced is derived. In general, codon optimization refers to replacing at least one codon in the original base sequence by a codon that is more frequently used in the organism species of a subject, while maintaining the original amino acid sequence. A codon usage frequency table is easily available in, for example, "Codon Usage Database" (found on the world wide web at kazusa.or.jp/codon/) provided by the Kazusa DNA Research Institute, and it is possible to optimize codons using these tables. Computer algorithms for codon-optimizing specific sequences for expression in specific animal species are also available in, for example, Gene Forge (Aptagen, LLC, Jacobus, PA), and the like.

The expression vector for a guide RNA and the expression vector for a Cas protein may be the same expression vectors. That is, in the production method of the present embodiment, it is possible to use an expression vector containing a guide RNA coding sequence and a Cas protein coding sequence, each of which are in an expressible state. In this expression vector, it is preferable that each of the guide RNA coding sequence and the Cas protein coding sequence be functionally linked to different promoters.

<Introduction Step>

The production method of the present embodiment includes a step of introducing, into a cell, (A) the guide RNA of (a1), (a2), or (a12) described above, or the expression vector therefor, and (B) the Cas protein or the expression vector therefor.

The cell into which (A) and (B) described above are introduced is not particularly limited, and it is possible to use a desired cell that is a genome editing subject. An organism from which the cell is derived is not particularly limited, and examples thereof include animals such as mammals such as humans, monkeys, mice, rats, dogs, cats, rabbits, cows, horses, pigs, goats, and sheep; birds such as chickens; reptiles such as snakes and lizards; amphibians such as African clawed frog; fishes such as zebrafish, killifish, and Takifugu *rubripes*; chordates such as sea squirts; and arthropods such as *Drosophila* and silkworm; plants such as *Arabidopsis thaliana*, rice, wheat, and *Nicotiana tabacum*; fungi such as yeast and *Neurospora crassa*; bacteria such as *Escherichia coli, Bacillus subtilis*, and Cyanophyceae; and the like.

The type of cell is not particularly limited, and examples thereof include cells derived from various tissues or of various properties, such as blood cells, hematopoietic stem cells/precursor cells, gametes (sperm, ovum), fertilized eggs, fibroblasts, epithelial cells, vascular endothelial cells, nerve cells, hepatocytes, keratinocytes, muscle cells, epidermal cells, endocrine cells, tissue stem cells, iPS cells, ES cells, and cancer cells. Examples thereof further include cells having various genetic diseases such as sickle cell disease, Huntington's chorea, Duchenne muscular dystrophy, and fibrodysplasia ossificans progressiva (FOP).

A method for introducing (A) and (B) described above is not particularly limited, and can be appropriately selected according to subject cells and the type of material (whether it is nucleic acid, protein, and the like).

Examples of methods for introducing an expression vector into cells include a lipofection method, a microinjection method, a DEAE-dextran method, a gene gun method, an electroporation method, a calcium phosphate method, and the like. In a case where an expression vector is a virus vector, examples of methods for infecting cells with a virus vector include a polybrene method.

A method for introducing RNA into cells is not particularly limited, and a known method can be appropriately selected and used. For example, for RNA, it is possible to use a commercially available RNA transfection reagent such as Lipofectamine (registered trademark) MessengerMAX (manufactured by Life Technologies Corporation).

A method for introducing protein into cells is not particularly limited, and a known method can be appropriately selected and used. Examples of such methods include a method using protein transduction reagent, a method using protein transduction domain (PTD) fusion proteins, a microinjection method, and the like.

(A) and (B) described above may be introduced into cells at the same time, may be introduced sequentially, or may be introduced separately with a certain time interval. In a preferred embodiment, (A) and (B) described above are introduced into cells at the same time.

<Arbitrary Step>

The production method of the present embodiment may include an arbitrary step in addition to the above-described introduction step. Examples of arbitrary steps include a step of introducing (C) a donor vector into cells.

<<(C) Donor Vector>>

The donor vector contains a base sequence adjacent to a target region as a homology arm. The donor vector can contain a desired base sequence (hereinafter, may be referred to as a "knock-in sequence") between the 5'-arm and the 3'-arm. The knock-in sequence is not particularly limited and can be an arbitrary sequence. The knock-in sequence may be, for example, a sequence for gene knock-out, may be a sequence for base substitution, or may be an arbitrary gene sequence. In a case where the knock-in sequence is an arbitrary gene sequence, it is preferable to set a target sequence within a safe harbor region.

The donor vector may be a circular DNA vector (for example, a plasmid vector) or may be a linear DNA vector. The donor vector may contain other sequences in addition to the homology arms and the knock-in sequence. Examples of other sequences include a marker gene, a replication origin, a gene encoding a protein that is bonded to a replication origin to control replication, and the like. Examples of marker genes include the same examples described above.

A method for introducing a donor vector is not particularly limited, and can be appropriately selected according to subject cells. Examples of methods for introducing a donor vector into cells include a lipofection method, a microinjection method, a DEAE-dextran method, a gene gun method, an electroporation method, a calcium phosphate method, and the like.

The donor vector may be introduced into cells at the same as (A) and (B) described above, may be introduced sequentially, or may be introduced with a certain time interval after introduction of (A) and (B). In a preferred embodiment, the donor vector is introduced into cells at the same time as (A) and (B) described above.

<<Culture Step>>

The arbitrary step may be a step of introducing (A) and (B) described above, and as necessary, (C) described above into cells, and thereafter culturing the cells. It is sufficient for culture of the cells to be performed under appropriate culture conditions according to the type of cell. In a case where (A), (B), and/or (C) described above are vectors containing a drug-resistant marker, the culture may be performed in the presence of the drug. By performing the culture in the presence of the drug, it is possible to efficiently select cells that have been genome-edited. Furthermore, cells may be cloned by diluting or plating a cell culture solution, and the like.

<<Step of Analyzing Genome Editing Pattern>>

The arbitrary step may be a step of introducing (A) and (B) described above, and as necessary, (C) described above into cells, and thereafter analyzing a genome editing pattern.

An analysis method for a genome editing pattern is not particularly limited, and examples thereof include a method in which after the above-described introduction step, for example, a culture step is performed as appropriate, thereafter, a cell culture solution is plated, DNA is extracted from generated colonies, and analysis on sequence of target regions is performed.

By performing analysis on sequences of target regions of both alleles, it is possible to confirm whether or not the cell is a cell in which only one allele is genome-edited.

In the production method of the present embodiment, it is possible to increase a proportion of cells in which only one allele is genome-edited when performing genome editing by using, as a guide RNA, (a1) a guide RNA in which one or more nucleotide residues are added to a 5'-end of a spacer sequence, or (a2) a guide RNA containing a spacer sequence having single-base or multiple-base mismatches with respect to a target sequence. Therefore, according to the production method of the present embodiment, it is possible to efficiently produce cells in which only one allele is genome-edited. Furthermore, according to the production method of the present embodiment, it is possible to inhibit cytotoxicity caused by introduction of sgRNA, Cas9, and the like.

In another embodiment, the present invention provides a method for genome-editing only one allele, the method including: a step of introducing, into a cell, (A) at least one selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector for the guide RNA of (a1) or (a2), and (B) at least one selected from the group consisting of a Cas protein and an expression vector for the Cas protein.

[Guide RNA, Vector, and Kit]

In one embodiment, the present invention provides a guide RNA in which one or more nucleotide residues are added to a 5'-end of a spacer sequence.

The guide RNA of the present embodiment is the same as the guide RNA of (a1) described in the section of < (A) Guide RNA> in [Production method for cell in which only one allele is genome-edited] described above.

In the guide RNA of the present embodiment, the spacer sequence is preferably a sequence having single-base or multiple-base mismatches with respect to a target sequence. That is, the guide RNA of the present embodiment is preferably the guide RNA of (a12) described above.

In one embodiment, the present invention provides an expression vector for a guide RNA in which one or more nucleotide residues are added to a 5'-end of a spacer sequence.

The expression vector of the present embodiment is the same as the expression vector for a guide RNA of (a1) or (a12) described in the section of <(A) Guide RNA> in [Production Method for Cell in which Only One Allele is Genome-Edited] Described Above.

The expression vector of the present embodiment may further contain a Cas protein coding sequence (preferably a Cas9 protein coding sequence) in an expressible state.

In one embodiment, the present invention provides a production kit for a cell in which only one allele is genome-edited, the production kit including: (A) at least one selected from the group consisting of (a1) a guide RNA in which one or more nucleotide residues are added to a 5'-end of a spacer sequence, (a2) a guide RNA containing a spacer sequence having single-base or multiple-base mismatches with respect to a target sequence, and (a3) an expression vector for the guide RNA of (a1) or (a2). The production kit further preferably contains (B) at least one selected from the group consisting of a Cas protein and an expression vector therefor.

The guide RNAs of (a1) and (a2) are the same as the guide RNAs of (a1) and (a2) described in the section of <(A) Guide RNA> in [Production method for cell in which only one allele is genome-edited] described above. The guide RNA may be the guide RNA of (a12) described above.

The expression vector of (a3) is the same as the expression vector of (a3) for a guide RNA described in the section of < (A) Guide RNA> in [Production method for cell in which only one allele is genome-edited] described above.

The Cas protein and the expression vector therefor of (B) are the same as those described in the section of < (B) Cas protein> in [Production method for cell in which only one allele is genome-edited] described above.

In a case where (A) and (B) are expression vectors, a guide RNA coding sequence and a Cas protein coding sequence may be contained in the same expression vector, each of which are in an expressible state.

The kit of the present embodiment may have other constitutions in addition to (A) and (B) described above. The other constitutions are not particularly limited, and examples thereof include instructions for producing cells in which only one allele is genome-edited, reagents used for introducing an expression vector into cells, and the like.

[Prediction Method for Genome Editing Pattern]

In one embodiment, the present invention provides a prediction method for a genome editing pattern, the method including: a step (i) of introducing a guide RNA or an expression vector for the guide RNA, and a Cas protein or an expression vector for the Cas protein into a cell to perform genome editing; a step (ii) of extracting DNA from the genome-edited cell; a step (iii) of amplifying a DNA fragment containing a target region from the DNA; a step (iv) of performing sequence analysis on the amplified DNA fragment to obtain an indel induction ratio (P) of the target region; and a step (v) of obtaining a monoallelic indel induction ratio (mono) and a biallelic indel induction ratio (bi) from Formulas (m) or (m1) and (b) or (b1).

$$\text{mono}=2\times P\times(1-P) \qquad (m)$$

$$bi=P^2 \qquad (b)$$

$$\text{mono}=-1.303P^2+1.2761P+0.0274 \qquad (m1)$$

$$bi=0.6515P^2+0.3619P-0.0137 \qquad (b1)$$

<Step (i)>

The step (i) is a step of introducing a guide RNA or an expression vector therefor, and a Cas protein or an expression vector therefor into a cell to perform genome editing.

The guide RNA is not particularly limited, and it is sufficient to use a guide RNA that can be used in the CRISPR/Cas system. A spacer sequence is not particularly limited and may be any spacer sequence as long as it has an arbitrary target sequence as a target sequence.

The expression vector for the guide RNA can be produced in the same manner as in the expression vector described in the section of < (A) Guide RNA> in [Production method for cell in which only one allele is genome-edited] described above.

The Cas protein is not particularly limited, and it is sufficient to use a Cas protein that can be used in the CRISPR/Cas system. The Cas protein is preferably a Cas9 protein, and is more preferably a Cas9 protein of *S. pyogenes*.

The expression vector for the Cas protein can be produced in the same manner as in the expression vector described in the section of < (B) Cas protein> in [Production method for cell in which only one allele is genome-edited] described above.

Introduction of the guide RNA and the Cas protein or the expression vectors therefor into cells can be performed in the same manner as in the method described in the section of <Introduction step> in [Production method for cell in which only one allele is genome-edited].

After introduction into the cells, culturing may be performed as appropriate. In a case where the expression vectors for the guide RNA and the Cas protein are introduced into the cells, and these expression vectors have a drug-resistant marker, the cells may be cultured in the presence of the drug to select cells into which the expression vectors have been introduced.

<Step (ii)>

The step (ii) is a step of extracting DNA from the cell genome-edited in the step (i).

A DNA extraction method is not particularly limited, and it is sufficient to use a known DNA extraction method. Examples of DNA extraction methods include a phenol/chloroform extraction method, a method of heating under alkaline conditions (for example, 99° C. for 10 minutes in the presence of 50 mM NaOH), and the like. Furthermore, it is also possible to use a commercially available DNA extraction kit and the like.

<Step (iii)>

The step (iii) is a step of amplifying a DNA fragment containing a target region from the DNA extracted in the step (ii).

A method for amplifying the target region is not particularly limited, and it is sufficient to use a known method for amplifying a nucleic acid fragment. Examples of methods for amplifying a nucleic acid fragment include a PCR method, an isothermal amplification method, and the like. For example, it is possible to amplify a DNA fragment of a target region by designing a primer that enables amplification of the target region and using a PCR method, an isothermal amplification method, or the like.

A length of the amplified DNA fragment is not particularly limited as long as it contains the target region, and it can be, for example, about 20 to 1,000 bp, generally about 350 to 750 bp.

The amplified DNA fragment may be cloned using a commercially available cloning vector or the like. Furthermore, a cloning vector into which the amplified DNA fragment has been inserted may be introduced into *Escherichia coli* or the like, and the *Escherichia coli* may be cultured to form a colony. DNA may be extracted from the colony thus obtained and provided to sequence analysis in the step (iv). The number of colonies to be subjected to sequence analysis is not particularly limited, and it may be, for example, about 10 to 200, about 20 to 100, about 20 to 50, and the like.

<Step (iv)>

The step (iv) is a step of performing sequence analysis on the DNA fragment amplified in the step (iii) to obtain an indel induction ratio (P) of the target region.

A method for sequence analysis of the DNA fragment is not particularly limited, and it is sufficient to use a known sequence analysis method. It is possible to use a commercially available sequencer for the sequence analysis, and it is possible to perform DNA sequencing according to a method recommended by the manufacturer. Furthermore, analysis of the presence or absence of an indel in the amplified DNA fragment may be performed by T7E1 assay, or the sequence analysis by the sequencer and the T7E1 assay may be used in combination.

The indel induction ratio (P) of the target region can be calculated by Formula (p) based on results of the sequence analysis.

$$P = \frac{\text{Number of DNA fragments having indel}}{\substack{\text{Number of DNA fragments having indel} + \\ \text{Number of DNA fragments not having indel}}} \tag{p}$$

<Step (v)>

The step (v) is a step of obtaining a monoallelic indel induction ratio (mono) and a biallelic indel induction ratio (bi) from Formulas (m) and (b).

$$\text{mono} = 2 \times P \times (1 - P) \tag{m}$$

$$bi = P^2 \tag{b}$$

Formulas (m1) and (b1) may be used in place of Formulas (m) and (b) described above.

$$\text{mono} = -1.303P^2 + 1.2761P + 0.0274 \tag{m1}$$

$$bi = 0.6515P^2 + 0.3619P - 0.0137 \tag{b1}$$

By substituting a value of the indel induction ratio (P) obtained in the step (iv) into Formulas (m) or (m1) and (b) or (b1) described above, it is possible to obtain each of a monoallelic indel induction ratio (mono) and a biallelic indel induction ratio (bi). As shown in Examples to be described later, each value of the indel induction ratio (mono) and the indel induction ratio (bi) obtained by the method of the present embodiment approximates to indel induction ratios confirmed by an actual test.

According to the prediction method of the present embodiment, it is possible to predict a monoallelic indel induction ratio and a biallelic indel induction ratio by a simple operation. Therefore, by carrying out the prediction method of the present embodiment using an arbitrary guide RNA, it is possible to predict a genome editing pattern by genome editing using this guide RNA.

[AIMS Cell]

In one embodiment, the present invention provides a cell including: a chimeric gene in which a localized protein coding sequence, a cleavage site coding sequence, and a first fluorescent protein coding sequence are linked in-frame in this order at one allele; and a chimeric gene in which the localized protein coding sequence, the cleavage site coding sequence, and a second fluorescent protein coding sequence are linked in-frame in this order at the other allele. In the present specification, the terms "first" and "second" are descriptions used for the sake of convenience.

The cell of the present embodiment is a cell (AIMS cell) that can be used for analysis of a genome editing pattern by an AIMS to be described later. By using the cell of the present embodiment, it is possible to easily investigate whether genome editing is induced in both alleles or genome editing is induced only in one allele.

<Localized Protein Coding Sequence>

A localized protein can be appropriately selected according to a cell that is a genome editing subject. As long as the localized protein is a protein localized within a cell, it may be a natural protein or may be an artificial protein (for example, a mutant-type protein or cleavage-type protein of natural localized proteins, peptides containing localization signals, and the like). In a case where the localized protein is a natural protein, the natural protein may be an endogenous protein of a subject cell or may be an exogenous protein (localized protein derived from another organism). It is preferable that the localized protein be an endogenous protein of a subject cell and be a protein that is always expressed. The localized protein may be a nucleus-localized protein or may be a cell membrane-localized protein.

In a case of human cells, examples of nucleus-localized proteins include various transcription factors, various transcription regulating factors, and the like. Specific examples thereof include a TBX family such as TBX3 protein, a SOX family such as SOX2 protein, and the like. Furthermore, examples of cell membrane-localized proteins include various cell membrane receptors, various cell membrane antigens, and the like. Specific examples thereof include a cadherin family such as E-cadherin, an SSEA family such as SSEA4, and the like.

The localized protein coding sequence is not particularly limited as long as it has a base sequence encoding the localized protein, and may include a silent mutation. The localized protein coding sequence may be a sequence in which an intrinsic gene sequence of an endogenous localized protein is utilized, or may be exogenous DNA. In a case where the localized protein coding sequence is exogenous DNA (for example, exogenous natural localized protein coding sequence, artificial localized protein coding sequence, and the like), the localized protein coding sequence may be a sequence functionally linked to a promoter constitutively expressed in a subject cell.

<Cleavage Site>

A cleavage site is not particularly limited. Examples thereof include a self-cleavage site and an endopeptidase cleavage site, and specific examples thereof include a 2A peptide coding sequence.

A 2A peptide is not particularly limited, and a known 2A peptide or 2A-like peptide can be used. For example, it is possible to use a 2A peptide selected from the group consisting of P2A peptide, F2A peptide, E2A peptide, and T2A peptide.

In a case where the cleavage site encodes a self-cleavage sequence such as ribosomal skipping or an amino acid sequence such as a peptidase recognition sequence, it may contain a silent mutation. For example, a 2A peptide coding sequence is not particularly limited as long as it has a base sequence encoding a 2A peptide, and may include a silent mutation. Furthermore, the 2A peptide coding sequence may be codon-optimized according to subject cells. As specific examples of the 2A peptide coding sequence, a P2A peptide coding sequence is set forth in SEQ ID NO: 14, and a coding sequence (aP2A) containing a silent mutation in the P2A peptide coding sequence is set forth in SEQ ID NO: 15.

<First Fluorescent Protein Coding Sequence>

A first fluorescent protein is not particularly limited, and a known fluorescent protein can be used. Examples of fluorescent proteins include, but are not limited to, Sirius, BFP, EBFP, ECFP, mTurquoise, TagCFP, AmCyan, mTFP1, MidoriishiCyan, CFP, TurboGFP, AcGFP, TagGFP, Azami-Green, ZsGreen, EmGFP, GFP, EGFP, GFP2, HyPer, Tag YFP, EYFP, Venus, YFP, PhiYFP, PhiYFP-m, TurboYFP, ZsYellow, mBanana, KusabiraOrange, mOrange, TurboRFP, tdTomato, DsRed, DsRed-Express, DsRed2, TagRFP, DsRed-Monomer, AsRed, AsRed2, mStrawberry, TurboFP602, RFP, ERFP, mRFP1, JRed, KillerRed, mCherry, HcRed, KeimaRed, TurboFP650, mRasberry, mPlum, PS-CFP, Dendra2, Kaede, EosFP, KikumeGR, and the like.

The first fluorescent protein coding sequence is not particularly limited as long as it has a base sequence encoding a fluorescent protein, and may include a silent mutation. Furthermore, the first fluorescent protein coding sequence may be codon-optimized according to subject cells. As specific examples of the fluorescent protein coding sequence, a tdTomato coding sequence is set forth in SEQ ID NO: 16, and a Venus coding sequence is set forth in SEQ ID NO: 17.

<Second Fluorescent Protein Coding Sequence>

A second fluorescent protein is a fluorescent protein different from the first fluorescent protein. The second fluorescent protein is not particularly limited as long as it is different from the first fluorescent protein, and a known fluorescent protein can be used. Examples of fluorescent proteins include the same proteins as the exemplary examples for the first fluorescent protein described above. The second fluorescent protein preferably has a different fluorescence wavelength from that of the first fluorescent protein.

The second fluorescent protein coding sequence is not particularly limited as long as it has a base sequence encoding a fluorescent protein, and may include a silent mutation. Furthermore, the first fluorescent protein coding sequence may be codon-optimized according to subject cells.

<Chimeric Gene>

The cell of the present embodiment includes the chimeric gene (hereinafter, may be referred to as a "first chimeric gene") in which the localized protein coding sequence, the cleavage site (for example, a 2A peptide coding sequence), and the first fluorescent protein coding sequence are linked in-frame in this order at one allele (hereinafter, may be referred to as a "first allele"). The cell of the present embodiment includes the chimeric gene (hereinafter, may be referred to as a "second chimeric gene") in which the localized protein coding sequence, the cleavage site (for example, a 2A peptide coding sequence), and the second fluorescent protein coding sequence are linked in-frame in this order at the other allele (hereinafter, may be referred to as a "second allele").

The cleavage sites (for example, a 2A peptide coding sequence) of the first chimeric gene and the second chimeric gene are the same. The localized protein coding sequences contained in the first chimeric gene and the second chimeric gene are preferably the same.

In a preferred embodiment, each of the first chimeric gene and the second chimeric gene is located at a locus of an intrinsic localized protein gene of the cell. Alternatively, each of the first chimeric gene and the second chimeric gene may be located at the same locus within a safe harbor region.

The first chimeric gene and the second chimeric gene are respectively present at the first allele and the second allele in the cell, each of which are in an expressible state.

<Production Method for AIMS Cell>

It is possible to produce the AIMS cell containing the first chimeric gene and the second chimeric gene using a technique such as genome editing. Specific examples of production methods for the AIMS cell will be described below, but are not limited thereto.

First, donor vectors (knock-in vectors) each containing the first chimeric gene and the second chimeric gene are produced as vectors for knocking in the first chimeric gene and the second chimeric gene into the genome of a subject cell. The knock-in vectors can be produced by a known method. A homology arm can be appropriately designed according to locations on the genome into which the chimeric genes is inserted. The homology arm is preferably a base sequence of an intrinsic localized protein gene and a region adjacent to the localized protein gene.

Next, a guide RNA, which has a sequence in a region in which the chimeric gene is knocked in as a target sequence, is designed. In a case where the homology arm of the knock-in vector is a base sequence of an intrinsic localized protein gene and a region adjacent to the localized protein gene, the target sequence is selected from, for example, the sequence in the intrinsic localized protein gene.

Next, the guide RNA or an expression vector therefor, a Cas protein or an expression vector therefor, and the knock-in vector of the first chimeric gene and the knock-in vector of the second chimeric gene are introduced into cells. In a case where an expression vector is used for the guide RNA and a Cas protein, an expression vector therefor may be the same expression vector.

Examples of introduction methods include the same methods as the methods described in the section of <Introduction step> in [Production method for cell in which only one allele is genome-edited] described above.

After introduction into the cells, culturing may be performed as appropriate. In a case where the expression vectors for the guide RNA and the Cas protein are introduced into the cells, and these expression vectors have a drug-resistant marker, the cells may be cultured in the presence of the drug to select cells into which the expression vectors have been introduced. Also in a case where each of the knock-in vectors of the first and second chimeric genes has a drug-resistant marker, the cells may be cultured in the presence of the drug to select cells into which the knock-in vectors have been introduced.

Next, the cells in which the fluorescence of both the first fluorescent protein and the second fluorescent protein is observed are collected. Sorting of fluorescent cells can be performed by a known method, and it can be performed using, for example, a flow cytometer, a fluorescence microscope, or the like.

For the acquired cells, it is possible to confirm, by PCR or the like, whether each of the first chimeric gene and the second chimeric gene has been inserted into each of target loci of the first allele and the second allele.

In the cell of the present embodiment, chimeric proteins expressed from the first chimeric gene and the second chimeric gene are cleaved at a cleavage site (for example, 2A peptide). Since the first fluorescent protein and the second fluorescent protein are each separated from localized proteins, they are distributed throughout the cell without being localized within the cell (refer to "wt" in FIG. 1A).

Meanwhile, as a result of performing genome editing with the cleavage site (for example, a 2A peptide coding sequence) as a target, a fluorescent protein is not generated when a frame-shift indel occurs at the cleavage site (for example, a 2A peptide coding sequence). Therefore, fluorescence of the fluorescent protein introduced into the allele in which the frame-shift indel occurs disappears (refer to "frame-shift" in FIG. 1A).

On the other hand, as a result of performing genome editing with the cleavage site (for example, a 2A peptide) as a target, cleavage at the 2A peptide does not occur when an in-frame indel occurs at the cleavage site (for example, a 2A peptide coding sequence). Therefore, the fluorescent protein introduced into the allele in which the frame-shift indel occurs is localized according to the localized protein without being separated from the localized protein (refer to "in-frame" in FIG. 1A).

A subject cell used for producing the AIMS cell is not particularly limited, and a desired cell can be used. An organism from which the cell is derived is not particularly limited, and examples thereof include animals such as mammals such as humans, monkeys, mice, rats, dogs, cats, rabbits, cows, horses, pigs, goats, and sheep; birds such as chickens; reptiles such as snakes and lizards; amphibians such as African clawed frog; fishes such as zebrafish, killifish, and Takifugu *rubripes*; chordates such as sea squirts; and arthropods such as *Drosophila* and silkworm; plants such as *Arabidopsis thaliana*, rice, wheat, and *Nicotiana tabacum*; fungi such as yeast and *Neurospora crassa*; bacteria such as *Escherichia coli, Bacillus subtilis*, and Cyanophyceae; and the like.

The type of subject cell is not particularly limited, and examples thereof include cells derived from various tissues or of various properties, such as blood cells, hematopoietic stem cells/precursor cells, gametes (sperm, ovum), fertilized eggs, fibroblasts, epithelial cells, vascular endothelial cells, nerve cells, hepatocytes, keratinocytes, muscle cells, epidermal cells, endocrine cells, tissue stem cells, iPS cells, ES cells, and cancer cells. Examples thereof further include cells having various genetic diseases such as sickle cell disease, Huntington's chorea, and Duchenne muscular dystrophy.

The subject cell may be a primary cultured cell or may be a cell line subjected to immortalization treatment. Examples of cell lines include Hela cells derived from humans, COS7 cells derived from African green monkeys, 3T3 cells derived from mice, CHO cells derived from hamsters, PC12 cells derived from rats, and the like.

In an analysis method for a genome editing pattern described below, a genome editing pattern is analyzed by utilizing the above-described characteristics of the cell of the present embodiment.

[Analysis Method for Genome Editing Pattern]

In one embodiment, the present invention provides an analysis method for a genome editing pattern, the method including: a step (I) of introducing a guide RNA targeting the cleavage site (for example, a 2A peptide coding sequence) or an expression vector therefor, and a Cas protein or an expression vector therefor into the cell (AIMS cell) of the above-described embodiment to perform genome editing; a step (II) of analyzing a fluorescence pattern of the cell after the step (I); and a step (III) of determining a genome editing pattern based on the fluorescence pattern analyzed in the step (II).

The analysis method for a genome editing pattern of the present embodiment is characterized by using the above-described AIMS cell. By using the above-described AIMS cell, it is possible to analyze a genome editing pattern by a simple method.

<Step (I)>

The step (I) is a step of introducing a guide RNA targeting a cleavage site (for example, a 2A peptide coding sequence) or an expression vector therefor, and a Cas protein or an expression vector therefor into the AIMS cell to perform genome editing.

The guide RNA targeting a cleavage site (for example, a 2A peptide coding sequence) can be appropriately designed according to a base sequence of a cleavage site (for example, a 2A peptide coding sequence) contained in the AIMS cell used. For example, in a case where a 2A peptide used as the cleavage site is a P2A peptide, a sequence set forth in SEQ ID NO: 14 is an exemplary example as a target sequence.

Examples of introduction methods for a guide RNA or an expression vector therefor and a Cas protein or an expression vector therefor include the same methods as the methods described in the section of <Introduction step> in [Production method for cell in which only one allele is genome-edited] described above. In a case where an expression vector is used for the guide RNA and a Cas protein, an expression vector therefor may be the same expression vector.

After introduction into the cells, culturing may be performed as appropriate. In a case where the expression vectors for the guide RNA and the Cas protein are introduced into the cells, and these expression vectors have a drug-resistant marker, the cells may be cultured in the presence of the drug to select cells into which the expression vectors have been introduced. Furthermore, cells may be cloned by diluting or plating a cell culture solution, and the like.

<Step (II)>

The step (II) is a step of analyzing a fluorescence pattern of the AIMS cell after the step (I).

It is possible to perform analysis of a fluorescence pattern of the AIMS cell after the genome editing by a known method. Examples of analysis methods for a fluorescence pattern include observation with a fluorescence microscope, a method using a flow cytometer, and the like. For example, observation with a fluorescence microscope is preferable from the viewpoint of accurately analyzing a fluorescence pattern. However, the analysis method is not particularly limited as long as a fluorescence pattern can be analyzed.

Table 1 shows fluorescence patterns that can be detected by the present step.

TABLE 1

| Fluorescence pattern | Fluorescence of first fluorescent protein | Fluorescence of second fluorescent protein |
|---|---|---|
| (1) | Distributed throughout cell | Distributed throughout cell |
| (2) | Distributed throughout cell | Localized |
| (3) | Distributed throughout cell | Disappeared |
| (4) | Localized | Distributed throughout cell |
| (5) | Localized | Localized |
| (6) | Localized | Disappeared |
| (7) | Disappeared | Distributed throughout cell |
| (8) | Disappeared | Localized |
| (9) | Disappeared | Disappeared |

<Step (III)>

The step (III) is a step of determining a genome editing pattern based on the fluorescence pattern analyzed in the step (II).

Based on the fluorescence pattern analyzed in the step (II), a genome editing pattern can be determined as shown in Table 2.

TABLE 2

| Fluorescence pattern | First allele | Second allele | Genome-edited allele |
|---|---|---|---|
| (1) | No indel | No indel | None |
| (2) | No indel | In-frame indel | Second allele |
| (3) | No indel | Frame-shift indel | Second allele |
| (4) | In-frame indel | No indel | First allele |
| (5) | In-frame indel | In-frame indel | First allele and second allele |
| (6) | In-frame indel | Frame-shift indel | First allele and second allele |
| (7) | Frame-shift indel | No indel | First allele |
| (8) | Frame-shift indel | In-frame indel | First allele and second allele |
| (9) | Frame-shift indel | Frame-shift indel | First allele and second allele |

As described above, for fluorescence patterns (2) and (3), it is determined that only the second allele has been genome-edited. For fluorescence patterns (4) and (7), it is determined that only the first allele has been genome-edited. For fluorescence (5), (6), (8), and (9), it is determined that both the first allele and the second allele have been genome-edited. In a fluorescence pattern (1), it is determined that none of the alleles have been genome-edited.

According to the method of the present embodiment, a genome editing pattern can be analyzed by a simple method. Furthermore, it is possible to obtain a proportion of genome editing in both alleles and a proportion of genome editing in only one allele by aggregating genome editing patterns analyzed for individual cells. Therefore, for example, it is possible to analyze whether a newly designed guide RNA is likely to induce genome editing in both alleles or induce genome editing in only one allele, and the like. Accordingly, the method of the present embodiment is useful for developing a new guide RNA for inducing a desired genome editing pattern.

[Treatment, Alleviation, and/or Prevention of Genetic Diseases by Genome Editing of One Allele]

In one embodiment, the present invention provides treatment, alleviation, and/or prevention of genetic diseases by genome editing of one allele which is achieved by the above-described embodiment of the present invention. That is, homozygous mutations or heterozygous mutations (including compound heterozygous mutations) which cause genetic diseases are repaired by genome editing of one allele which is achieved by the above-described embodiment of the present invention, and thereby treatment, alleviation, and/or prevention of the diseases is possible. In a case where a subject has a disease gene and a normal gene heterozygously, by genome-editing only the disease gene by the genome editing method for only one allele according to the above-described embodiment of the present invention, treatment, alleviation, and/or prevention of the genetic disease is possible. In a case where a subject has a disease gene homozygously, by genome-editing one allele by the genome editing method for only one allele according to the embodiment of the present invention, the homozygous disease gene is made heterozygous between the disease gene and a normal gene, as a result, normal proteins are expressed from the repair allele, and thereby treatment, alleviation, and/or prevention of the genetic disease is possible. As will be described later, the genome editing of one allele, which is achieved by the above-described embodiment of the present invention, is highly therapeutically safe because it can inhibit an off-target effect while maintaining on-target genome editing activity. A genetic disease that can be treated, alleviated, and/or prevented by the genome editing of one allele according to the above-described embodiment of the present invention is not particularly limited as long as it is a disease caused by a gene mutation. Examples thereof include, but are not limited to, sickle cell disease, Huntington's chorea, Duchenne muscular dystrophy, fibrodysplasia ossificans progressiva (FOP), and the like. Since the genome editing method for one allele of the above-described embodiment inhibits cytotoxicity caused by the genome editing, it is possible to suitably treat genetic diseases. In particular, in genome editing using the guide RNA of (a1) described below in which one or more nucleotide residues are added to the 5'-end of a spacer sequence with respect to a target sequence in a disease gene, or an expression vector for this guide RNA, it is possible to inhibit cytotoxicity caused by the genome editing.

The present invention provides, for example, a method for treating, alleviating, and/or preventing a genetic disease, the method including a step of administering, to a subject, (A) at least one selected from the group consisting of (a1) a guide RNA in which one or more nucleotide residues are added to a 5'-end of a spacer sequence with respect to a target sequence in a disease gene, (a2) a guide RNA containing a spacer sequence having single-base or multiple-base mismatches with respect to the target sequence, and (a3) an expression vector for the guide RNA of (a1) or (a2), and (B) at least one selected from the group consisting of a Cas protein and an expression vector therefor.

The disease may be a disease caused by heterozygous mutations (including compound heterozygous mutations) or may be a disease caused by homozygous mutations. A method for administering (A) and (B) is not particularly limited as long as it is a method in which genome editing of one allele can be caused, and may be oral administration or may be parenteral administration. Examples of forms of parenteral administration include intravenous injection, intravenous drip infusion, subcutaneous injection, intradermal injection, intraperitoneal injection, and the like. (A) and (B) may be administered at the same time or may be administered separately. Dosages of (A) and (B) differ depending on degrees of diseases, ages, sexes, body weights, and sensitivity differences of a subject, administration methods, administration times, administration intervals, administration periods, properties of preparations, types of active ingredient, and the like, but those skilled in the art can appropriately set them.

The present invention provides, for example, a pharmaceutical composition for treating, alleviating, and/or preventing a genetic disease, the pharmaceutical composition including:

(A) at least one selected from the group consisting of (a1) a guide RNA in which one or more nucleotide residues are added to a 5'-end of a spacer sequence with respect to a target sequence in a disease gene, (a2) a guide RNA containing a spacer sequence having single-base or multiple-base mismatches with respect to the target sequence, and (a3) an expression vector for the guide RNA of (a1) or (a2).

The pharmaceutical composition may further include:

(B) at least one selected from the group consisting of a Cas protein and an expression vector therefor.

Alternatively, the pharmaceutical composition may be used in combination with another pharmaceutical composition including:

(B) at least one selected from the group consisting of a Cas protein and an expression vector therefor.

In this case, the other pharmaceutical composition may be administered at the same time as the pharmaceutical composition of the present invention, or may be administered separately.

The pharmaceutical composition of the present invention may be formulated by blending in a pharmaceutically acceptable carrier and the like. Examples of pharmaceutically acceptable carriers include excipients, binders, disintegrating agents, lubricants, colorants, flavoring agents, stabilizing agents, emulsifiers, absorption accelerating agents, surfactants, pH adjusting agents, preservatives, antioxidants, and the like.

The disease may be a disease caused by heterozygous mutations (including compound heterozygous mutations) or may be a disease caused by homozygous mutations. An administration form of the pharmaceutical composition of the present invention is not particularly limited, and can be administered orally or parenterally. Examples of forms of parenteral administration include intravenous injection, intravenous drip infusion, subcutaneous injection, intradermal injection, intraperitoneal injection, and the like. A dosage of the pharmaceutical composition of the present invention differs depending on degrees of diseases, ages, sexes, body weights, and sensitivity differences of a subject, administration methods, administration times, administration intervals, administration periods, properties of preparations, types of active ingredient, and the like, but those skilled in the art can appropriately set them.

The present invention provides, for example, the following (A) and (B) for use in treatment, alleviation, and/or prevention of genetic diseases, (A) at least one selected from the group consisting of (a1) a guide RNA in which one or more nucleotide residues are added to a 5'-end of a spacer sequence with respect to a target sequence in a disease gene, (a2) a guide RNA containing a spacer sequence having single-base or multiple-base mismatches with respect to the target sequence, and (a3) an expression vector for the guide RNA of (a1) or (a2), and (B) at least one selected from the group consisting of a Cas protein and an expression vector therefor.

The disease may be a disease caused by heterozygous mutations (including compound heterozygous mutations) or may be a disease caused by homozygous mutations.

The present invention provides, for example, use of the following (A) and (B) in manufacturing of a therapeutic agent, an alleviating agent, and/or a prophylactic agent for genetic diseases, (A) at least one selected from the group consisting of (a1) a guide RNA in which one or more nucleotide residues are added to a 5'-end of a spacer sequence with respect to a target sequence in a disease gene, (a2) a guide RNA containing a spacer sequence having single-base or multiple-base mismatches with respect to the target sequence, and (a3) an expression vector for the guide RNA of (a1) or (a2), and (B) at least one selected from the group consisting of a Cas protein and an expression vector therefor.

The disease may be a disease caused by heterozygous mutations (including compound heterozygous mutations) or may be a disease caused by homozygous mutations.

In [Treatment, alleviation, and/or prevention of genetic diseases by genome editing of one allele] described above, cells, which are derived from a subject in which a disease gene has been repaired by introducing (A) and (B), may be used instead of using (A) and (B). That is, by introducing (A) and (B) described above into cells acquired from the subject, homozygous mutations or heterozygous mutations (including compound heterozygous mutations) which cause genetic diseases in cells can be repaired by the genome editing of one allele which is achieved by the above-described embodiment of the present invention. By returning cells in which this disease gene has been repaired (hereinafter referred to as "repaired cells") into the subject, normal proteins are expressed from the repaired cells, and thereby a genetic disease can be treated, alleviated, and/or prevented.

[Model Cell of Genetic Diseases]

In one embodiment, the present invention provides a method for producing a model cell of genetic diseases by the genome editing of one allele which is achieved by the above-described embodiment of the present invention, and a model cell produced by this method. That is, it is possible to produce a model cell of genetic diseases by introducing indels or desired mutations into one allele for a gene known to be a causative gene of a genetic disease or a gene suspected to be a causative gene of a genetic disease by the genome editing of one allele which is achieved by the above-described embodiment of the present invention with a normal gene of the above gene as a target. A cell that is a subject of the genome editing may have a normal gene in a homozygous form, or may have a normal gene and a disease gene in a heterozygous form. A genetic disease contained in the model cell of genetic diseases of the present embodiment is not particularly limited as long as it is a disease caused by a gene mutation. Examples thereof include, but are not limited to, cancer, sickle cell disease, Huntington's chorea, Duchenne muscular dystrophy, fibrodysplasia ossificans progressiva (FOP), and the like.

The present invention provides, for example, a method for producing a model cell of genetic diseases, the method including a step of administering (introducing), into the cell in vitro, (A) at least one selected from the group consisting of (a1) a guide RNA in which one or more nucleotide residues are added to a 5'-end of a spacer sequence with respect to a target sequence in a normal gene of a causative gene of a genetic disease or a gene suspected to be the causative gene, (a2) a guide RNA containing a spacer sequence having single-base or multiple-base mismatches with respect to the target sequence, and (a3) an expression vector for the guide RNA of (a1) or (a2), and (B) at least one selected from the group consisting of a Cas protein and an expression vector therefor.

The disease may be a disease caused by heterozygous mutations (including compound heterozygous mutations) or may be a disease caused by homozygous mutations.

The cell to which (A) and (B) are administered may be a primary cultured cell or may be a cell line subjected to immortalization treatment. Examples of cell lines include Hela cells derived from humans, COS7 cells derived from African green monkeys, 3T3 cells derived from mice, CHO cells derived from hamsters, PC12 cells derived from rats, and the like. The cell to which (A) and (B) are administered may be pluripotent stem cells, multipotent stem cells, monopoly stem cells, ES cells, or iPS cells. The cell to which (A) and (B) are administered is, for example, a cell of humans, mice, rats, guinea pigs, hamsters, rabbits, dogs, pigs, cows, horses, sheep, monkeys, or chickens. (A) and (B) may be administered at the same time or may be administered separately. A method for administering (method for introducing) (A) and (B) into the cell is not particularly limited, and a known method can be used. Examples thereof include the same methods as the methods described in the section of <Introduction step> in [Production method for cell in which only one allele is genome-edited] described above.

[Non-Human Animal Model of Genetic Diseases]

In one embodiment, the present invention provides a method for producing a non-human animal model of genetic diseases by the genome editing of one allele which is achieved by the above-described embodiment of the present invention, and a non-human animal model produced by this method. That is, it is possible to produce a non-human animal model of genetic diseases by introducing indels or desired mutations into one allele for a gene known to be a causative gene of a genetic disease or a gene suspected to be a causative gene of a genetic disease by the genome editing of one allele which is achieved by the above-described embodiment of the present invention with a normal gene of the above gene as a target. An animal that is a subject of the genome editing may have a normal gene in a homozygous form, or may have a normal gene and a disease gene in a heterozygous form. A genetic disease contained in the animal model of genetic diseases of the present embodiment is not particularly limited as long as it is a disease caused by a gene mutation. Examples thereof include, but are not limited to, sickle cell disease, Huntington's chorea, Duchenne muscular dystrophy, fibrodysplasia ossificans progressiva (FOP), and the like.

The present invention provides, for example, a method for producing a non-human animal model of genetic diseases, the method including a step of administering, to a non-human animal, (A) at least one selected from the group consisting of (a1) a guide RNA in which one or more nucleotide residues are added to a 5'-end of a spacer sequence with respect to a target sequence in a normal gene of a causative gene of a genetic disease or a gene suspected to be the causative gene, (a2) a guide RNA containing a spacer sequence having single-base or multiple-base mismatches with respect to the target sequence, and (a3) an expression vector for the guide RNA of (a1) or (a2), and (B) at least one selected from the group consisting of a Cas protein and an expression vector therefor.

Furthermore, in one embodiment, the present invention may be a method for producing a non-human animal model of genetic diseases, the method including a step of administering the above-described model cell of genetic diseases to a non-human animal. Furthermore, in one embodiment, the present invention may be a method for producing a non-human animal model of genetic diseases, the method including a step of injecting (A) and (B) described above or the above-described model cell of genetic diseases to a fertilized egg of a non-human animal.

The disease may be a disease caused by heterozygous mutations (including compound heterozygous mutations) or may be a disease caused by homozygous mutations.

As the non-human animal to which (A) and (B) are administered, it is possible use arbitrary laboratory animals which are available in the technical field, such as mice, rats, guinea pigs, hamsters, rabbits, dogs, pigs, cows, horses, sheep, monkeys, and chickens. A method for administering (A) and (B) is not particularly limited as long as it is a method in which genome editing of one allele can be caused, and may be oral administration or may be parenteral administration. Examples of forms of parenteral administration include intravenous injection, intravenous drip infusion, subcutaneous injection, intradermal injection, intraperitoneal injection, and the like. (A) and (B) may be administered at the same time or may be administered separately. Dosages of (A) and (B) differ depending on the types, ages in week/month, sexes, body weights, sensitivity differences of a non-human animal as an administration target, administration methods, administration times, administration intervals, administration periods, and the like, but those skilled in the art can appropriately set them.

EXAMPLES

Hereinafter, the present invention will be described with reference to examples, but the present invention is not limited to the following examples.

The meanings of main abbreviations and the like used in the following examples are shown below.

P2A-tdTomato allele: an allele in which a P2A-tdTomato chimeric gene has been knocked in.

P2A-Venus allele: an allele in which a P2A-Venus chimeric gene has been knocked in.

P2A-Neo allele: an allele in which a P2A-Neo chimeric gene has been knocked in.

All-in-one CRISPR plasmid: a plasmid that expresses Cas9, sgRNA, and a selectable marker.

p: RCP: an all-in-one CRISPR plasmid having a puromycin-resistant gene (Puro) as a selectable marker.

PX459: pSpCas9 (BB)-2A-Puro (PX459) V2.0 plasmid (Addgene, plasmid #62988).

P2A PX459: PX459 in which a spacer sequence targeting a P2A peptide coding sequence has been inserted at a BpiI site.

aP2A PX459: PX459 in which a spacer sequence targeting an aP2A sequence has been inserted at a BpiI site.

PX459 (del_Cas9-T2A-Puro): a plasmid from which a Cas9-T2A-Puro chimeric gene has been removed from PX459.

Cdh1-P2A-tdTomato KI vector: a knock-in vector for knocking in a P2A-tdTomato chimeric gene downstream of a Cdh1 gene.

Cdh1-P2A-Venus KI vector: a knock-in vector for knocking in a P2A-Venus chimeric gene downstream of a Cdh1 gene.

Tbx3-P2A-tdTomato KI vector: a knock-in vector for knocking in a P2A-tdTomato chimeric gene downstream of a Tbx3 gene.

Tbx3-P2A-Venus KI vector: a template plasmid for knocking in a P2A-Venus chimeric gene downstream of a Tbx3 gene.

Cdh1-aP2A-tdTomato KI vector: a knock-in vector for knocking in an aP2A-tdTomato chimeric gene downstream of a Cdh1 gene.

Cdh1-aP2A-Venus KI vector: a knock-in vector for knocking in an aP2A-Venus chimeric gene downstream of a Cdh1 gene.

Tbx3-P2A-Neo KI vector: a knock-in vector for knocking in a P2A-Neo chimeric gene downstream of a Tbx3 gene.

Cdh1-P2A-AIMS: an AIMS cell having each of a Cdh1-P2A-tdTomato chimeric gene and a Cdh1-P2A-Venus chimeric gene at Cdh1 loci of both alleles.

Tbx3-P2A-AIMS: an AIMS cell having each of a Tbx3-P2A-tdTomato chimeric gene and a Tbx3-P2A-Venus chimeric gene at Tbx3 loci of both alleles.

Cdh1-aP2A-AIMS: an AIMS cell having each of a Cdh1-aP2A-tdTomato chimeric gene and a Cdh1-aP2A-Venus chimeric gene at Cdh1 loci of both alleles.

P2A (mismatch): a spacer sequence having a 1-base mismatch with respect to a target sequence within a P2A peptide coding sequence.

aP2A (mismatch): a spacer sequence having a 1-base mismatch with respect to a target sequence within an aP2A sequence.

P2A (nX): a spacer sequence which targets a P2A peptide coding sequence and in which n nucleotide residue X has been added to the 5'-end.

aP2A (nX): a spacer sequence which targets an aP2A sequence and in which n nucleotide residue X's have been added to the 5'-end.

P2A (5'-addition): a spacer sequence which targets a P2A peptide coding sequence and in which an arbitrary number of nucleotide residues has been added to the 5'-end.

aP2A (5'-addition): a spacer sequence which targets an aP2A sequence and in which an arbitrary number of nucleotide residues has been added to the 5'-end.

P2A (mismatch_nX): a spacer sequence which has a 1-base mismatch with respect to a target sequence within a P2A peptide coding sequence and in which n nucleotide residue X has been added to the 5'-end.

Plasmids, linkers, primers, and the like used in the following examples are shown in Tables 3 to 5.

TABLE 3

| Sequence name | Description of sequence | SEQ ID NO. |
|---|---|---|
| PX459 | pSpCas9(BB)-2A-Puro (PX459) V2.0 plasmid | 1 |
| p. KW505-1 | Expression vector for sgRNA (no spacer) Produced by being digested from PX459 by KpnI + NotI, smoothed with T4 polimerase, and ligated | 2 |
| p. KW10-2 | Tbx3-P2A-tdTomato KI vector (no T-easy vector backbone sequence) | 3 |
| p. KW13-3 | Tbx3-P2A-Venus KI vector (no T-easy vector backbone sequence) | 4 |
| p. NT9-6 | Cdh1-P2A-tdTomato KI vector (no T-easy vector backbone sequence) | 5 |
| p. NT8-12 | Cdh1-P2A-Venus KI vector (no T-easy vector backbone sequence) | 6 |
| p. KW110-1 | Cdh1-aP2A-tdTomato KI vector (no T-easy vector backbone sequence) | 7 |

TABLE 3-continued

| Sequence name | Description of sequence | SEQ ID NO. |
|---|---|---|
| p. KW111-7 | Cdh1-aP2A-Venus KI vector (no T-easy vector backbone sequence) | 8 |
| hSpCas9 | hSpCas9 sequence in PX459 vector 3 × Flag and NLS are added to 5'-end, and NLS is added to 3'- end | 9 |
| Tbx3 5'-homology arm | 5'-arm of Tbx3-AIMS reporter KI vector KpnI site is added to 3'-end | 10 |
| Tbx3 3'-homology arm | 3'-arm of Tbx3-AIMS reporter KI vector SalI site is added to 5'-end, and NsiI site is added to 3'-end | 11 |
| Cdh1 5'-homology arm | 5'-arm of Cdh1-AIMS reporter KI vector KpnI site is added to 3'-end | 12 |
| Cdh1 3'-homology arm | 3'-arm of Cdh1-AIMS reporter KI vector SalI site is added to 5'-end | 13 |
| P2A | P2A peptide coding sequence | 14 |
| aP2A | aP2A sequence | 15 |
| tdTomato | tdTomato coding sequence | 16 |
| Venus | Venus coding sequence | 17 |

TABLE 4

| Sequence name | Description of sequence | SEQ ID NO. |
|---|---|---|
| Pr. KW535 | Primer (F) for amplification of Tbx3 5'-homology arm | 18 |
| Pr. KW536 | Primer (R) for amplification of Tbx3 5'-homology arm KpnI site is added to 3'-end | 19 |
| Pr. KW539 | Primer (F) for amplification of Tbx3 3'-homology arm SalI site is added to 5'-end | 20 |
| Pr. KW540 | Primer (R) for amplification of Tbx3 3'-homology arm NsiI site is added to 3'-end | 21 |
| Pr. NT7 | Primer (F) for amplification of Cdh1 5'-homology arm SacII site is added to 5'-end | 22 |
| Pr. NT8 | Primer (R) for amplification of Cdh1 5'-homology arm KpnI site is added to 3'-end | 23 |
| Pr. NT10 | Primer (F) for amplification of Cdh1 3'-homology arm SalI site is added to 5'-end | 24 |
| Pr. NT11 | Primer (R) for amplification of Cdh1 3'-homology arm | 25 |
| Pr. KW550 | Primer (F) for amplification of tdTomato KpnI + P2A (7-72) site is added to 5'-end | 26 |
| Pr. KW554 | Primer (R) for amplification of tdTomato SalI + P2A site is added to 3'-end Primer is set at outer side (vector side) of tdTomato coding | 27 |
| Pr. KW550_2 | Primer (F) for amplification of Venus KpnI + P2A (7-72) site is added to 5'-end | 28 |
| Pr. KW551 | Primer (R) for amplification of Venus SalI site is added to 3'-end | 29 |
| Pr. KWTV6 | Primer (F) for amplification of Neo + pA, and KpnI + P2A (7-72) site is added to 5'-end PCR amplification using Rosa26 mT/mG plasmid (plasmid #17787 of addgene) as template | 30 |
| Pr. KWTV7 | Primer (F) for amplification of Neo + pA, and KpnI + aP2A (7-72) site is added to 5'-end PCR amplification using Rosa26 mT/mG plasmid (plasmid #17787 of addgene) as template | 31 |
| Pr. KWTV8 | Primer (R) for amplification of Neo + pA, and SalI site is added to 3'-end PCR amplification using Rosa26 mT/mG plasmid (plasmid #17787 of addgene) as template | 32 |
| Pr. KW543 | Primer (F) for genotyping of Tbx3-tdTomato KI Set at genome on outer side of 5'-arm | 33 |
| Pr. KW552 | Primer (R) for genotyping of Tbx3-tdTomato KI Set at 5'-upstream of tdTomato | 34 |
| Pr. KW553 | Primer (F) for genotyping of Tbx3-tdTomato KI Set at 3'-downstream of tdTomato | 35 |
| Pr. KW546 | Primer (R) for genotyping of Tbx3-tdTomato KI Set at genome on outer side of 3'-arm | 36 |
| Pr. KW543_2 | Primer (F) for genotyping of Tbx3-Venus KI Set at genome on outer side of 5'-arm | 37 |
| Pr. KW557 | Primer (R) for genotyping of Tbx3-Venus KI Set at 5'-upstream of Venus | 38 |

TABLE 4-continued

| Sequence name | Description of sequence | SEQ ID NO. |
|---|---|---|
| Pr. KW558 | Primer (F) for genotyping of Tbx3-Venus KI Set at 3'-downstream of Venus | 39 |
| Pr. KW546_2 | Primer (R) for genotyping of Tbx3-Venus KI Set at genome on outer side of 3'-arm | 40 |

TABLE 5

| Sequence name | Description of sequence | SEQ ID NO. |
|---|---|---|
| Pr. KW541 | Primer (F) for PCR for detecting wild-type sequence after Tbx3-tdTomato (Venus) KI, and PCR for detecting indel after CRISPR-Cas9 action | 41 |
| Pr. KW542 | Primer (R) for PCR for detecting wild-type sequence after Tbx3-tdTomato (Venns) KI, and PCR for detecting indel after CRISPR-Cas9 action | 42 |
| Pr. NT14 | Primer (F) for genotyping of Cdh1-tdTomato KI Set at genome on outer side of 5'-arm | 43 |
| Pr. KW552_2 | Primer (R) for genotyping of Cdh1-tdTomato KI Set at 5'-upstream of tdTomato | 44 |
| Pr. KW553_2 | Primer (F) for genotyping of Cdh1-tdTomato KI Set at 3'-downstream of tdTomato | 45 |
| Pr. NT15 | Primer (R) for genotyping of Cdh1-tdTomato KI Set at genome on outer side of 3'-arm | 46 |
| Pr. NT14_2 | Primer (F) for genotyping of Cdh1-Venus KI Set at genome on outer side of 5'-arm | 47 |
| Pr. KW557_2 | Primer (R) for genotyping of Cdh1-Venus KI Set at 5'-upstream of Venus | 48 |
| Pr. KW558_2 | Primer (F) for genotyping of Cdh1-Venus KI Set at 3'-downstream of Venus | 49 |
| Pr. NT15_2 | Primer (R) for genotyping of Cdh1-Venus KI Set at genome on outer side of 3'-arm | 50 |
| Pr. NT12 | Primer (F) for PCR for detecting wild-type sequence after Tbx3-tdTomato (Venus) KI, and PCR for detecting indel after CRISPR-Cas9 action | 51 |
| Pr. NT13 | Primer (R) for PCR for detecting wild-type sequence after Tbx3-tdTomato (Venus) KI, and PCR for detecting indel after CRISPR-Cas9 action | 52 |
| Pr. KW1117 | Primer (F) for PCR for detecting wild-type sequence after Tbx3-tdTomato (Venus) KI, and PCR for detecting indel after CRISPR-Cas9 action | 53 |
| Pr. KW1118 | Primer (R) for PCR for detecting wild-type sequence after Tbx3-tdTomato (Venus) KI, and PCR for detecting indel after CRISPR-Cas9 action | 54 |
| Pr. KW880 | Primer (F) for PCR for detecting indel in Rosa26 region | 55 |
| Pr. KW881 | Primer (R) for PCR for detecting indel in Rosa26 region | 56 |
| Pr. KW886 | Primer (F) for PCR for detecting indel in Albmin region | 57 |
| Pr. KW887 | Primer (R) for PCR for detecting indel in Albmin region | 58 |

[Example 1] Culture of Mouse ES Cells

Mouse ES cells were cultured in a Dulbecco's modified Eagle's medium (DMEM; Nacalai Tesque). The DMEM used for the culture was a medium which contained 2 mM of Glutamax (Nacalai Tesque), 1× non-essential amino acid (NEAA) (Nacalai Tesque), 1 mM of sodium pyruvate, 100 U/mL of penicillin, 100 μg/mL of streptomycin (P/S) (Nacalai Tesque), 0.1 mM of 2-mercaptoethanol (Sigma), and 15% of fetal bovine serum (FBS) (GIBCO), and into which 1 μM or 0.2 μM of PD0325901 (Sigma), 3 M of CHIR99021 (Cayman), and 1,000 U/mL of recombinant mouse LIF (Millipore) were further added. The cells were maintained at 37° C. and 5% $CO_2$ under feeder-free conditions. At the time of cell subculture, Y-27632 (10 μM, Sigma) was added.

[Example 2] Construction of AIMS (Outline of AIMS)

Figure 1B:
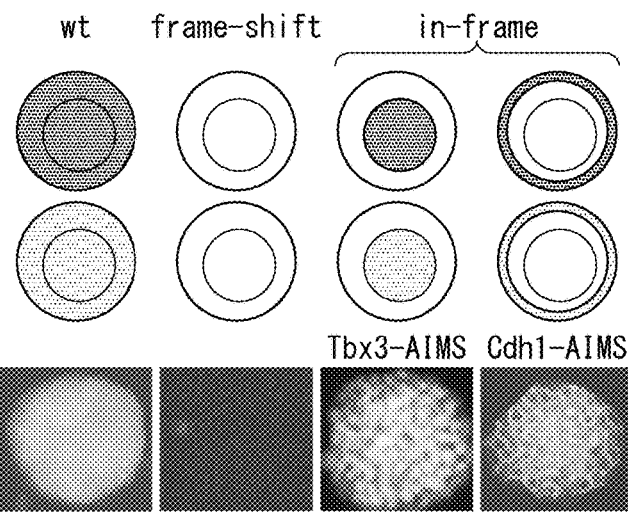
Figure 1C:
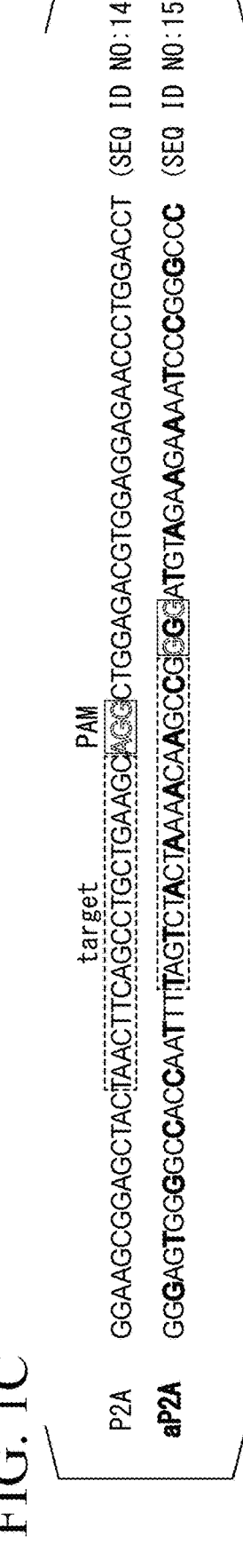

FIGS. 1A to 1C are diagrams showing an outline of an AIMS constructed in the present example. FIG. 1A is a diagram showing a genetic constitution of an AIMS cell produced in the present example, and FIG. 1B is a diagram showing a method of evaluating an indel by the AIMS.

In the AIMS cell of present example, Cdh1 (E-cadherin gene) or Tbx3 (TBX3 protein gene) was used as a localized protein coding sequence. A P2A peptide coding sequence was used as a cleavage site coding sequence. A tdTomato gene was used as a first fluorescent protein coding sequence, and a Venus gene was used as a second fluorescent protein coding sequence. Accordingly, a first chimeric gene in a first allele has the structure of Cdh1-P2A-tdTomato or Tbx3-

P2A-tdTomato, and a second chimeric gene in a second allele has the structure of Cdh1-P2A-Venus or Tbx3-P2A-Venus (FIG. 1A).

In the AIMS cell having the genetic constitution of FIG. 1A, chimeric proteins expressed from each of the chimeric genes were cleaved by a P2A peptide sequence and separated into a localized protein and a fluorescent protein. Therefore, the fluorescent protein was distributed throughout the cell without being localized ("wt" in FIG. 2B). Accordingly, when the AIMS cell of a wild strain (wt) was observed with a fluorescence microscope or the like, fluorescence was observed in the entire cell.

On the other hand, when genome editing by the CRISPR/Cas system was performed using sgRNA targeting a P2A coding sequence, expression and localization of the fluorescent protein changed according to the type of indel introduced into the P2A peptide coding sequence by the genome editing. That is, in a case where a frame-shift indel was introduced into the P2A coding sequence, the fluorescent protein was not expressed due to the frame-shift (frame-shift in FIG. 1B).

Furthermore, when an in-frame indel was introduced into the P2A peptide coding sequence, the chimeric protein was not cleaved by the P2A peptide. Therefore, the chimeric protein expressed from the first or second chimeric gene was localized within the cell according to the type of localized protein without being cleaved by the P2A peptide sequence. In a case where the localized protein was Tbx3, the AIMS protein was localized to the nucleus (Tbx3-AIMS of in-frame in FIG. 1B). In a case where the localized protein was Cdh1, the AIMS protein was localized to the cell membrane (Cdh1-AIMS of in-frame in FIG. 1B).

Accordingly, in a case where fluorescence of both tdTomato and Venus disappeared or was localized, it can be determined that an indel occurred in both the first allele (P2A-tdTomato allele) and the second allele (P2A-Venus allele). In a case where fluorescence of only one of tdTomato and Venus disappeared or was localized, it can be determined that an indel occurred in only one of the P2A-tdTomato allele and the P2A-Venus allele. In a case where fluorescence of both tdTomato and Venus did not disappear or was not localized, it can be determined that an indel did not occur in both of the P2A-tdTomato allele and the P2A-Venus allele.

As described above, by using the AIMS cell, it is possible to evaluate each of a biallelic indel introduction percentage and a monoallelic indel introduction percentage.

FIG. 1C shows a P2A coding sequence used to produce AIMS cells in the present example. A region surrounded by "target" in the figure is a target sequence of sgRNA. In the figure, a sequence shown as aP2A is a sequence in which a silent mutation was introduced into the P2A coding sequence. In production of AIMS cells described below, any one of the P2A coding sequence and the aP2A coding sequence was used.

(Construction of Knock-In Plasmid for AIMS Cell Production)

A 5'-arm and a 3'-arm of Cdh1 were ligated to a plasmid containing a P2A-Venus chimeric gene or a plasmid containing a P2A-tdTomato chimeric gene, and thereby a Cdh1-P2A-tdTomato KI vector and a Cdh1-P2A-tdTomato KI vector were produced. The 5'-arm of Cdh1 was designed such that ends of a Cdh1 coding sequence were linked in-frame to the P2A coding sequence so that each of E-cadherin (Cdh1) and a fluorescent protein (tdTomato or Venus) was produced independently.

A Tbx3-P2A-tdTomato KI vector and a Tbx3-P2A-tdTomato KI vector were produced in the same method as described above except that a 5'-arm and a 3'-arm of Tbx3 were used instead of the 5'-arm and 3'-arm of Cdh1.

A Cdh1-aP2A-tdTomato KI vector and a Cdh1-aP2A-tdTomato KI vector were produced in the same method as described above except that an aP2A sequence was used instead of the P2A sequence.

(Construction of all-In-One CRISPR Plasmid)

An adapter linker (SEQ ID NOs: 63 and 64) for sgRNA containing a coding sequence of a spacer sequence targeting a target sequence (3'-CCAGTTTGGTCAAATCTGCCAGT-5' (SEQ ID NO: 94)) in Tbx was ligated to a BpiI site of PX459, and thereby an all-in-one CRISPR plasmid for AIMS cell production was produced. In the same manner, an adapter linker (SEQ ID NOs: 65 and 66) for sgRNA containing a coding sequence of a spacer sequence targeting a sequence in Cdh was ligated to a BpiI site of PX459, and thereby an all-in-one CRISPR plasmid for AIMS cell production was produced. sgRNA targeting the downstream of a stop codon was designed using CRISPR DESIGN (crispr.mit.edu/).

(Production of AIMS Cells)

The all-in-one CRISPR plasmid, the Cdh1-P2A-tdTomato KI vector, and the Cdh1-P2A-Venus KI vector, which were produced above, were introduced into mouse ES cells at the same time using Lipofectamine (registered trademark) 3000 (Thermo Fisher SCIENTIFIC). ES cells separated with trypsin (Nacalai Tesque) were seeded in 500 μL of a 2iL+Y medium dispensed into a gelatin-coated 24-well plate. A complex of nucleic acid-Lipofectamine 3000 was prepared according to the standard protocol of Lipofectamine 3000. 1 μL of the Lipofectamine 3000 was added to 25 μL of an Opti-MEM medium (Thermo Fisher SCIENTIFIC). Furthermore, 250 ng of the above three plasmids and 1 μL of a P3000 reagent were added to another 25 μL of an Opti-MEM medium and mixed. These mixed solution were mixed together and incubated at room temperature for 5 minutes. Thereafter, the mixed solution was added into the 24-well plate in which the ES cells were seeded. After the cells spontaneously settled to the bottom of the plate, the plate was centrifuged at 600 g for 1 hour at 37° C. and then incubated overnight. After 1 or 2 days from transfection, cells were treated with puromycin (12 μg/mL) for 24 to 48 hours. Puromycin-resistant cells selected by the puromycin treatment were cultured for several days in the absence of puromycin, and dual color-positive colonies were collected. The genotype of the collected colonies was confirmed by PCR. Cells, in which introduction of each of the Cdh1-P2A-tdTomat chimeric gene and the Cdh1-P2A-Venus chimeric gene were confirmed in each of both alleles, were used as Cdh1-P2A-AIMS.

Tbx3-P2A-AIMS was produced in the same method as described above except that the Tbx3-P2A-Venus KI vector and the Tbx3-P2A-tdTomato KI vector were used instead of the Cdh1-P2A-Venus KI vector and the Cdh1-P2A-tdTomato KI vector.

Cdh1-aP2A-AIMS was produced in the same method as described above except that the Cdh1-aP2A-Venus KI vector and the Cdh1-aP2A-tdTomato KI vector were used instead of the Cdh1-P2A-Venus KI vector and the Cdh1-P2A-tdTomato KI vector.

(Indel Pattern Analysis Using AIMS Cells)

The analysis of an indel pattern using AIMS cells was performed as follows.

Figure 2A:
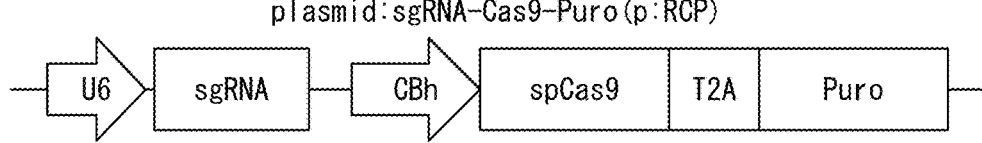
FIG. 2A is a diagram showing a configuration of a plasmid used for genome editing in Examples.

A target sequence was set within the P2A peptide coding sequence or within the aP2A sequence to design sgRNA. A coding sequence of a spacer sequence of the sgRNA was ligated to a BpiI site of PX459 to produce a p: RCP. The structure of the p: RCP used in the example is shown in FIG. 2A.

Figure 2B:
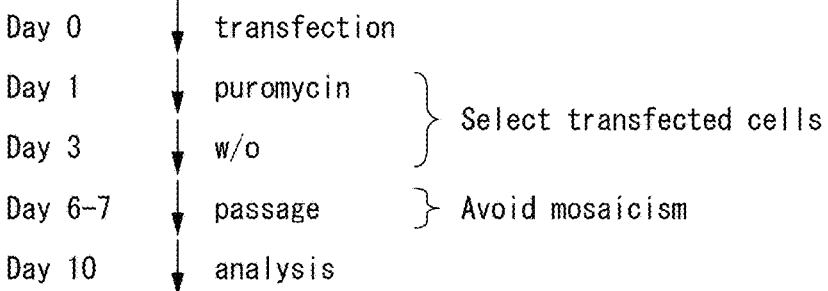
FIG. 2B is a diagram showing an operation procedure after transfection of the plasmid used for genome editing in Examples.

The p: RCP was transfected into an AIMS cell (Cdh1-P2A-AIMS, Tbx3-P2A-AIMS, or Cdh1-aP2A-AIMS) using Lipofectamine (registered trademark) 3000 (Thermo Fisher SCIENTIFIC). Transfection and puromycin treatment were performed in the same method as described in the section of "(Production of AIMS cells)" described above except that AIMS cells were used as cells, and the p: RCP was used as a plasmid. Puromycin-resistant cells selected by the puromycin treatment were cultured for several days in the absence of puromycin and then subcultured and cloned. Fluorescence of tdTomato and Venus was observed for the cloned cells using a fluorescence microscope (inverted research microscope IX73, Olympus), and indels in both alleles were evaluated. FIG. 2B shows a timeline from transfection to fluorescence analysis.

The indel pattern analysis of 30 to 170 clones was performed with a single transfection. Transfection and subsequent indel pattern analysis were performed at least 3 times for one type of sgRNA.

[Example 3] Evaluation of Mismatch Method

Whether introduction percentages of a biallelic indel and a monoallelic indel are changed by introducing a 1-base mismatch with respect to a target sequence into a spacer sequence of sgRNA was investigated.

Figure 3A:
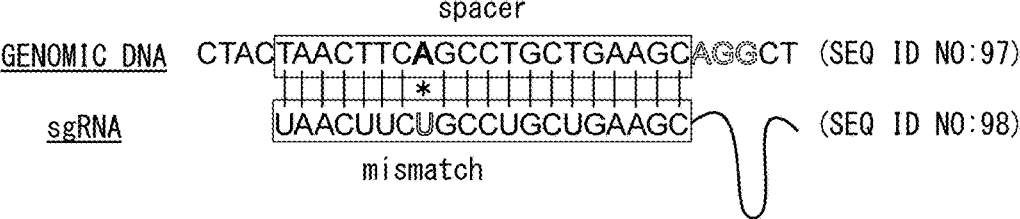
FIGS. 3A to 3B show results of investigating whether introduction percentages of a biallelic indel and a monoallelic indel are changed by introducing a 1-base mismatch with respect to a target sequence into a spacer sequence of sgRNA.

Each of 1-base mismatch spacer sequences, in which any one base of a target sequence (TAACTTCAGCCTGCT-GAAGC: SEQ ID NO: 95) of P2A was substituted with a different base, was designed (refer to FIG. 3A). An adapter sequence for ligation to a BpiI site of PX459 was added to a coding sequence of the spacer sequence having a 1-base mismatch at the base (1st position) adjacent to a PAM, and thereby an adapter linker (SEQ ID NOs: 69 and 70) for 1-base mismatch sgRNA was produced. By adding the same adapter sequence, each of adapter linkers for each of 1-base mismatch sgRNAs, in which a location of a mismatched base was at the 2nd to 20th position (where a base adjacent to a PAM was the 1st position, followed by the 2nd position to the 20th position from 3' toward 5'), was produced.

Sequences of adapter linkers for sgRNA having no mismatch in a P2A target sequence are set forth in SEQ ID NOs: 67 and 68.

In the same manner, each of 1-base mismatch spacer sequences, in which any one of a target sequence (TAGTC-TACTAAAACAAGCCG: SEQ ID NO: 96) of aP2A was substituted with a different base, was designed. An adapter sequence was added to a coding sequence of each of the spacer sequences, and thereby each of adapter linkers for each of 1-base mismatch sgRNAs was produced. Sequences of the adapter linker for 1-base mismatch sgRNA having a 1-base mismatch, at the base (1st position) adjacent to a PAM, with respect to a target sequence of aP2A are set forth in SEQ ID NOs: 73 and 74. The other adapter linkers for 1-base mismatch sgRNAs are the same except that locations of mismatches are different. Sequences of adapter linkers for sgRNA having no mismatch in an aP2A target sequence are set forth in SEQ ID NOs: 71 and 72. Each of these adapter linkers for 1-base mismatch sgRNAs was inserted into a BpiI sites of a PX459 plasmid, and thereby each of P2A (mismatch)_PX459's was produced.

Each of these P2A (mismatch)_PX459's was introduced into AIMS cells, and indels were evaluated.

Figure 3B:
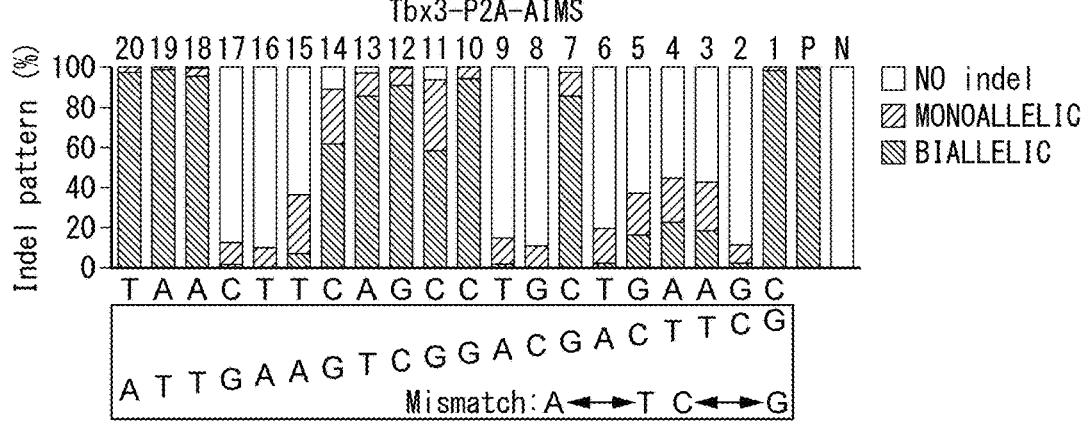

FIGS. 3A to 3D show the results. FIG. 3B shows results of performing indel pattern analysis using a Tbx3-P2A-AIMS as AIMS cells.

The horizontal axis of the graph in FIG. 3B shows a P2A target sequence, and a base after substitution in P2A (mismatch) is shown below the P2A target sequence. A distance (a location of each base when the base adjacent to a PAM is 1) from the PAM of the substituted base is shown at the upper part of the graph. "P" is a case in which P2A_PX459 (no mismatch) was used, and "N" is a case in which PX459 (no spacer sequence) was used.

As shown in FIG. 3B, a biallelic indel was introduced by almost 100% in a case in which P2A PX459 was used. On the other hand, in a case in which P2A (mismatch)_PX459 was used, a monoallelic indel introduction percentage was high. Furthermore, differences were shown in the indel introduction tendency depending on locations at which a mismatch was introduced.

Figure 3C:
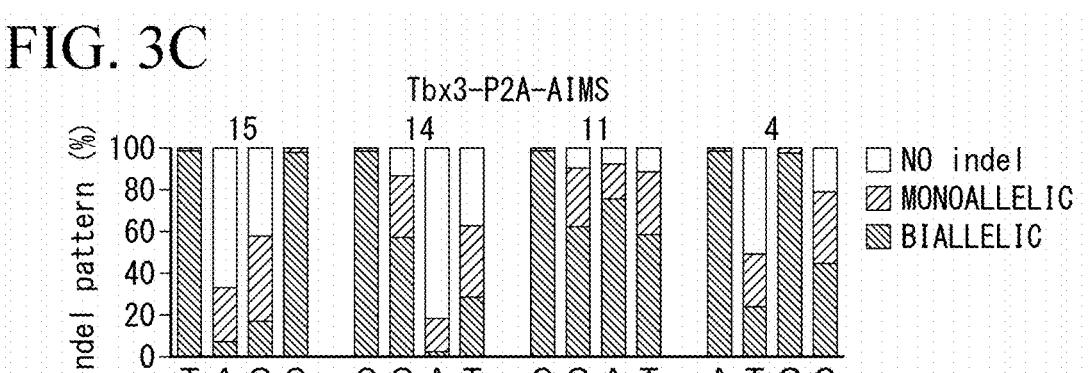
FIG. 3C shows results of performing indel pattern analysis using a Tbx3-P2A-AIMS as AIMS cells.

FIG. 3C shows results of performing indel pattern analysis using a Tbx3-P2A-AIMS as AIMS cells. The upper part of the graph of FIG. 3C shows locations of a target sequence from a PAM, and a horizontal axis of the graph shows bases in a spacer sequence which correspond to the locations. Bases underlined are bases that match the target sequence.

As shown in FIG. 3C, differences were shown in indel introduction percentages, biallelic indel introduction percentages, and monoallelic indel introduction percentages, depending on locations at which a mismatch was introduced, and the type of mismatched base.

Figure 3D:
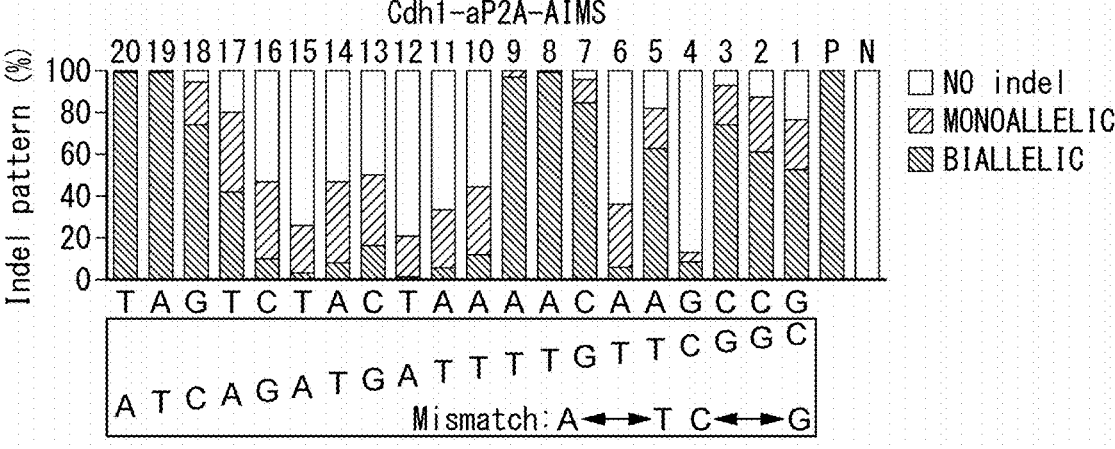
FIG. 3D shows results of performing indel pattern analysis using a Cdh1-aP2A-AIMS as AIMS cells.

FIG. 3D shows results of performing indel pattern analysis using a Cdh1-aP2A-AIMS as AIMS cells. Notations in the graph of FIG. 3D is the same as those in FIG. 3B.

As shown in FIG. 3D, biallelic indels were introduced by almost 100% in a case where the completely matching sgRNAs were used. On the other hand, in a case in which aP2A (mismatch)_PX459 was used, a monoallelic indel introduction percentage was high. Furthermore, differences were shown in the indel introduction tendency depending on locations at which a mismatch was introduced. From FIG. 3B, differences were shown in the indel introduction tendency.

Based on the above results, it was confirmed that a monoallelic indel proportion can be adjusted by selecting a location at which a 1-base mismatch is introduced and the type of mismatched base.

[Example 4] Evaluation of 5'-Nucleotide Addition Method (Indel Introduction by P2A (5'-Addition)_PX459)

Whether introduction percentages of a biallelic indel and a monoallelic indel are changed by adding nucleotide residues to the 5'-end of a spacer sequence of sgRNA was investigated.

Figure 4A:
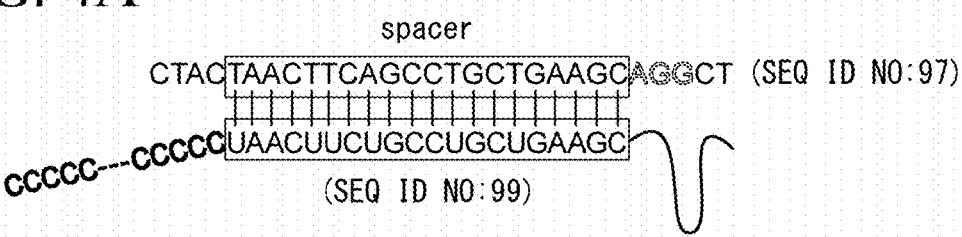
FIGS. 4A to 4F show results of investigating whether introduction percentages of a biallelic indel and a monoallelic indel are changed by adding nucleotide residues to the 5'-end of a spacer sequence of sgRNA.

Each of spacer sequences in which 0 to 40 cytosines had been added to the 5'-side of a P2A target sequence was designed (refer to FIG. 4A). Adapter sequences for ligation to a BpiI site of PX459 were added to coding sequences of these spacer sequences, and thereby each of adapter linkers for 5'-C-added sgRNAs was produced.

In the same manner, each of spacer sequences in which 15 guanines, adenines, or uracils had been added to the 5'-side of a target sequence of P2A was designed. An adapter sequence was added to a coding sequence of each of the spacer sequences, and thereby each of adapter linkers for P2A (15G), P2A (15A), and P2A (15U) sgRNAs was produced. Each of these adapter linkers for sgRNAs was inserted into a BpiI sites of a PX459 plasmid, and thereby each of P2A (5'-addition)_PX459's was produced.

As an example of the adapter linker for sgRNA used for producing the above-described plasmid, sequences of the adapter linker for sgRNA in which 15G's had been added to the 5'-end of the spacer sequence are set forth in SEQ ID NOs: 75 and 76. All the other adapter linkers for sgRNAs have the same sequences except that the number and type of nucleotide residues added to the 5'-end of the spacer sequence are different. Sequences of the adapter linker for sRNA in which 5C's had been added to the 5'-end of the spacer sequence targeting aP2A are set forth in SEQ ID NOs: 81 and 82.

Each of the P2A (5'-addition)_PX459's produced above was introduced into AIMS cells, and indels were evaluated.

Figure 4B:
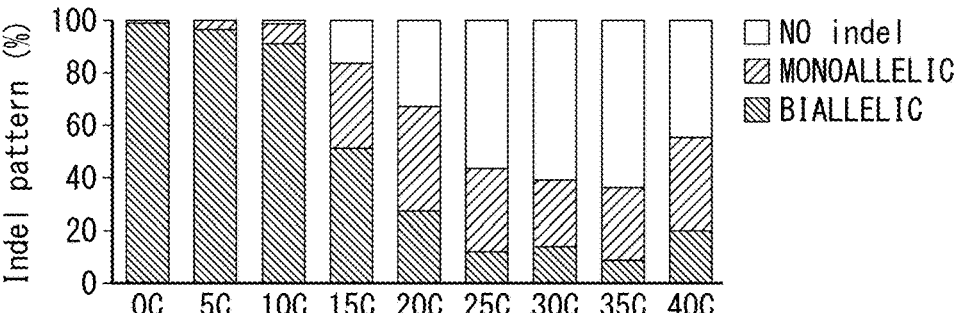
Figure 4C:
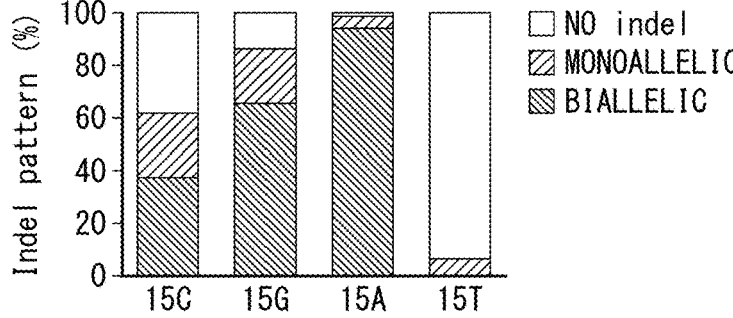

The results are shown in FIGS. 4B and 4C. FIG. 4B shows results of performing indel pattern analysis using a Cdh1-P2A-AIMS as AIMS cells.

The horizontal axis in the graph of FIG. 4B shows nucleotide residues added to the 5'-end of a target sequence. As shown in FIG. 4B, a biallelic indel was introduced by almost 100% in a case in which P2A_PX459 (0C) was used. Meanwhile, as the number of cytosines added increased, an indel introduction percentage decreased. Furthermore, as the number of cytosines added increased, a monoallelic indel introduction percentage increased. However, when the number of cytosines added was 25 or more, no difference was shown in the indel introduction tendency.

FIG. 4C shows results of performing indel pattern analysis using a Cdh1-P2A-AIMS as AIMS cells. Notations in the graph of FIG. 4C is the same as those in FIG. 4B. As shown in FIG. 4C, differences were shown in indel introduction percentages and monoallelic indel introduction percentages depending on the type of nucleotide added. In a case where adenosine (A) was added, an indel introduction percentage hardly decreased, and a monoallelic indel introduction percentage was also low. In the order of guanosine (G) and cytosine (C), an indel introduction percentage decreased, and a monoallelic indel introduction percentage increased. In a case where uridine (U) was added, an indel introduction percentage was significantly reduced, and biallelic indel introduction was hardly recognized.

Furthermore, it was also confirmed whether an indel introduction percentage was changed by adding a nucleotide residue to the 3'-end of a spacer sequence of sgRNA. P2A (3'-addition)_PX459 was produced by the same method as described above except that a sequence (SEQ ID NOs: 77 to 80) of an adapter linker for sgRNA, in which 5C's or 10C's had been added to the 3'-end of a spacer sequence, was used. The P2A (3'-addition)_PX459 was introduced into AIMS cells to evaluate an indel introduction percentage. As a result, an indel introduction percentage was almost 0% regardless of whether 5C's or 10C's had been added to the 3'-end. It is thought that the reason for this is because in a case where a sequence is added to the 3'-end of a spacer sequence, an extra sequence is interposed between the spacer sequence and a PAM sequence.

(Effect of Usage Amount of sgRNA Expression Plasmid on Indel Introduction Percentage)

There is a possibility that the decrease in indel introduction percentage upon addition of a nucleotide residue to the 5'-side of a target sequence may be caused by inhibition of sgRNA transcription due to additional nucleotide residues. Therefore, an effect on an indel introduction percentage by a usage amount of an sgRNA expression plasmid used for transfection was evaluated.

[Effect of Usage Amount of p: RCP During Transfection]

P2A PX459 was transfected using Tbx3-P2A-AIMS as mouse ES cells for AIMS. A usage amount of P2A_PX459 for transfection was 2.5 ng, 25 ng, 250 ng, or 2,500 ng.

Figure 4D:
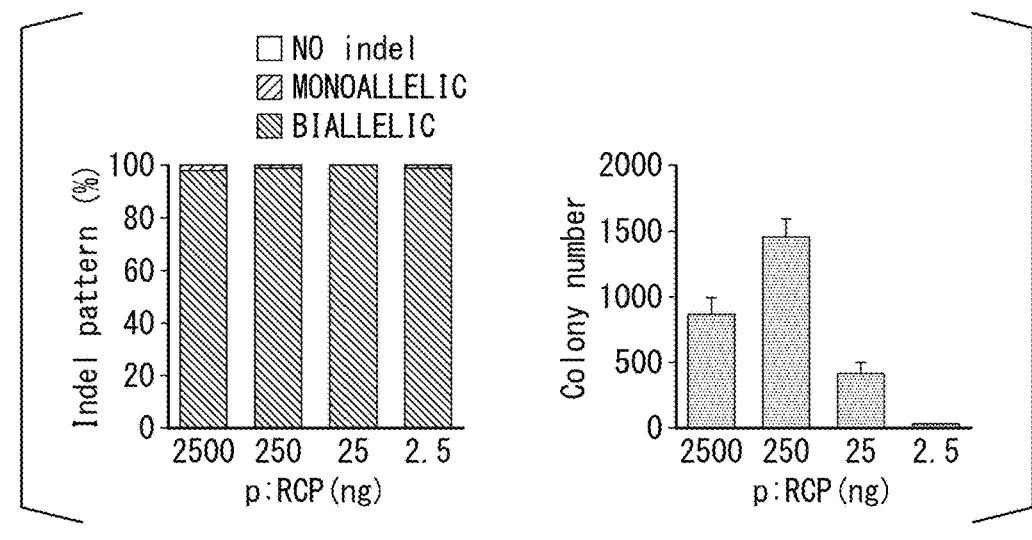

The results are shown in FIG. 4D. In FIG. 4D, the left graph shows the result of indel analysis, and the right graph shows the number of colonies obtained after transfection of P2A PX459. As shown in the right graph of FIG. 4D, when a usage amount of P2A_PX459 was reduced, the number of colonies decreased. It is thought that the reason for this is because as a usage amount of p: RCP during transfection is reduced, an introduction percentage of P2A_PX459 into AIMS cells decreases, and the number of cells becoming puromycin-resistant decreases. On the other hand, in cells that became puromycin-resistant, biallelic indels were introduced by almost 100%.

[Effect of Usage Amount of sgRNA Expression Plasmid During Transfection]

Since the p: RCP expressing all of the sgRNA, Cas9, and puromycin-resistant gene was used in the above-described test, there is a possibility that biallelic indels were introduced by almost 100% in puromycin-resistant cells obtained after the transfection. Therefore, after PX459 was cleaved by KpnI and NotI, the cleaved end was smoothed with T4 polymerase and ligated, and thereby PX459 (del_Cas9-T2A-Puro) was produced. A coding sequence of a spacer sequence targeting aP2A was inserted into a BpiI site of PX459 (del_Cas9-T2A-Puro), and thereby aP2A_PX459 (del_Cas9-T2A-Puro) was produced. aP2A_PX459 (del_Cas9-T2A-Puro) and a constant amount (250 ng) of PX459 (no spacer sequence) were co-transfected into AIMS cells while changing an amount (0 to 250 ng) of aP2A_PX459. Cdh1-aP2A-AIMS was used for the AIMS cells.

Figure 4E:
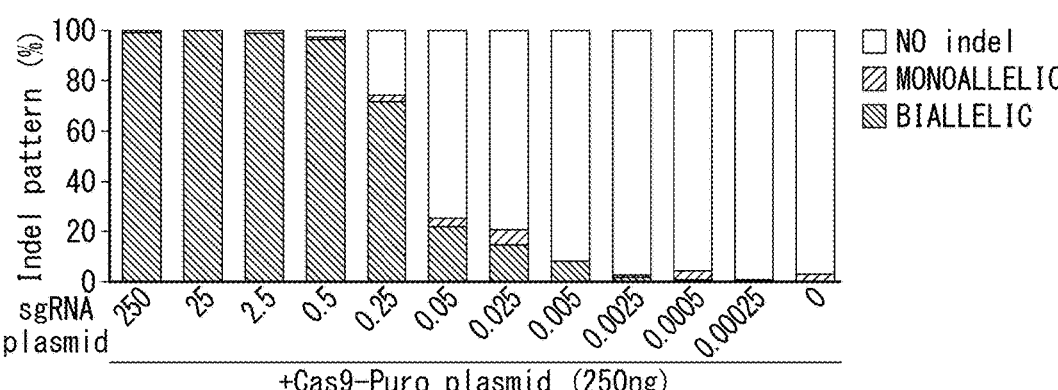

The results are shown in FIG. 4E. As a usage amount of aP2A_PX459 (del_Cas9-T2A-Puro) decreased, an indel introduction percentage decreased, but a monoallelic indel introduction percentage hardly increased.

Based on these results, it was confirmed that a monoallelic indel introduction percentage did not increase even when a usage amount of the sgRNA expression plasmid was reduced during transfection.

(Genome Editing of Rosa26 and Albumin Gene)

Each of the following adapter linker sequences was inserted into a BpiI site of PX459, and thereby each of 10C (8A) linker PX459 and 25C (23A) linker PX459 was produced. By inserting a coding sequence of a desired spacer sequence into the BPiI site of these plasmids, it is possible to express each of sgRNAs in which 10C's and 23C's had been added to the 5'-side. However, each of the 8th C of 10C and the 23rd C of 25C were substituted by A because an overhang sequence CACC for ligation to the BPiI site was introduced in these plasmids.

10C (8A) Adapter Linker:

(F)
(SEQ ID NO: 59)
5'-CACCGCCCCCCCACCGGGTCTTCGAGAAGACCT-3'

(R)
(SEQ ID NO: 60)
5'-AAACAGGTCTTCTCGAAGACCCGGTGGGGGGGC-3'

25C (23A) Adapter Linker:

(F)

(SEQ ID NO: 61)

5'-CACCGCCCCCCCCCCCCCCCCCCCCCCCCCACCGGGTCTTCGAGAAGACC

T-3'

(R)

(SEQ ID NO: 62)

5'-AAACAGGTCTTCTCGAAGACCCGGTGGGGGGGGGGGGGGGGGGGGG

C-3'

A coding sequence of a spacer sequence targeting Rosa26 or a coding sequence of a spacer sequence targeting the albumin gene (Alb) was inserted into the BPiI site of the 10C (8A) linker PX459 or the 25C (23A) linker PX459, and thereby each of Rosa26_PX459 (10C (8A)), Rosa26_PX459 (25C (23A)), Alb_PX459 (10C (8A)), and Alb_PX459 (25C (23A)) was produced. Sequences of the linker for producing sgRNA targeting Rosa26 are set forth in SEQ ID NOs: 87 and 88. Sequences of the linker for producing sgRNA targeting Alb are set forth in SEQ ID NOs: 89 and 90.

The Rosa26_PX459 (10C (8A)), Rosa26_PX459 (25C (23A)), Alb_PX459 (10C (8A)), or Alb_PX459 (25C (23A)), which were produced above, were introduced into wild-type ES cells. Transfection and puromycin treatment were performed in the same method as described in the section of "(Production of AIMS cells)" described above. Puromycin-resistant cells selected by the puromycin treatment were cultured for several days in the absence of puromycin and then subcultured and cloned. The genome was recovered from the colonies of the cloned cells, and the presence or absence of indels in each allele was determined by PCR and sequence analysis.

Figure 4F:
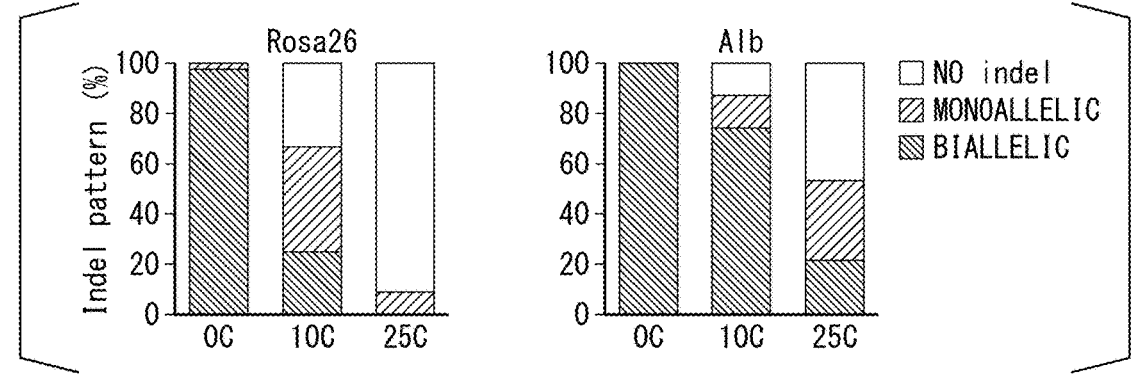

The results are shown in FIG. 4F. It was confirmed that by adding cytosine to the 5'-end of a spacer sequence, a monoallelic indel introduction percentage increased even in a case of targeting genomic regions such as Rosa26 and Alb.

Puromycin-resistant cells were selected by performing transfection and puromycin treatment in the same manner as in the method described in the section of "(Indel pattern analysis using AIMS cells)" of Example 2 except that wild-type mouse ES cells were used as cells for transfection, and the plasmid produced above was used as a plasmid for transfection. The obtained puromycin-resistant cells were cultured for several days in the absence of puromycin and then subcultured to obtain cloned colonies. Genomic DNA was extracted from the colonies, a DNA fragment containing a target sequence of sgRNA was amplified by PCR, and sequence analysis was performed to determine the presence or absence of indels. Sequences of a PCR primer for indel analysis in a case where Rosa26 was targeted are set forth in SEQ ID NOs: 55 and 56. Sequences of a PCR primer for indel analysis in a case where the albumin gene was targeted are set forth in SEQ ID NOs: 57 and 58.

The results are shown in FIG. 4F. The horizontal axis in the graph of FIG. 4F shows nucleotide residues added to the 5'-end of a target sequence.

Similar to the results in FIG. 4B, a biallelic indel was introduced by almost 100% in a case (0C) in which nucleotide addition was not performed. Meanwhile, in both of the Rosa26 and the albumin gene (Alb), an indel introduction percentage decreased as the number of cytosines added increased. Furthermore, a monoallelic indel introduction percentage increased by adding cytosine.

Based on these results, it was confirmed that a monoallelic indel introduction percentage increases by adding a nucleotide residue to the 5'-end of a target sequence even in a case where an intrinsic gene is targeted.

[Example 5] Homologous Recombination Test Using AIMS Cells (Outline of Evaluation Method)

Next, using AIMS cells, introduction percentages of homologous recombination not including indels were evaluated.

Figure 5A:
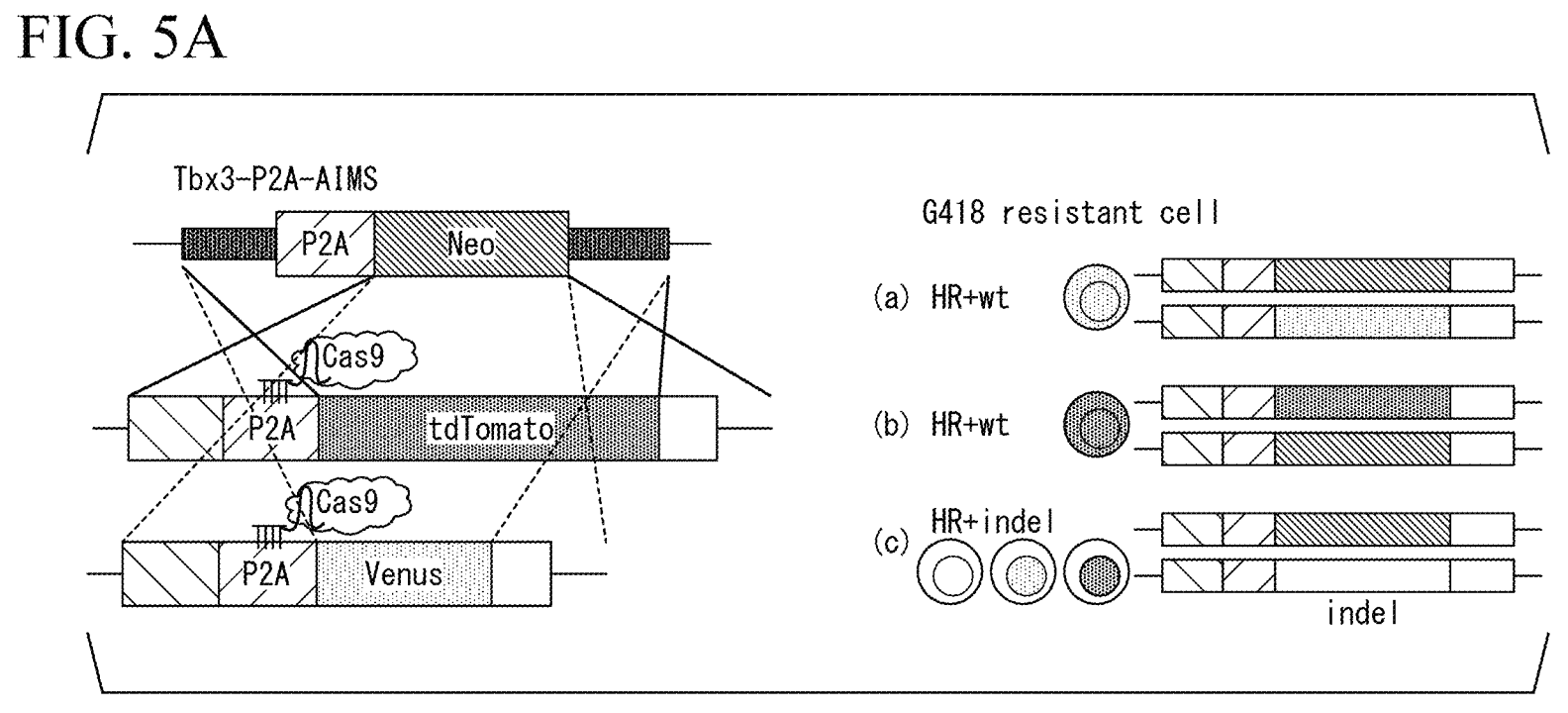

FIG. 5A is a diagram showing an outline of a method used in the present test. In the present test, a p: RCP targeting a sequence within a P2A coding sequence, and a Tbx3-P2A-Neo KI vector were co-transfected into Tbx3-P2A-AIMS. In the Tbx3-P2A-AIMS into which both of the plasmids had been introduced, first, sgRNA targeting P2A, and Cas9 were expressed from the all-in-one CRISPR plasmid, and a P2A coding sequence was cleaved by these sgRNA and Cas9. Next, a P2A-Neo chimeric gene was knocked in downstream of a Tbx3 gene by homologous recombination with the Tbx3-P2A-Neo KI vector (refer to the left figure in FIG. 5A). After the co-transfection, the cells were cultured in the presence of puromycin and then in the presence of geneticin, and thereby it was possible to select cells in which the P2A-Neo chimeric gene was knocked in by genome editing.

In cells in which the P2A-Neo chimeric gene was knocked in at a P2A-tdTomat allele and an indel was not contained in a P2A-Venus allele, fluorescence of the tdTomato disappeared, and fluorescence of the Venus was detected in the whole cell (right figure (a) of FIG. 5A). In cells in which the P2A-Neo chimeric gene was knocked in at a P2A-Venus allele and an indel was not contained in a P2A-tdTomato allele, fluorescence of the Venus disappeared, and fluorescence of the tdTomato was detected in the whole cell (right figure (b) of FIG. 5A). In cells in which the P2A-Neo chimeric gene was knocked in at a P2A-Venus allele or a P2A-tdTomato allele and a frame-shift indel was contained in the P2A-tdTomato allele or the P2A-Venus allele, fluorescence of both the Venus and the tdTomato disappeared (a left part in the right figure (c) of FIG. 5A). In cells in which the P2A-Neo chimeric gene was knocked in at a P2A-tdTomato allele and an in-frame indel was contained in a P2A-Venus allele, fluorescence of the tdTomato disappeared, and fluorescence of the Venus was localized in the nucleus (a middle part in the right figure (c) of FIG. 5A). In cells in which the P2A-Neo chimeric gene was knocked in at a P2A-Venus allele and an in-frame indel was contained in a P2A-tdTomato allele, fluorescence of the Venus disappeared, and fluorescence of the tdTomato was localized in the nucleus (a right part in the right figure (c) of FIG. 5A).

In this manner, it is possible to evaluate whether or not an indel is contained in an allele that has not been knocked in. Since it is very rare for both alleles to be knocked in at the same time, it was considered that the P2A-Neo chimeric gene was knocked in at one allele and a frame-shift indel occurred at the other allele in all the cells in which fluorescence of both the tdTomato and the Venus fluorescence disappeared.

(Test Method)

The P2A-Neo chimeric gene was amplified by PCR using a Rosa26 mT/mG plasmid (Addgene, plasmid #17787) as a template. Sequences of the primer used for PCR are set forth in SEQ ID NOs: 30 and 32. The P2A-Neo chimeric gene was substituted by a P2A-tdTomato chimeric gene of the Tbx3-P2A-tdTomato KI vector to produce a Tbx3-P2A-Neo KI vector.

A p: RCP containing a coding sequence of a spacer sequence that was a test subject, and the Tbx3-P2A-Neo KI vector were co-transfected into Tbx3-P2A-AIMS, and puromycin treatment was performed. Conditions for the co-transfection and the puromycin treatment were the same as those in the method described in the section of "(Indel pattern analysis using AIMS cells)" in Example 2.

Three days after the co-transfection, puromycin was removed, a medium containing geneticin (400 μg/mL, GIBCO) was added, and geneticin-resistant cells were selected. The obtained geneticin-resistant cells were cloned, and genotyping of 9 clones was performed. As a result, knock-in of the P2A-Neo chimeric gene was confirmed in all of the 9 clones. Based on these results, it was confirmed that most of the geneticin-resistant clones were knock-in clones of the P2A-Neo chimeric gene. Furthermore, because fluorescence of Tomato was observed in all of the 9 clones, it was determined that the knock-in was one-sided knock-in of the P2A-Venus allele.

Geneticin-resistant cells were selected by co-transfection by the above method and by performing puromycin treatment and geneticin treatment. For these cells, fluorescence of tdTomato and Venus was observed using a fluorescence microscope (inverted research microscope IX73, Olympus), and whether an indel was contained in an allele in which no knock-in occurred was evaluated. The analysis of 40 to 230 clones was performed with a single co-transfection. Transfection and subsequent indel analysis were performed at least 3 times for one type of sgRNA.

(Evaluation of Mismatch Method)

In the same manner as in Example 3, each of 1-base mismatch spacer sequences, in which any one of a target sequence (SEQ ID NO: 95) of P2A was substituted with a different base, was designed. An adapter sequence was added to a coding sequence of each of the spacer sequences, and thereby adapter linkers for each of 1-base mismatch sgRNAs were produced. Each of these adapter linkers for 1-base mismatch sgRNAs was inserted into a BpiI sites of a PX459 plasmid, and thereby each of P2A (mismatch)_PX459's was produced. Each of these P2A (mismatch)_PX459's was used as a p: RCP for co-transfection.

Figure 5B:
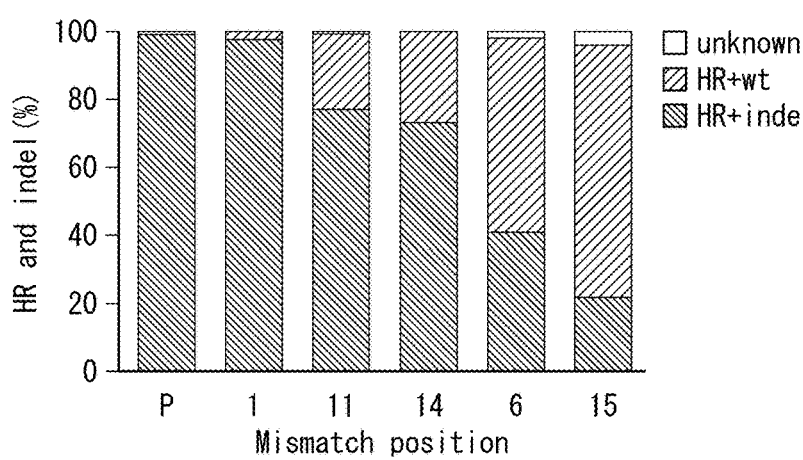

The results are shown in FIG. 5B. The horizontal axis in the graph of FIG. 5B shows a location (a location of each base when the base adjacent to PAM is 1) of a base substituted with respect to a target sequence of P2A. In a spacer sequence, A in a target sequence was substituted by T, T was substituted by A, C was substituted by G, and G was substituted by C. "P" is a case in which P2A_PX459 (no mismatch) was used. In the figure, "HR+wt" is a case in which homologous recombination (HR) was included in one allele and an indel was not contained in the other allele, and "HR+indel" is a case in which homologous recombination (HR) was included in one allele and an indel was contained in the other allele. "unknown" is cases other than these cases.

As shown in FIG. 5B, in a case where P2A_PX459 was used, a homologous recombination was a homologous recombination accompanying an indel by almost 100%. Meanwhile, in a case where P2A (mismatch)_PX459 was used, a proportion of homologous recombination not accompanying an indel increased. Furthermore, differences were shown in a proportion of homologous recombination not accompanying an indel depending on locations of a mismatch.

Based on the above results, it was confirmed that the mismatch method is effective as a method for inducing homologous recombination not accompanying an indel.

(Evaluation of 5'-Nucleotide Addition Method)

Each of spacer sequences in which 10 or 20 cytosines had been added to the 5'-side of a P2A target sequence (SEQ ID NO: 95) was designed. An adapter sequence was added to a coding sequence of each of these spacer sequences, and thereby each of adapter linkers for 5'-C-added sgRNAs was produced. Each of these adapter linkers for sgRNAs was inserted into a BpiI sites of a PX459 plasmid, and thereby each of P2A (5'-addition)_PX459's was produced. Each of these P2A (5'-addition)_PX459's was used as a p: RCP for co-transfection.

Figure 5C:
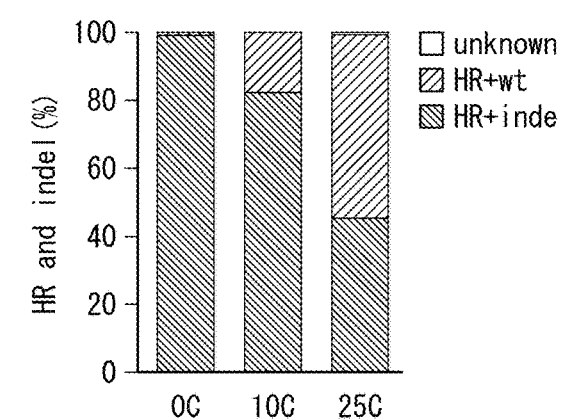

The results are shown in FIG. 5C. The horizontal axis in the graph of FIG. 5C shows nucleotide residues added to the 5'-end of a target sequence. "0C" is a case in which P2A_PX459 (without 5'-addition) was used. In the figure, the meanings of "HR+wt," "HR+indel," and "unknown" are the same as those in FIG. 5B.

As shown in FIG. 5C, in a case where P2A_PX459 was used, a homologous recombination was a homologous recombination accompanying an indel by almost 100%. Meanwhile, in a case where P2A (5')_PX459 was used, a proportion of homologous recombination not accompanying an indel increased. Furthermore, as the number of cytosines added increased, a proportion of homologous recombination not accompanying an indel increased.

Based on the above results, it was confirmed that the 5'-nucleotide addition method is effective as a method for inducing homologous recombination not accompanying an indel.

[Example 6] Combination of Mismatch Method and 5'-Nucleotide Addition Method

Whether a monoallelic indel introduction percentage increased by a combination of the mismatch method evaluated in Example 3 and the 5'-nucleotide addition method evaluated in Example 4 was tested. Tbx3-P2A-AIMS was used as AIMS cells.

Figure 6A:
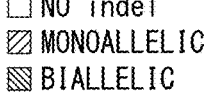
FIGS. 6A to 6C show results of investigating whether introduction percentages of a biallelic indel and a monoallelic indel are changed by combining introduction of a 1-base mismatch and addition of nucleotide residues to a 5'-end.
Figure 6A:
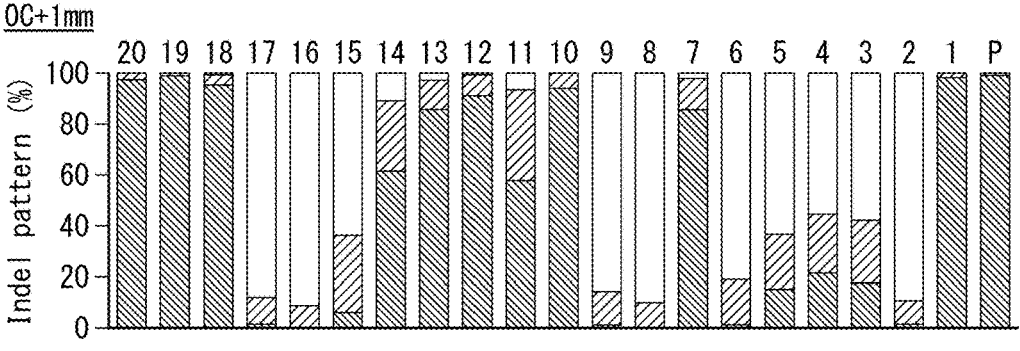

FIG. 6A shows results of using sgRNA having a 1-base mismatch with respect to a target sequence (SEQ ID NO: 95) of P2A. P2A (mismatch)_PX459 was introduced into Tbx3-P2A-AIMS, and indels were evaluated. A distance (a location of each base when the base adjacent to a PAM is 1) from the PAM of the substituted base is shown at the upper part of the graph. "P" is a case in which P2A_PX459 (no mismatch) was used. In a spacer sequence, A in a target sequence was substituted by T, T was substituted by A, C was substituted by G, and G was substituted by C.

In the same manner as in FIG. 3B of Example 3, a biallelic indel was introduced by almost 100% in a case in which P2A PX459 was used. On the other hand, in a case in which P2A (mismatch)_PX459 was used, a monoallelic indel introduction percentage was high.

Figure 6B:
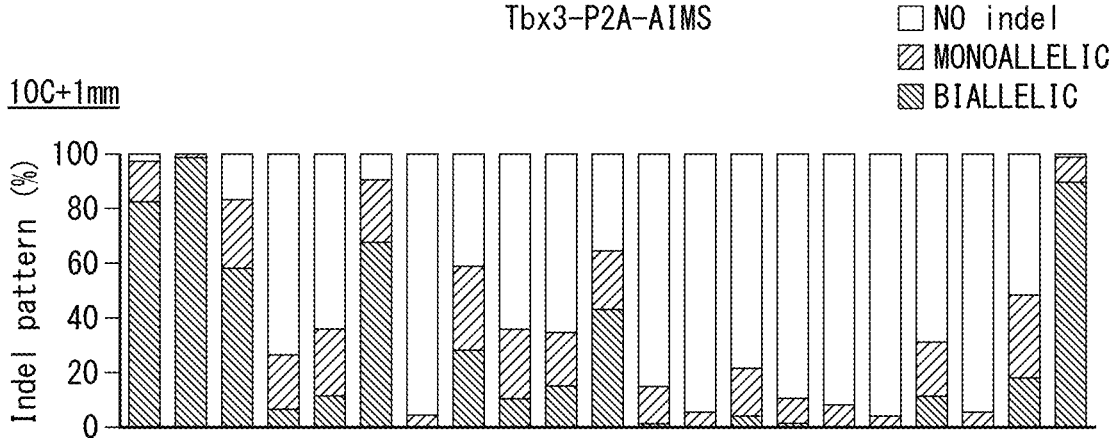

FIG. 6B shows results of using sgRNA containing a spacer sequence which has a 1-base mismatch with respect to a target sequence (SEQ ID NO: 95) of P2A and in which 10 cytosines were added to the 5'-end. P2A (mismatch_10C)_PX459 was introduced into Tbx3-P2A-AIMS, and indels were evaluated. A method of describing the graph and a method of substituting a base are the same as the case of FIG. 6A. "P" is a case in which P2A (10C (8A))_PX459 was used. In the above description, "P2A (10C (8A))" indicates that the 8th cytosine among 10 cytosines added to the 5'-end of a target sequence of P2A was substituted by adenosine.

In FIG. 6B, a monoallelic indel introduction percentage increased overall as compared to the results of FIG. 6A.

Figure 6C:
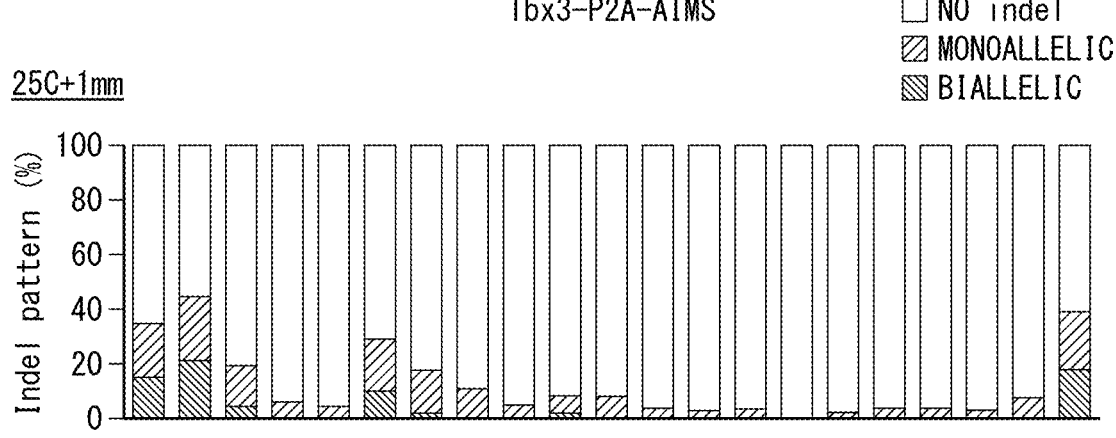

FIG. 6C shows results of using sgRNA containing a spacer sequence which has a 1-base mismatch with respect to a target sequence (SEQ ID NO: 95) of P2A and in which 25 cytosines were added to the 5'-end. P2A (mismatch_25C)_PX459 was introduced into Tbx3-P2A-AIMS, and indels were evaluated. A method of describing the graph and a method of substituting a base are the same as the case of FIG. 6A. "P" is a case in which P2A (25C (23A))_PX459 was used. In the above description, "P2A (25C (23A))" indicates that the 23rd cytosine among 25 cytosines added to the 5'-end of a target sequence of P2A was substituted by adenosine.

In FIG. 6C, an indel introduction percentage decreased as compared with the results of FIGS. 6A and 6B. In particular, a biallelic indel introduction percentage was greatly reduced. As a result, mismatch locations at which only a monoallelic indel had been induced were increased.

Based on these results, it was shown that a monoallelic indel introduction percentage can be controlled by combining the mismatch method and the 5'-nucleotide addition method.

[Example 7] Calculation of Indel Induction Ratio (Probability: P) and Prediction of Frequency of Monoallelic Indels Assuming that an indel induction ratio for a target region by CRISPR-Cas9 is P, a frequency of monoallelic indels, a frequency of biallelic indels, and a frequency no indels can be respectively represented by Formulas (m), (b), and (n).

$$\text{Frequency of monoallelic indels (mono)}=2\times P\times(1-P) \quad (m)$$

$$\text{Frequency of biallelic indels }(bi)=P^2 \quad (b)$$

$$\text{Frequency of no indels (none)}=(1-P)^2 \quad (n)$$

Assuming that mono+bi+none=1, P can be obtained by Formula (1).

$$P=(2\times bi+\text{mono})/2 \quad (1)$$

Therefore, based on the results of FIGS. 3B to 3D, 4B, and 6A to 6C, P values in each of the sgRNAs were calculated by Formula (1) above. Using these P values, frequencies of monoallelic indels in each of the sgRNAs were calculated by Formula (m) above.

Figure 7:
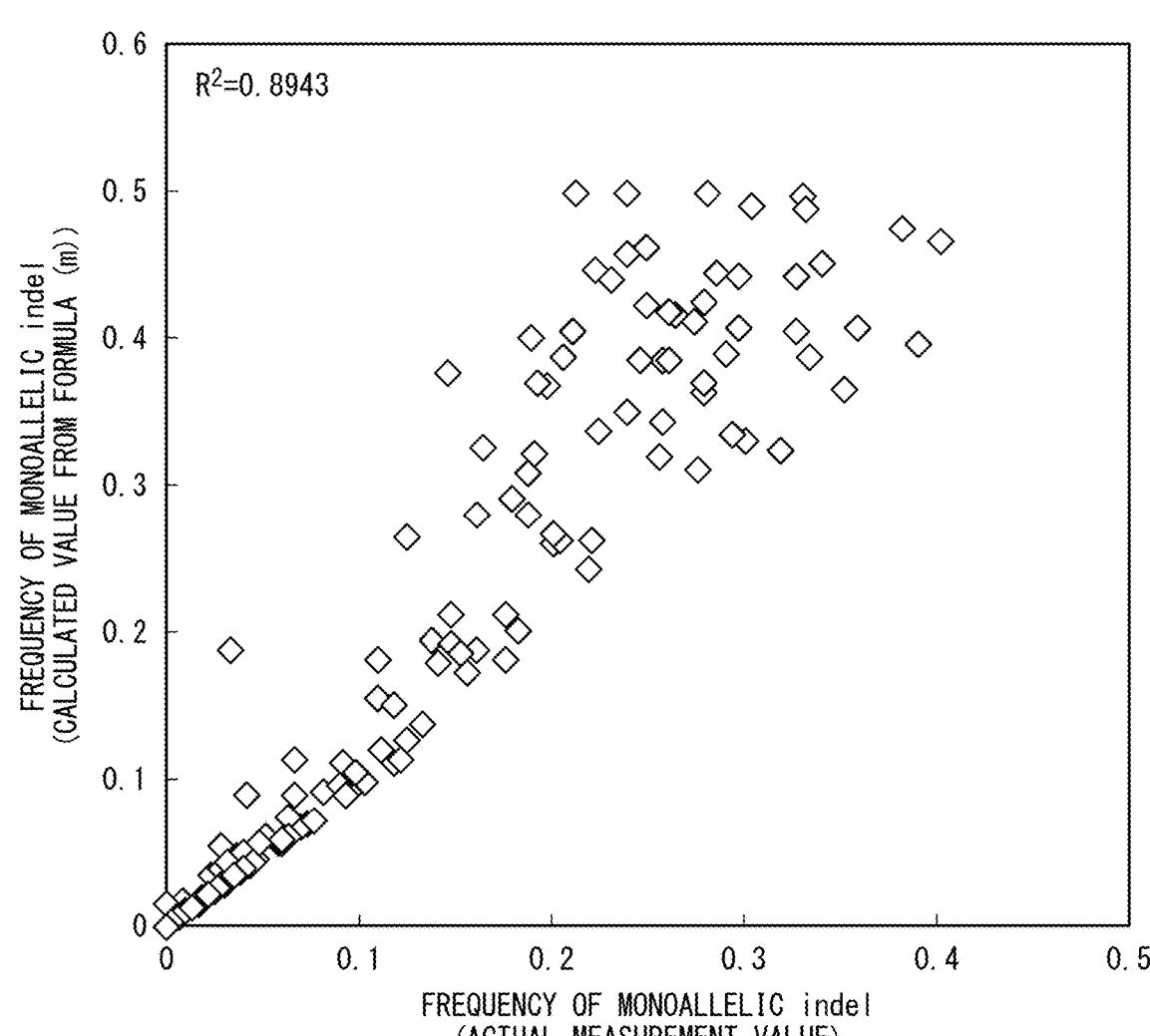
FIG. 7 shows a correlation between a frequency of monoallelic indels calculated by Formula (m) described in Example 7, and a frequency of monoallelic indels actually detected in FIGS. 3B to 3D, 4B, and 6A to 6C.

FIG. 7 shows a correlation between a frequency of monoallelic indels calculated by Formula (m) above, and a frequency of monoallelic indels actually detected in FIGS. 3B to 3D, 4B, and 6A to 6C.

As shown in FIG. 7, frequencies of monoallelic indels predicted by Formula (m) and frequencies of actually detected monoallelic indels showed a high correlation (R2=0.8943). Based on these results, it was shown that a frequency of monoallelic indels can be predicted by Formula (m).

[Example 8] Prediction of Indel Pattern (Pre-Demo-Prediction)

Figure 8A:
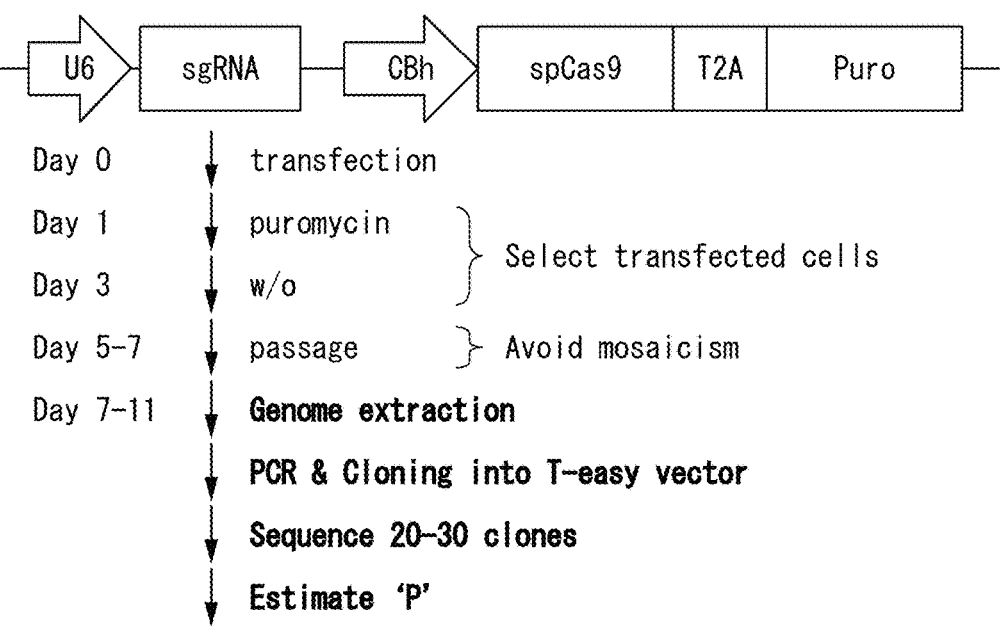
FIGS. 8A and 8B show results of comparing prediction values of Pre-Demo-Prediction and actual measurement values.

Pre-Demo-Prediction is a simple test method for calculating P values by Formula (1) above. The Pre-Demo-Prediction was performed according to the protocol shown in FIG. 8A.

A coding sequence of a spacer sequence with respect to an arbitrary target sequence was ligated to a BpiI site of PX459 to produce a p: RCP. The p: RCP was transfected into cells in the same manner as the method described in the section of "(Indel pattern analysis using AIMS cells)" in Example 2, puromycin treatment was performed, and puromycin-resistant cells were selected.

DNA of the obtained puromycin-resistant cells was extracted, a region containing the target sequence was amplified by PCR, and the amplified fragment was inserted into a T-Easy Vector (pGEM-T Easy Vector System; Promega) and cloned. Sequence analysis of 20 to 30 clones was performed, and a proportion of clones in which an indel was confirmed was calculated. This value was taken as an indel induction ratio (P). Furthermore, using the calculated P values, a frequency of monoallelic indels, a frequency of biallelic indels, and a frequency of no indels were respectively predicted by Formulas (m), (b), and (n).

(Evaluation of Indel Pattern Prediction)

An albumin gene (Alb) was selected as a target gene for genome editing. A linker (SEQ ID NOs: 89 and 90) for sgRNA containing a coding sequence of a spacer sequence targeting the Alb was used to produce Alb_PX459, Alb (10C (8A))_PX459, and Alb (25C (23A))_PX459 as a p: RCP. Each of them was introduced into wild-type ES cells, and the Pre-Demo-Prediction was performed as described above. The prediction results are shown in the left graph of FIG. 8B.

Furthermore, in the same manner, transfection and puromycin treatment of Alb PX459 were performed to obtain colonies of puromycin-resistant cells. DNA was extracted from each of the colonies of puromycin-resistant cells, sequence analysis of a region containing the target sequence was performed, and an indel pattern in each of the clones was analyzed. Based on these results, each of a frequency of monoallelic indels, a frequency of biallelic indels, and a frequency of no indels was obtained. The results are shown in the right graph of FIG. 8B.

Figure 8B:
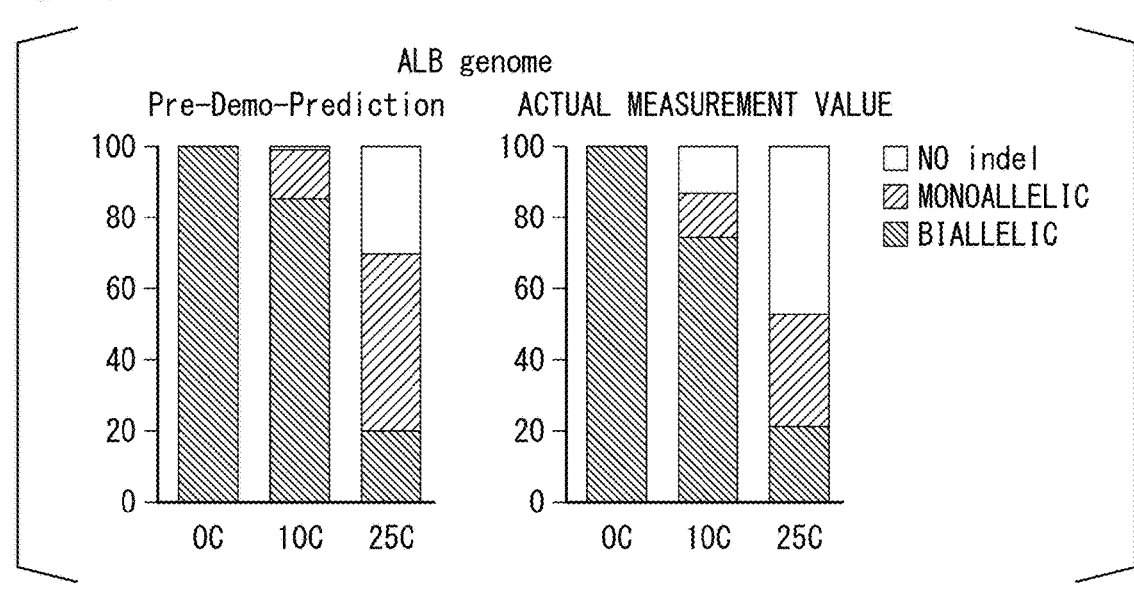

As shown in FIG. 8B, prediction values from the Pre-Demo-Prediction were close to the actual indel pattern. Based on these results, it was shown that an indel pattern can be predicted by the Pre-Demo-Prediction.

[Example 9] Inhibition of Off-Target Effect by 5'-Nucleotide Addition Method (Test Using sgRNA Having 1-Base Mismatch)

Genome editing of a target sequence by an sgRNA having a 1-base mismatch can be thought as off-target genome editing because the target sequence and the spacer sequence do not match. Therefore, whether an off-target effect could be inhibited by the 5'-nucleotide addition method was examined.

Figure 9A:
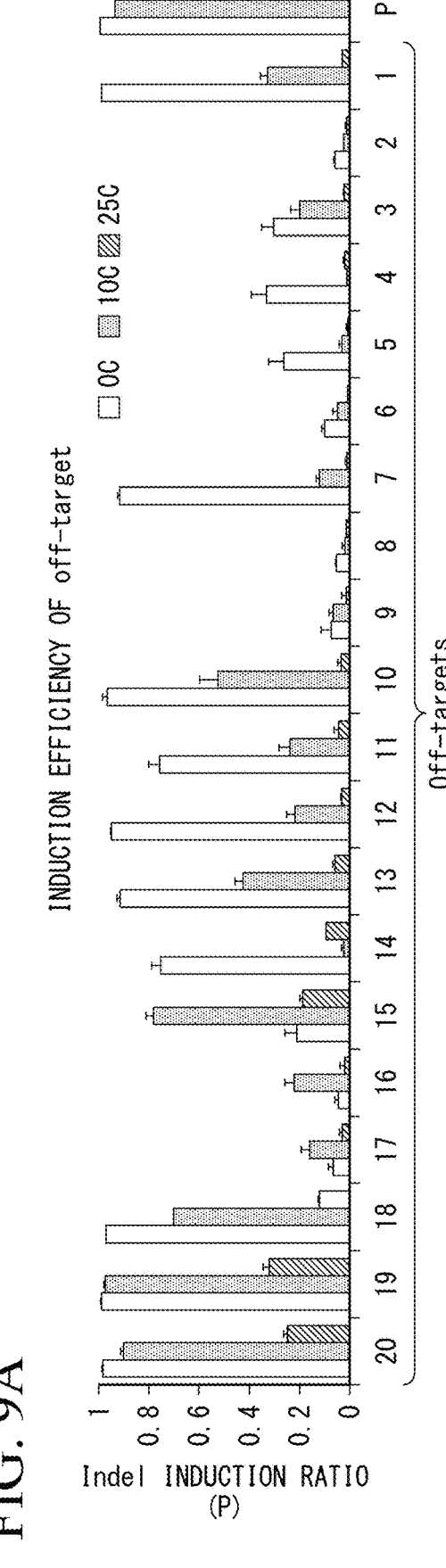
FIGS. 9A to 9C show results of investigating whether an off-target effect can be inhibited by adding nucleotide residues to the 5'-end of a spacer sequence.

FIG. 9A shows results of calculating an indel induction ratio (P) by Formula (1) above based on data of FIGS. 6A to 6C. Genome editing of a target sequence by an sgRNA having a 1-base mismatch at the 1st to 20th locations can be regarded as off-target genome editing.

As shown in FIG. 9A, an off-target action could be inhibited by adding cytosine to the 5'-end. For example, in a case where sgRNA having a mismatch at the 1st location was used, and when cytosine was not added, an indel induction ratio (P) was almost 1. However, when 10 cytosines were added to the 5'-end of a spacer sequence, an indel induction ratio (P) was significantly reduced. On the other hand, in a case where sgRNA having no mismatch was used, and even when 10 cytosines were added, an indel induction ratio (P) did not decrease so much. These results indicate that the 5'-nucleotide addition method can inhibit the off-target effect while maintaining on-target genome editing activity.

(Verification of Off-Target Effect for Off-Target Region in Genome)

With respect to a target sequence (the 5th to 24th of GAGTCCGAGCAGAAGAAGAA: SEQ ID NO: 83 (linker for sgRNA production)) in an EMX1 gene, indels in an MFAP1 gene region that is an off-target region (GAGTCtaAGCAGAAGAAGAA: SEQ ID NO: 91; where portions different from a target sequence in an EMX1 gene are shown in small letters) were verified with HEK 293T cells.

A coding sequence of the spacer sequence targeting the EMX1 gene was inserted into the 10C (8A) linker PX459 or the 25C (23A) linker PX459 which were produced in Example 4, and thereby each of EMX1_PX459 (10C (8A)) and EMX1_PX459 (25C (23A)) was produced. The linkers used to produce the plasmids are set forth in SEQ ID NOs: 83 and 84. These plasmids were introduced into the HEK 293T cells. Transfection and puromycin treatment were performed in the same method as described in the section of "(Production of AIMS cells)" described above. Indels were confirmed by T7E1 assay and sequence analysis.

Figure 9B:
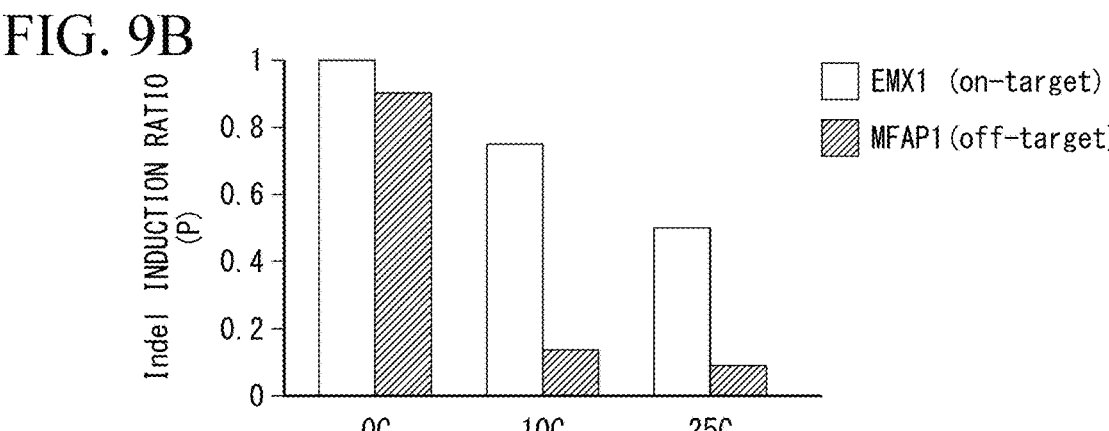

DNA extracted from the HEK 293T cells that had been subjected to the transfection and the puromycin treatment was amplified by PCR (primer for EMX1 on-target region amplification: SEQ ID NOs: 85 and 86; primer for MFAR off-target region amplification: SEQ ID NOs: 92 and 93). For 0C, an amplified fragment was inserted into a T-easy Vector and cloned. Next, the indel induction ratio (P) was determined by assay with T7E1 enzyme (NEB) and sequence analysis. For (P) other than 0C, the amplified PCR product was directly assayed for T7E1. (P) values were calculated from a ratio of an amount of cleavage band and were shown in FIG. 9B.

It was confirmed that by adding cytosine to the 5'-end of the spacer sequence, an indel induction ratio was significantly reduced in the off-target region in the MFAP1 gene than in the target sequence (on-target region) in the EMX1 gene that was the on-target. Based on these results, it was shown that the off-target effect can be reduced by adding a nucleotide to the 5'-end.

In addition to the 10C (8A) linker PX459 or the 25C (23A) linker PX459 produced above, 5C (3A) linker PX459, 15C (13A) linker PX459, 20C (18A) linker PX459, and 30C (28A) linker PX459 were produced. A coding sequence of a spacer sequence targeting the EMX1 gene was inserted to the above linkers, and thereby each of EMX1_PX459 (5C (3A)), EMX1_PX459 (10C (8A)), EMX1_PX459 (15C (13A)), EMX1_PX459 (20C (18A)), EMX1_PX459 (25C (23A)), and EMX1_PX459 (30C (28A)) was produced. The linkers used to produce the plasmids are set forth in SEQ ID NOs: 117 to 124. These plasmids were introduced into the HEK 293T cells. Transfection and puromycin treatment were performed in the same method as described in the section of "(Production of AIMS cells)" described above. Indels were confirmed by T7E1 assay and sequence analysis.

Figure 9C:
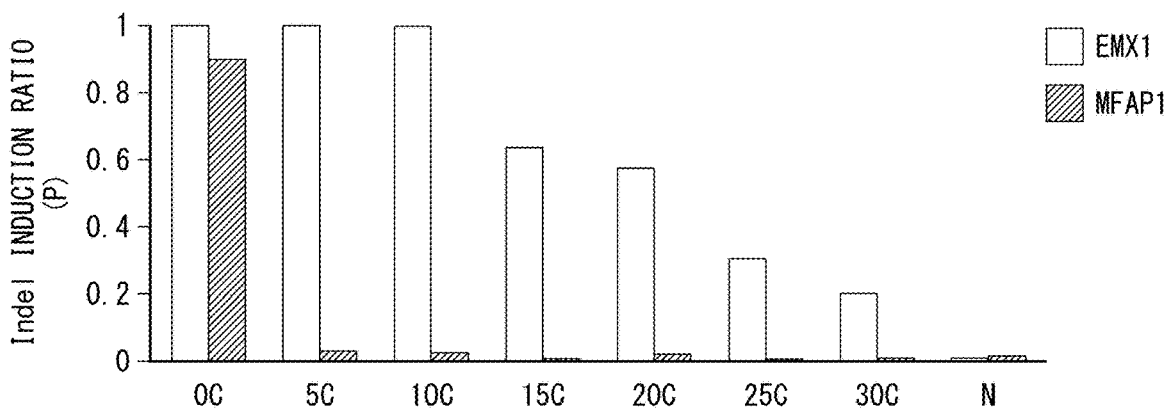

DNA extracted from the HEK 293T cells that had been subjected to the transfection and the puromycin treatment was amplified by PCR (primer for EMX1 on-target region amplification: SEQ ID NOs: 85 and 86; primer for MFAR off-target region amplification: SEQ ID NOs: 92 and 93). For 0C, an amplified fragment was inserted into a T-easy Vector and cloned. Next, the indel induction ratio (P) was determined by assay with T7E1 enzyme (NEB) and sequence analysis. For (P) other than 0C, the amplified PCR product was directly assayed for T7E1. (P) values were calculated from a ratio of an amount of cleavage band and were shown in FIG. 9C.

It was confirmed that by adding cytosine to the 5'-end of the spacer sequence, an indel induction ratio was significantly reduced in the off-target region in the MFAP1 gene than in the target sequence (on-target region) in the EMX1 gene that was the on-target. Based on these results, it was shown that the off-target effect can be reduced by adding a nucleotide to the 5'-end.

[Example 10] Repair Test of Genetic Disease Mutation in Fibrodysplasia Ossificans Progressiva (FOP)

(Cell Line)

Human iPS cells (wt/R206H) having a FOP genetic disease mutation ((where arginine (CGC) at the 206th location mutated to histidine (CAC): R206H)) were used for one of the alleles of an ACVR1 gene.

(Repair Method for FOP Genetic Disease Mutation)

Figure 10A:
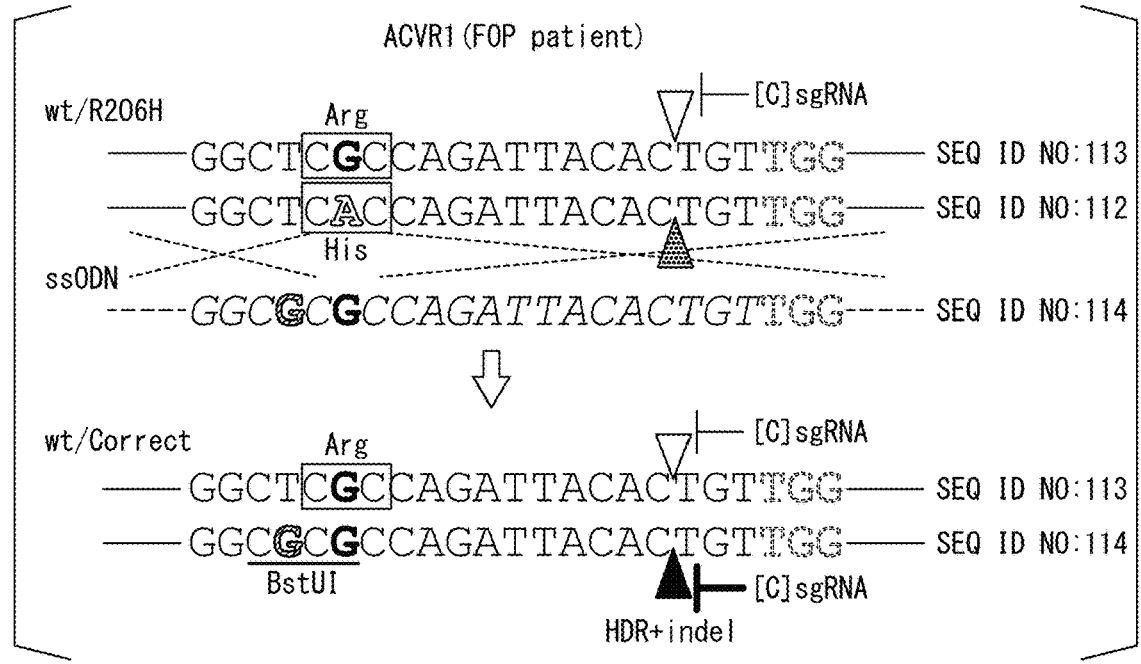
FIGS. 10A to 10C show results of a repair test for a genetic disease mutation in fibrodysplasia ossificans progressiva (FOP).

FIG. 10A shows an outline of a repair method for an FOP genetic disease mutation.

As a selective target sequence for a mutant allele (R206H) of the ACVR1 gene, (GGCTC[A]CCAGATTACACTGT: SEQ ID NO: 112; where [ ] indicates a mutant base) was selected, and DNA (SEQ ID NOs: 100 and 101) in which an adapter sequence had been added to the target sequence was produced. This DNA was inserted into a BPiI site of PX459, the 5C (3A) linker PX459, the 10C (8A) linker PX459, and the 15C (13A) linker PX459, and thereby each of ACVR1 (R206H)_PX459, ACVR1 (R206H)_PX459 (5C (3A)), ACVR1 (R206H)_PX459 (10C (8A)), and ACVR1 (R206H)_PX459 (15C (13A)) was produced. As a result, plasmids for editing the mutant allele (R206H) which express SgRNA containing a sequence in which 0, 5 (1 of which is A), 10 (1 of which is A), or 15 (1 of which is A) cytosines had been added to the 5'-end of a spacer sequence, and Cas9 were obtained. When these plasmids were introduced into the human iPS cells (wt/R206H), the mutant allele (R206H) was preferentially cleaved by the Cas9 (dot arrow in FIG. 10A).

Next, as template DNA for repair of the mutant allele, single-strand oligo donor DNA (ssODN) having a base sequence set forth in SEQ ID NO: 102 was produced. In addition to [G] that repairs a mutation in R206H, the ssODN has a silent mutation [G] 2 bases 5' upstream of the above [G]. The silent mutation [G] prevents further indel introduction after genome repair (black arrow in FIG. 10A). Furthermore, it is possible to confirm the presence of an ACVR1 gene (wt/correct) having a wt allele and a repaired allele (correct). When the mutant allele (R206H) is genome-edited, the action of Cas9 often causes deletion of the mutant allele (R206H) or long deletion (unknown indel). At this time, in a case where the silent mutation [G] is not present, a clone having wt/unknown indel may be mistakenly recognized as a clone having wt/correct. Furthermore, a cleavage site of a restriction enzyme BstUI is introduced by the silent mutation [G], and therefore it is possible to easily perform genotyping of the repair clone.

Each of the plasmids and the ssODN were introduced into the human iPS cells (wt/R206H), and Homology Directed Repair (HDR) was induced.

(Genotype Analysis)

Genotype analysis was performed on iPS cell clones in which HDR had been induced by the above method, and HDR induction efficiency was confirmed. For clones after HDR induction, DNA at the target site was amplified by PCR using primers Pr. KW1181 (SEQ ID NO: 103) and Pr. KW1182 (SEQ ID NO: 104). For a portion in which an amplified fragment was cleaved by BustUI, sequence analysis was performed using the Pr. KW1181.

(Results)

Figure 10B:
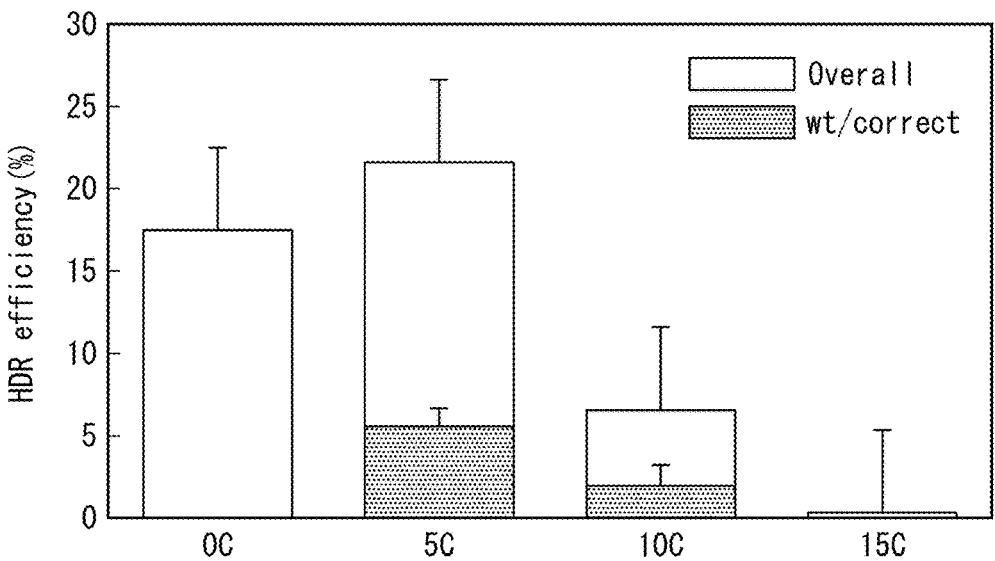

The results are shown in FIG. 10B. In FIG. 10B, "overall" is a proportion of clones containing genotypes (indel/correct, wt/correct+indel, and the like) other than wt/correct, among clones in which HDR was induced. As shown in FIG. 10B, a correctly repaired clone of wt/correct could not be obtained with sgRNA (0C) in which cytosine was not added to the 5'-end. On the other hand, a clone of wt/correct could be obtained with sgRNAs (5C, 10C) in which 5 or 10 cytosines were added.

(Evaluation of Target Genome Cleavage Efficiency)

One of the plasmids for editing the mutant allele (R206H) was introduced into human iPS cells (wt/R206H), and genome editing was performed with a mutant allele (R206H) within an ACVR1 gene sequence as a target. Next, the genome was recovered from the cells, and DNA was amplified by PCR using the primers Pr. KW1181 and Pr. KW1182. Next, cleavage assay by T7 Endonucleoase I (T7E1) (purchased from New England Biolabs Japan Inc.) was performed using the amplified fragment, and indel induction efficiency was measured.

Figure 10C:
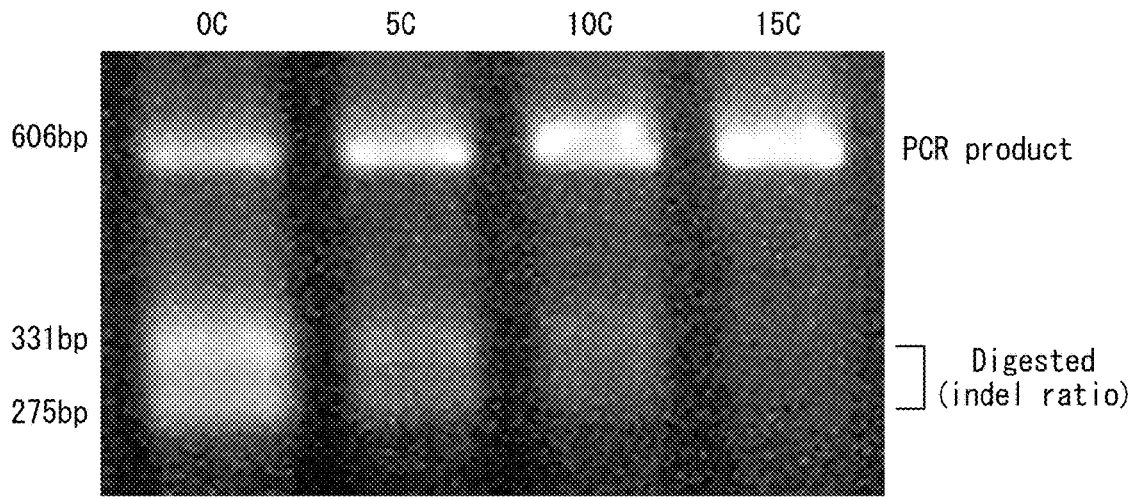

The results are shown in FIG. 10C. It was confirmed that indel induction efficiency was significantly reduced with the sgRNAs (5C, 10C, 15C) in which cytosines were added as compared with the sgRNA (0C) in which cytosine was not added to the 5'-end. It was shown that this reduction in indel induction efficiency was required for acquisition of wt/correct clones (FIG. 10B).

[Example 11] Production Test of FOP Genetic Disease Model (Cell Line)

Mouse ES cells (wt/wt) not having a mutation in an Acvr1 gene were used.

(Induction Method for FOP Genetic Disease Mutation)

Figure 11A:
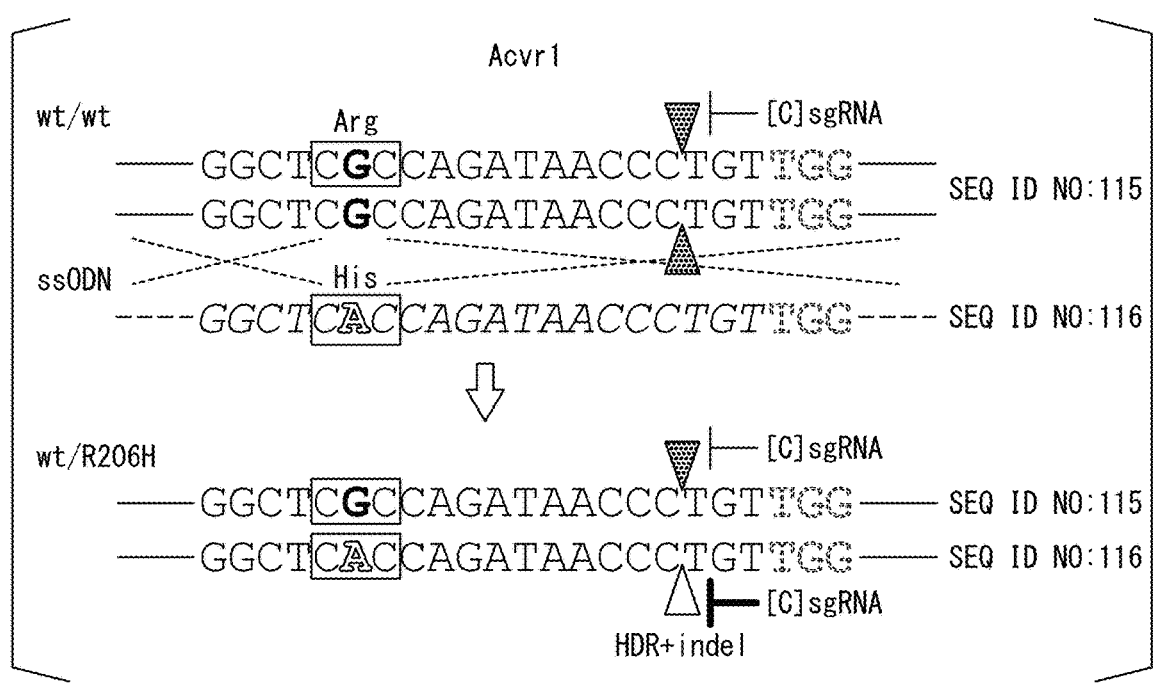
FIGS. 11A to 11D show results of a test of producing an FOP genetic disease model.

FIG. 11A shows an outline of an induction method for an FOP genetic disease mutation.

As a target sequence with respect to an Acvr1 gene (wt/wt), (GGCTCGCCAGATAACCCTGT: SEQ ID NO: 115) was selected, and DNA (SEQ ID NOs: 105 and 106) in which an adapter sequence had been added to the target sequence was produced. This DNA was inserted into a BPiI site of the PX459, the 5C (3A) linker PX459, the 10C (8A) linker PX459, the 15C (13A) linker PX459, the 20C (18A) linker PX459, the 25C (23A) linker PX459, and the 30C (28A) linker PX459. Thereby, each of ACVR1 (R206H)_PX459, ACVR1 (R206H)_PX459 (5C (3A)), ACVR1 (R206H)_PX459 (10C (8A)), ACVR1 (R206H)_PX459 (15C (13A)), ACVR1 (R206H)_PX459 (20C (18A)), ACVR1 (R206H)_PX459 (25C (23A)), and ACVR1 (R206H)_PX459 (30C (28A)) was produced. As a result, plasmids for editing the Acvr1 gene (wt/wt) which express SgRNA containing a sequence in which 0, 5 (1 of which is A), 10 (1 of which is A), 15 (1 of which is A), 20 (1 of which is A), 25 (1 of which is A), or 30 (1 of which is A) cytosines had been added to the 5'-end of a spacer sequence, and Cas9 were obtained. When these plasmids were introduced into mouse ES cells, a wt allele of the Acvr1 gene was cleaved by the Cas9 (dot arrow in FIG. 11A).

Next, as a template DNA for mutation induction, ssODN having a base sequence set forth in SEQ ID NO: 107 was produced. The ssODN has [A] that induces a mutation in R206H.

Each of the plasmids and the ssODN were introduced into the mouse ES cells (wt/wt)), and Homology Directed Repair (HDR) was induced. The plasmids can also induce an indel against a mutant allele (R206H) of a heterozygous mutant clone (wt/R206H) (white arrow in FIG. 11A), but indel induction for the mutant allele (R206H) is inhibited due to an off-target inhibitory effect of 5'-nucleotide-added sgRNA. It was thought that, therefore, the heterozygous mutant clone (wt/R206H) could be efficiently obtained.

(Genotype Analysis)

Genotype analysis was performed on ES cell clones in which HDR had been induced by the above method, and HDR induction efficiency was confirmed. For clones after HDR induction, DNA at the target site was amplified by PCR using primers Pr. KW1201 (SEQ ID NO: 108) and Pr. KW1202 (SEQ ID NO: 109). Sequence analysis was performed on the amplified fragment using the Pr. KW1201.

(Results)

Figure 11B:
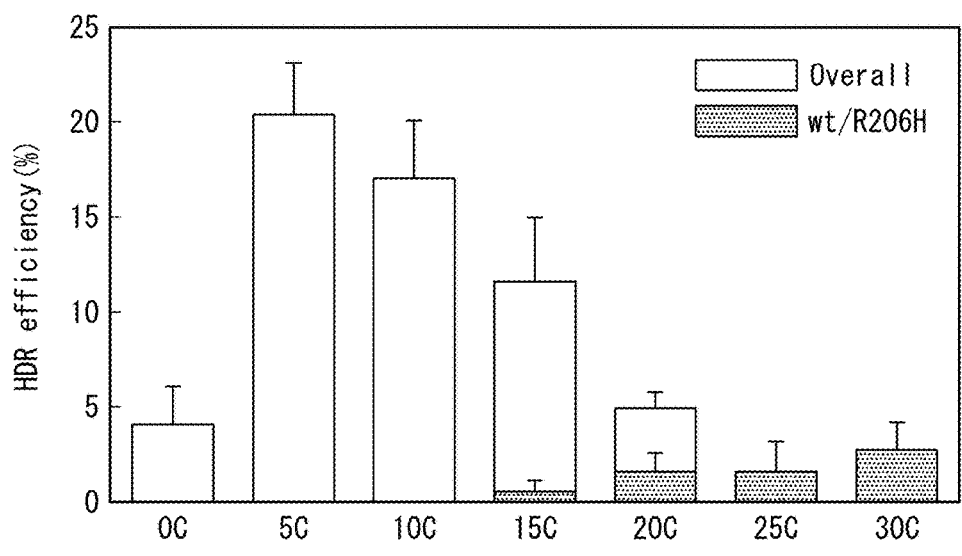
Figure 11C:
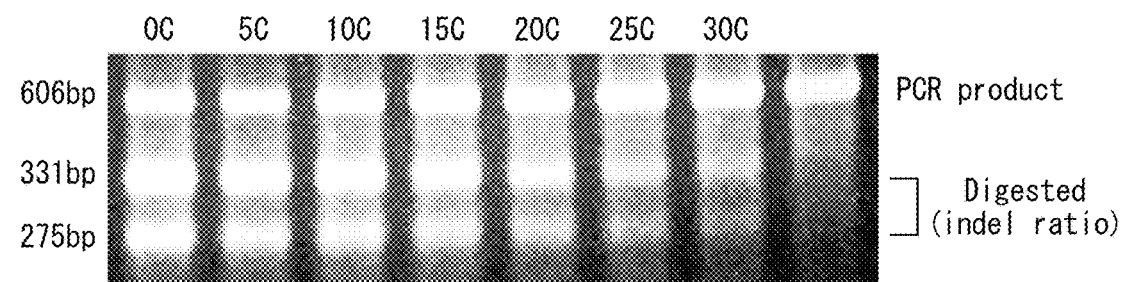

The results are shown in FIG. 11B. In FIG. 11B, "overall" is a proportion of clones containing genotypes (indel/R206H, wt/R206H+indel, and the like) other than wt/R206H, among clones in which HDR was induced. As shown in FIG. 11B, HDR induction efficiency was the highest in the sgRNA (5C) in which 5 cytosines were added to the 5'-end. HDR induction efficiency also decreased as the Cas9 activity decreased due to the increase in the number of cytosine added (FIG. 11C). On the other hand, an acquisition rate of the heterozygous mutant clone (wt/R206H) increased as the Cas9 activity decreased due to the increase in the number of cytosine added (FIG. 11C).

(Evaluation of Target Genome Cleavage Efficiency)

One of the plasmids for editing the wt allele was introduced into mouse ES cells (wt/wt), and genome editing was performed with an Acvr1 gene sequence as a target. Next, the genome was recovered from the cells, and DNA was amplified by PCR using the primers Pr. KW1201 and Pr. KW1202. Next, cleavage assay by T7 Endonucleoase I (T7E1) (purchased from New England Biolabs Japan Inc.) was performed using the amplified fragment, and indel induction efficiency was measured.

The results are shown in FIG. 11C. It was confirmed that indel induction efficiency decreased as the number of cytosines added increased. In FIG. 11C, pX459 is a negative control in which sgRNA not having a spacer sequence was used.

(Production of FOP Genetic Disease Animal Model)

Figure 11D:
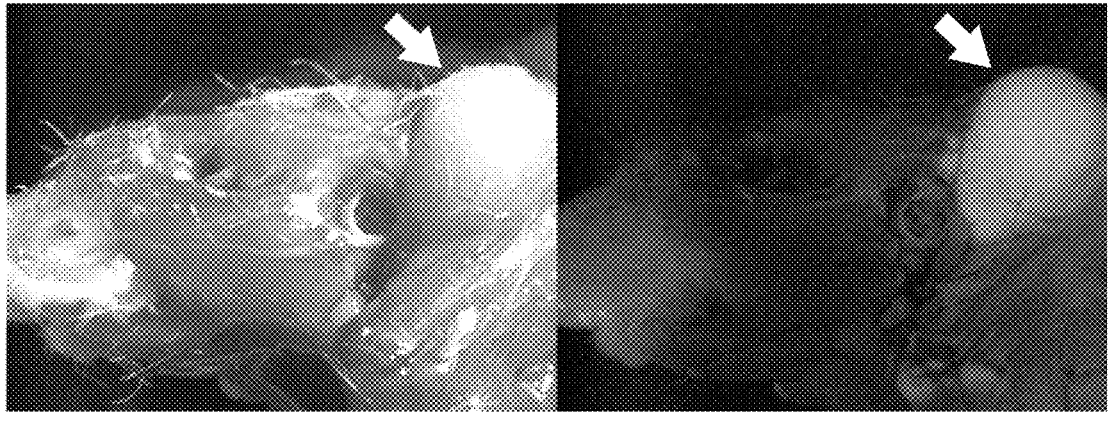

The heterozygous mutant clone (wt/R206H) acquired in the above test was microinjected into a fertilized mouse egg to produce a chimeric mouse. In the chimeric mouse, abnormal bone formation was observed at a site to which ES cells contributed (arrow in FIG. 11D). Based on the above results, it was verified that a FOP genetic disease animal model can be produced.

[Example 12] Cytotoxicity Evaluation Test (Cytotoxicity Evaluation Test Using AIMS)

Genome editing of AIMS cells was performed in the same manner as in Example 4 with a target sequence of P2A (TAACTTCAGCCTGCTGAAGC: SEQ ID NO: 95) as a target. As a spacer sequence, a sequence in which 0 to 20 cytosines were added to the 5'-end of the P2A target sequence was used. After the genome editing, the number of cells was counted.

Figure 12A:
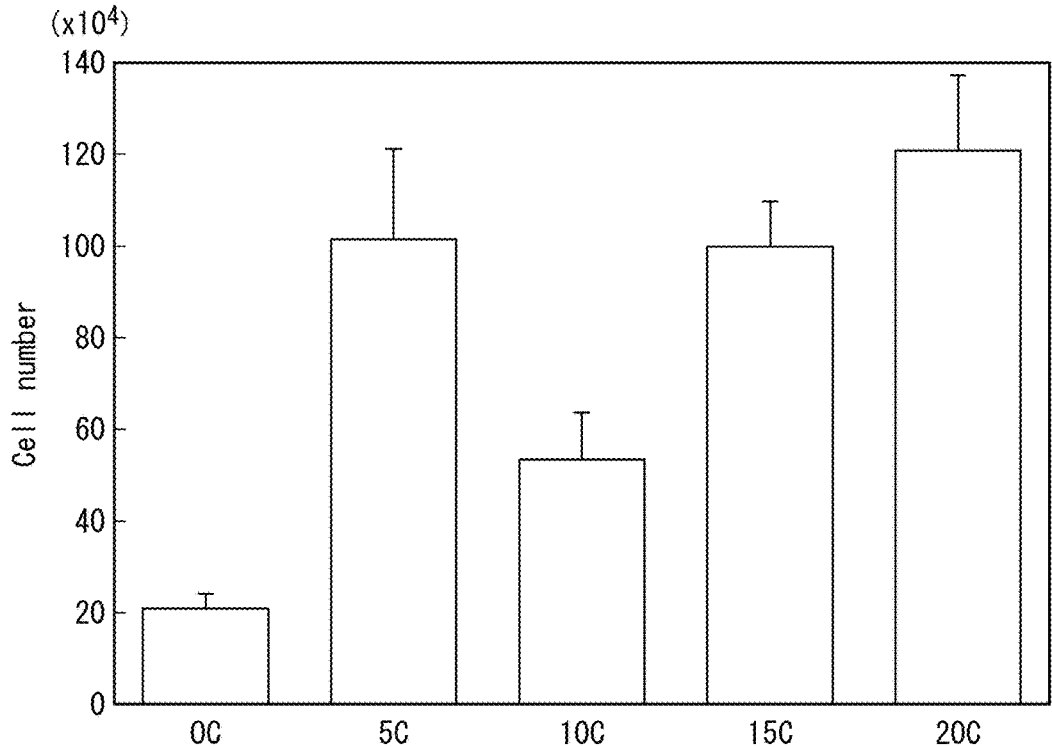
FIG. 12A shows results of a cytotoxicity evaluation test using an AIMS.

The results are shown in FIG. 12A. In sgRNA (0C) in which cytosine was not added, the number of cells was reduced to ⅕ as compared with sgRNA (5C) in which 5 cytosines were added. As shown in FIG. 4B, indel induction efficiency in both of the sgRNA (0C) and the sgRNA (5C) was almost 100%. Therefore, it was suggested that by adding cytosine, it is possible to inhibit cytotoxicity that is not involved in genome cleavage and indel induction efficiency.

(Cytotoxicity Evaluation Test by Genome Editing with ACVR1 as Target)

As a target sequence with respect to an ACVR1 gene, (GGCTCGCCAGATTACACTGT: SEQ ID NO: 113) was selected, and DNA (SEQ ID NOs: 110 and 111) in which an adapter sequence had been added to the target sequence was produced. This DNA was inserted into a BpiI site of PX459, the 5C (3A) linker PX459, the 10C (8A) linker PX459, the 15C (13A) linker PX459, and the 20C (18A) linker PX459, and thereby each of ACVR1 (R206H)_PX459, ACVR1 (R206H)_PX459 (5C (3A)), ACVR1 (R206H)_PX459 (10C (8A)), ACVR1 (R206H)_PX459 (15C (13A)), and ACVR1 (R206H)_PX459 (20C (18A)) was produced. As a result, plasmids for editing wt/wt which express SgRNA containing a sequence in which 0, 5 (1 of which is A), 10 (1 of which is A), 15 (1 of which is A), or 20 (1 of which is A) cytosines had been added to the 5'-end of a spacer sequence, and Cas9 were obtained. These plasmids were introduced into human iPS cells (wt/wt), and genome editing was performed. After the genome editing, the number of cells was counted.

Figure 12B:
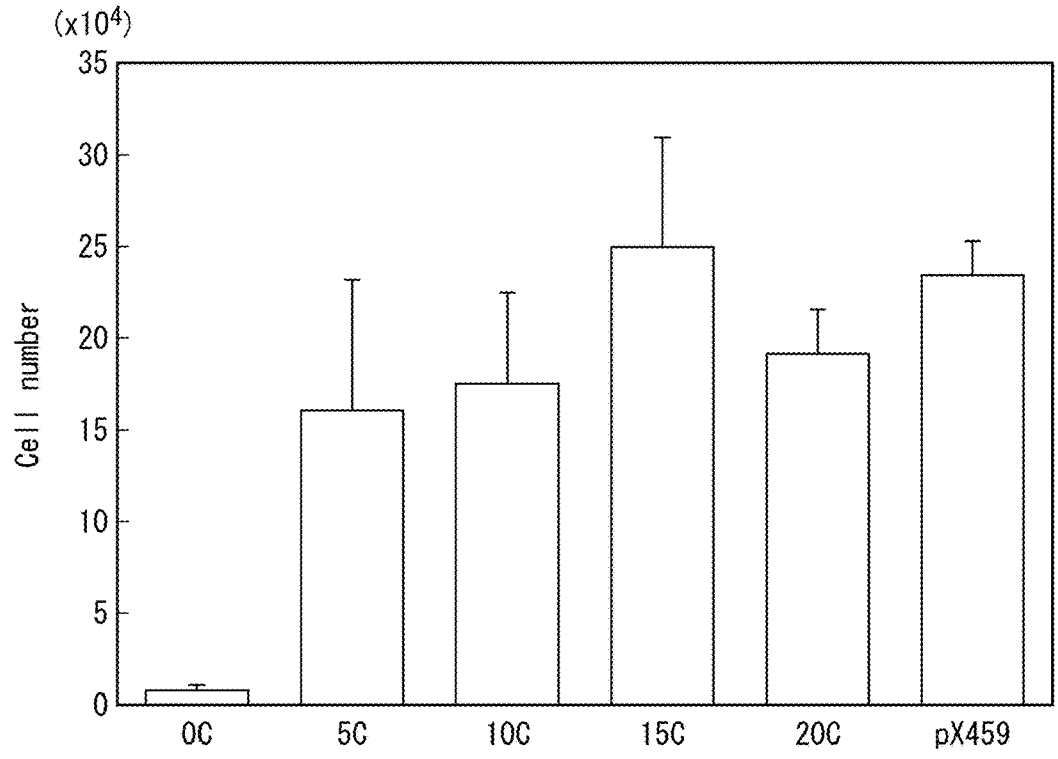
FIG. 12B shows results of a cytotoxicity evaluation test by genome editing with ACVR1 as a target.

The results are shown in FIG. 12B. In sgRNA (0C) in which cytosine was not added, the number of cells was reduced to 1/22 as compared with sgRNA (5C) in which 5 cytosines were added.

Figure 13A:
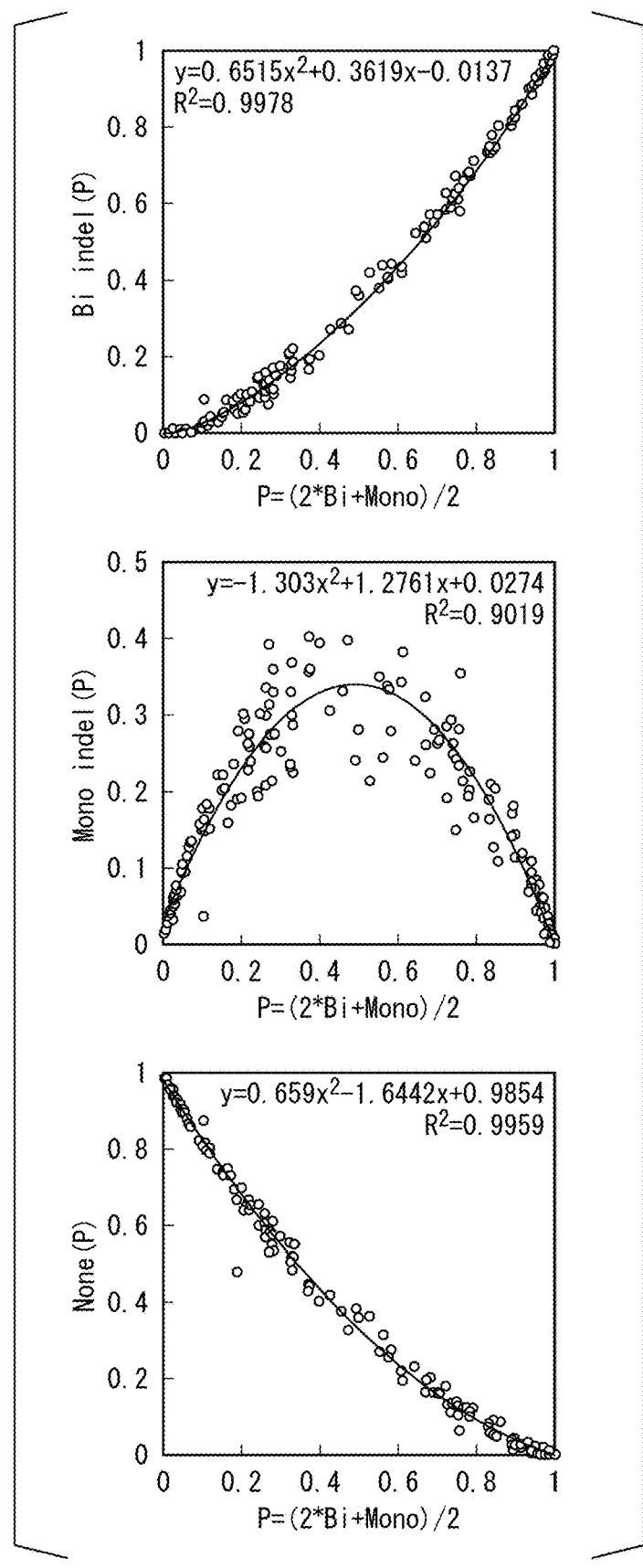
FIG. 13A is a graph plotting P values calculated from 253 pieces of data by an AIMS on a horizontal axis, and proportions of biallelic indels proportion (Bi; upper figure), monoallelic indels (Mono; middle figure), and no indels (Nono; lower figure) on a vertical axis.

[Example 13] Calculation of Indel Induction Ratio (Probability: P) and Prediction of Frequency of Indels 253 pieces of data (consisting of all of C-added gRNA, mismatch gRNA, and C-added+mismatch gRNA) obtained from AIMS were acquired, and P values were calculated by Formula (1) above based on these pieces of data. The calculated P values were plotted on the horizontal axis, and indel data values P's of each of Bi, Meno, and None were plotted on the vertical axis. From this graph, mathematical formulas of the quadratic function were obtained (FIG. 13A). By applying the P values to these obtained mathematical formulas, each of indel proportions of Bi, Mono, and None can be predicted.

Figure 13B:
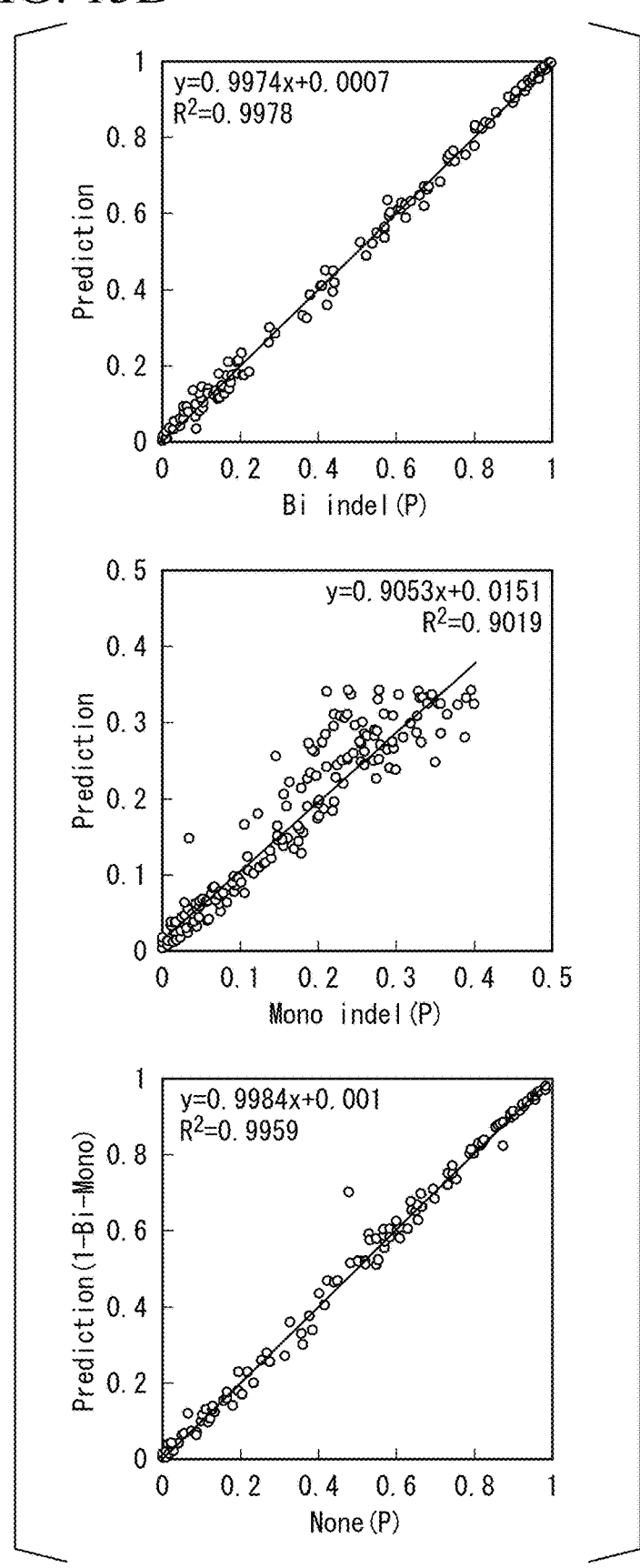
FIG. 13B shows results of predicting proportions of biallelic indels proportion (Bi; upper figure), monoallelic indels (Mono; middle figure), and no indels (None; lower figure) by mathematical formulas obtained from the graphs of FIG. 13A. Actual measurement values (horizontal axis) and prediction values (vertical axis) from the mathematical formulas showed a high correlation.

FIG. 13B shows a relationship between actual measurement values and prediction values from the above formulas. The actual measurement values Bi indel (P), Mono indel (P), and None (P) were plotted on the horizontal axis, and the prediction values (Prediction) were plotted on the vertical axis. The actual measurement values and the prediction values showed a high correlation.

In the lower graph of FIG. 13B, Bi indel (P)+Mono indel (P)+None (P)=1, and therefore production was performed as None (P)=1-Bi indel (P)-Mono indel (P).

Figure 13C:
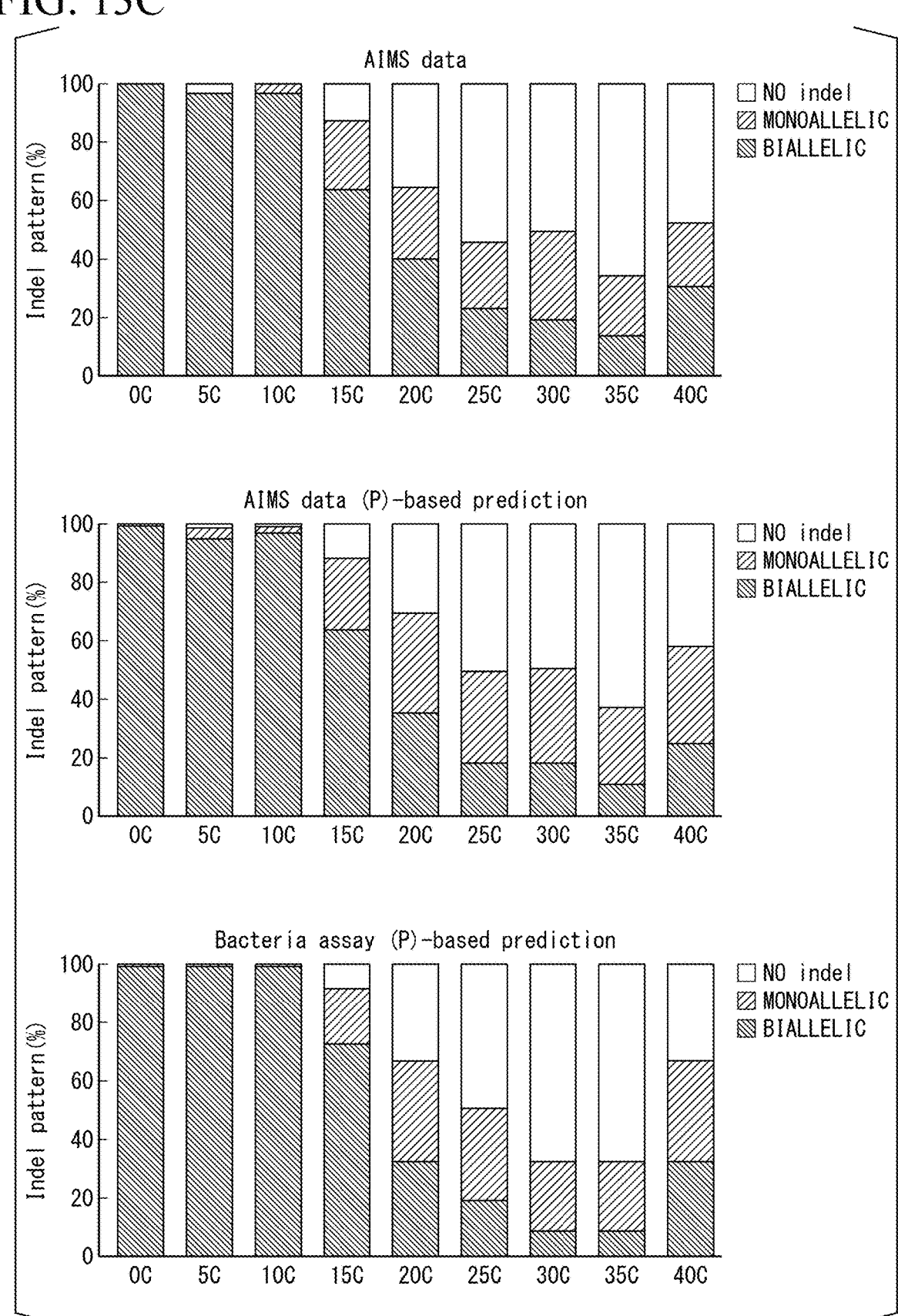
FIG. 13C shows results of performing genome editing with P2A as a target by a Cdh1-P2A-AIMS. The upper figure shows actual data in a case where genome editing was performed with P2A as a target by a Cdh1-P2A-AIMS. The middle figure shows a prediction graph created by applying the P values calculated by Formula (1) above to the mathematical formulas (P=x) of FIG. 13A from the obtained data. The lower figure shows a prediction graph for indel patterns obtained based on a prediction method for a genome editing pattern according to one embodiment of the present invention.

The upper figure of FIG. 13C shows actual data in a case where genome editing was performed with P2A as a target by a Cdh1-P2A-AIMS.

The middle figure of FIG. 13C shows a prediction graph created by applying the P values calculated by Formula (1) above to the mathematical formulas (P=x) of FIG. 13A from the obtained data.

In the lower graph of FIG. 13C, PCR was performed on the genome extracted during the experiment in the upper graph of FIG. 13C. P values were obtained from bacterial (*Escherichia coli*) assay (Example 8: Pre-Demo-Prediction) performed according to the "[Prediction method for genome editing pattern]" described above. An indel pattern prediction graph obtained by applying the P values to the mathematical formulas of FIG. 13A is shown. The lower graph of FIG. 13C almost matches the upper graph of FIG. 13C, and therefore effectiveness of the bacterial assay was proved in addition to accuracy of the mathematical formulas of FIG. 13A. Therefore, even in a case of targeting an intrinsic gene (genome), and even without using AIMS, an intel pattern for each allele can be accurately predicted by performing PCR on a cell genome after genome editing induction and performing bacterial assay.

[Example 14] Prediction by Compound Heterozygous

Figure 14A:
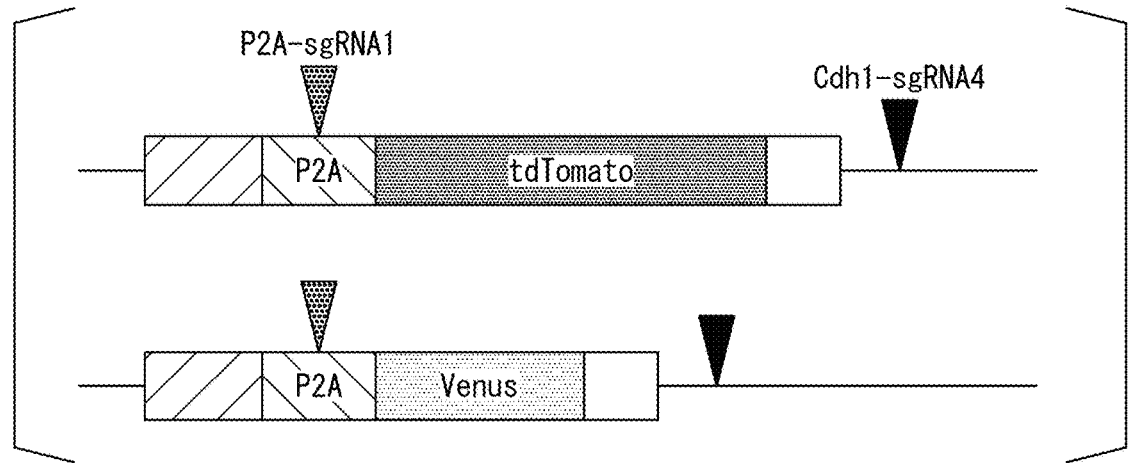
FIG. 14A shows an outline of a production method for a Compound heterozygous. Target locations of P2A-sgRNA1 and Cdh1-sgRNA4 are shown.
Figure 14B:
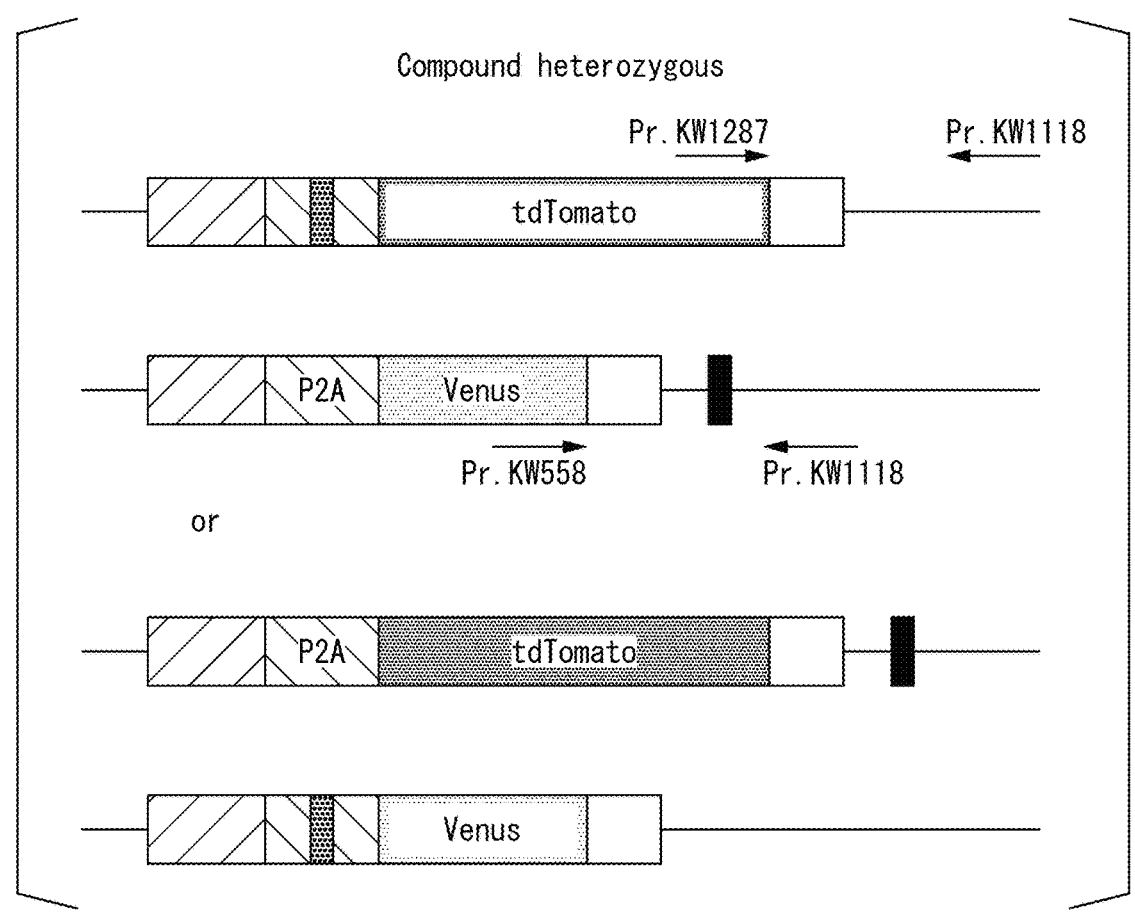
FIG. 14B shows an outline of a production method for a Compound heterozygous. A genomic constitution after genome editing with P2A-sgRNA1 and Cdh1-sgRNA4, and annealing locations of each primer are shown.

Two target sequences of P2A-sgRNA1 (linker SEQ ID NOs: 67 and 68) and Cdh1-sgRNA4 (linker SEQ ID NOs: 125 and 126) were set for Cdh1-P2A-AIMS ES cells (FIG. 14A). Each of monoallelic indels was generated in different alleles (transformer relationship), and a Compound heterozygous indel clone was produced by a single recombination operation (FIG. 14B). Genotype was determined by a fluorescence pattern (for the P2A site: no sequencing required) and sequencing of PCR products by PCR with set primers (intrinsic Cdh1 gene region). The genotype of the Cdh1-sgRNA4 target region of a Tomato allele is Pr. KW1287 (SEQ ID NO: 127) and Pr. KW1118 (SEQ ID NO: 54). The genotype of the Cdh1-sgRNA4 target region of a Venus allele is Pr. KW558 (SEQ ID NO: 39) and Pr. KW1118 (SEQ ID NO: 54).

Table 6 shows the results.

TABLE 6

| | Mono (P) | Compound Prediction (P) | Data |
|---|---|---|---|
| P2A-[0 C.] | 0 | 0 | 0/382 |
| Cdh1-[0 C.] | 0 | | |
| P2A-[25 C.] | 0.31 | 0 | 0/294 |
| Cdh1-[0 C.] | 0 | | |
| P2A-[25 C.] | 0.31 | 0.047 | 21/383 |
| Cdh1-[25 C.] | 0.30 | | (P = 0.050) |

P2A-sgRNA1 and Cdh1-sgRNA4 were tested with a combination of sgRNA (0C) in which 0 cytosine was added and sgRNA (25C) in which 25 cytosines were added. Even when [0C] or only Cdh1 was [25C], a Compound heterozygous indel clone could not be obtained. 21 clones could be obtained between [25C]. Therefore, it was shown that induction of a Mono indel by decreased activity is essential for both targets.

From the probability of occurrence of a monoallelic indel of the 21/363 clone, the Compound heterozygous indel probability was calculated to be P=0.050. It was verified whether this P value could be predicted from the Mono P value by the bacterial assay according to FIG. 13. Using the sgRNA of [0C] and the sgRNA of [25C] of P2A-sgRNA1 and Cdh1-sgRNA4 and, each of the predicted Mono P values was obtained by the mathematical formulas of FIG. 13A from bacterial assay (Mono (P) in Table 6). The Compound prediction P value was obtained from P2A Mono (P) x Cdh1 Mono (P)×1/2 (probability of becoming a trance) and was 0.047. This predicted P value of 0.047 almost matches the actual measurement P value of 0.050, and therefore it was proved that an occurrence rate of a compound heterozygous indel also can be accurately predicted by the bacterial assay.

In the present test, a compound heterozygous within one gene was produced, but in the same principle, for example, it can also be applied to prediction of a probability of inducing indels as all hetero types, all homo types or mixed types for multiple different genes.

For example, three genes of Genes A to C can be predicted as follows.

All hetero type *P*=Gene *A* Mono (*P*)×Gene *B* Mono (*P*)×Gene *C* Mono (*P*)

All homo type *P*=Gene *A* Bi (*P*)×Gene *B* Bi (*P*)× Gene *C* Bi (*P*)

Mixed type *P*=Gene *A* Bi (*P*)×Gene *B* Mono (*P*)× Gene *C* None (*P*)

[Example 15] In Vitro Cleavage Assay

PCR was performed using a P. KW13-3 plasmid (SEQ ID NO: 4) as a template, and using Pr. KW541 (SEQ ID NO: 41) and Pr. KW607 (SEQ ID NO: 128) as primers. A complex of sgRNA and Cas9 was allowed to act in vitro with respect to 300 ng (951 bp) of the PCR product, and DNA cleavage activity of C-added gRNA-Cas9 was measured (cleaved DNA: 741 bp and 210 bp).

sgRNA of [0C], sgRNA of [10C], and sgRNA of [25C] were produced by the following procedure. PCR was performed using the PX459 plasmid into which the P2A-gRNA1 linker (SEQ ID NOs: 67 and 68) was inserted as a template, and using each of forward primers (Pr. KW1105 (SEQ ID NO: 129), Pr. KW1106 (SEQ ID NO: 130), and Pr. KW1107 (SEQ ID NO: 131)), and a reverse primer (Pr. KW1108 (SEQ ID NO: 132)). Each of the above sgRNAs was obtained by in vitro transcription of this PCR product with T7 RNA polymerase. A Cas9 protein was purchased from Integrated DNA Technologies, Inc.

Figure 15:
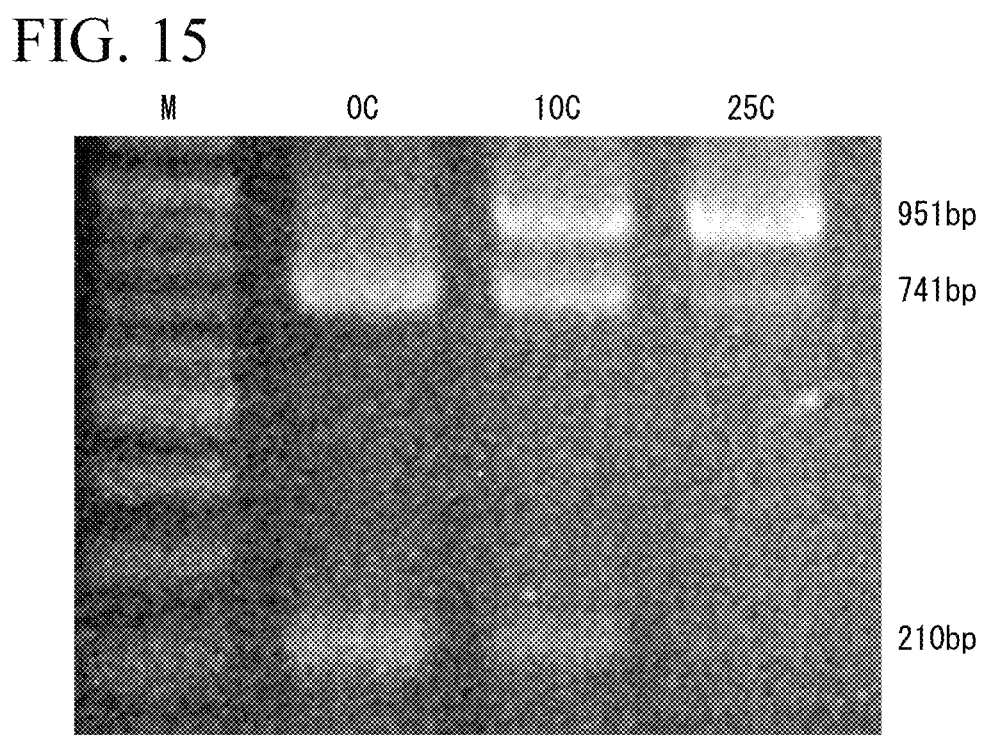

FIG. 15 shows the results. It was confirmed that DNA cleavage activity decreased in a C-strand-dependent manner under the action of the same molar concentration gRNA (200 nM). Therefore, it was shown that the 5'-nucleotide addition method is effective not only in vivo (cell level) but also in vitro.

INDUSTRIAL APPLICABILITY

According to the present invention, a production method for a cell in which only one allele is genome-edited; and a guide RNA, an expression vector, and a kit which can be used in the method are provided. Furthermore, a prediction method for a genome editing pattern, an analysis method for a genome editing pattern, and a cell that can be used in the analysis method are provided.

What is claimed is:

1. A guide RNA comprising a spacer sequence,
wherein 15 or more nucleotide residues are added to the 5'-end of the spacer sequence, and
wherein said 15 or more nucleotide residues comprise a polycytosine or a polyguanine including 15 or more nucleotide residues.

2. The guide RNA according to claim 1,
wherein the spacer sequence has single-base or multiple-base mismatches with respect to a target sequence.

3. An expression vector comprising a sequence encoding the guide RNA according to claim 1.

4. The expression vector according to claim 3, wherein the expression vector further comprises a Cas protein coding sequence and enables a Cas protein to be expressed.

5. The expression vector according to claim 4,
wherein the Cas protein is a Cas9 protein.

6. A production kit for a cell which is genome-edited, the production kit comprising:
(A) at least one guide RNA according to claim 1 and an expression vector comprising a sequence encoding the guide RNA.

7. The production kit according to claim 6 further comprising:
(B) at least one selected from the group consisting of a Cas protein and an expression vector for the Cas protein.

8. The guide RNA according to claim 1,
wherein the guide RNA further comprises a repeat sequence, and
wherein the spacer sequence targets a target region, and the repeat sequence forms base pairs with an anti-repeat sequence derived from a tracrRNA to form a complex with a Cas protein.

9. The guide RNA according to claim 1,
wherein the guide RNA has at least one feature selected from the group consisting of:
(a) a suppressed cytotoxicity as compared with a guide RNA in which no nucleotide residues are added to the 5' end of the spacer sequence;
(b) an increased homology directed repair frequency as compared with a guide RNA in which no nucleotide residues are added to the 5' end of the spacer sequence; and (c) an increased monoallelic frequency of genome editing as compared with a guide RNA in which no nucleotide residues are added to the 5' end of the spacer sequence.

10. A guide RNA, comprising a spacer sequence and a repeat sequence,
wherein the spacer sequence targets a target region, and the repeat sequence forms base pairs with an anti-repeat sequence derived from a tracrRNA to form a complex with a Cas protein,
wherein 15 or more nucleotide residues are added to a 5'-end of the spacer sequence, and wherein said 15 or more nucleotide residues comprise a polycytosine or a polyguanine of 15 or more nucleotide residues,
wherein the guide RNA suppresses cytotoxicity, increases homology directed repair frequency, or increases mono-allelic genome editing frequency in genome editing compared to a guide RNA which does not have a nucleotide residue added to the 5' end of the spacer sequence.

11. An expression vector comprising a sequence encoding the guide RNA according to claim 10.

12. The guide RNA according to claim 1,
wherein the 15 or more nucleotide residues added to the 5'-end of the spacer sequence are 20 or more nucleotide residues.

13. The guide RNA according to claim 1,
wherein the 15 or more nucleotide residues added to the 5'-end of the spacer sequence comprises a guanine nucleotide at the 5'-end of the 15 or more nucleotide residues.

14. The guide RNA according to claim 1,
wherein the 15 or more nucleotide residues added to the 5'-end of the spacer sequence comprise:
a polycytosine consisting of cytosine residues, wherein the polycytosine is at least 5 residues in length,
nucleotide residues consisting of 17 cytosine residues, an adenosine residue, and 2 cytosine residues, in order from the 5' end,
nucleotide residues consisting of 22 cytosine residues, an adenosine residue, and 2 cytosine residues, in order from the 5' end, or
nucleotide residues consisting of 27 cytosine residues, an adenosine residue, and 2 cytosine residues, in order from the 5' end.

* * * * *